(12) United States Patent
Wildgen et al.

(10) Patent No.: US 10,820,912 B2
(45) Date of Patent: Nov. 3, 2020

(54) SURGICAL TOOL ASSEMBLY INCLUDING A CONSOLE, PLURAL SURGICAL TOOLS AND A FOOTSWITCH, WHEREIN THE CONSOLE IS ABLE TO CUSTOM MAP THE FOOTSWITCH TO EACH SURGICAL TOOL

(71) Applicant: STRYKER CORPORATION, Kalamazoo, MI (US)

(72) Inventors: Michael R. Wildgen, Portage, MI (US); Donald Malackowski, Schoolcraft, MI (US); Michael D. Dozeman, Portage, MI (US); Paul M. Hoekstra, Oshtemo Township, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 585 days.

(21) Appl. No.: 15/450,477

(22) Filed: Mar. 6, 2017

(65) Prior Publication Data
US 2017/0172583 A1 Jun. 22, 2017

Related U.S. Application Data

(60) Division of application No. 11/691,767, filed on Mar. 27, 2007, now abandoned, which is a continuation of
(Continued)

(51) Int. Cl.
A61B 17/16 (2006.01)
A61B 17/32 (2006.01)
(Continued)

(52) U.S. Cl.
CPC ......... A61B 17/1626 (2013.01); A61B 17/14 (2013.01); A61B 17/1613 (2013.01);
(Continued)

(58) Field of Classification Search
CPC . A61B 17/14; A61B 17/1613; A61B 17/1622; A61B 17/1626; A61B 17/1628
See application file for complete search history.

(56) References Cited

U.S. PATENT DOCUMENTS

| 4,162,435 A | 7/1979 | Wright |
| 4,876,491 A | 10/1989 | Squires et al. |

(Continued)

FOREIGN PATENT DOCUMENTS

| EP | 0251785 A2 | 1/1988 |
| JP | H11512596 A | 10/1999 |
| JP | 2003-111485 | 4/2003 |

OTHER PUBLICATIONS

"ConMed PowerPro System Material from www.conmed.com/products-powerprocon.php Sep. 2004".
(Continued)

Primary Examiner — Lynsey C Eiseman
Assistant Examiner — Amanda L Steinberg
(74) Attorney, Agent, or Firm — Howard & Howard Attorneys PLLC

(57) ABSTRACT

A powered surgical tool system capable of providing energization signals to plural powered surgical handpieces. The system includes a console to which at least one footswitch is attached. The footswitch can be mapped to control any one of the handpieces connected to the console. The console includes a display on which representations of the footswitch and handpieces connected to the console are presented. The representations of the handpieces are in different colors. When the footswitch is mapped to a specific handpiece, the representation of the footswitch is presented in the same color as the representation of the handpiece to which the footswitch is mapped. When plural footswitches are attached to the console, the representation of each footswitch
(Continued)

is presented in a color corresponding to the color of the representation of the handpiece to which the footswitch is mapped.

20 Claims, 50 Drawing Sheets

Related U.S. Application Data application No. PCT/US2005/034800, filed on Sep. 28, 2005, which is a continuation-in-part of application No. 10/955,381, filed on Sep. 30, 2004, now Pat. No. 7,422,582.

(60) Provisional application No. 60/614,089, filed on Sep. 29, 2004.

(51) Int. Cl.
*A61B 17/14* (2006.01)
*A61B 17/00* (2006.01)

(52) U.S. Cl.
CPC ...... *A61B 17/1622* (2013.01); *A61B 17/1628* (2013.01); *A61B 17/32002* (2013.01); *A61B 2017/00017* (2013.01); *A61B 2017/00199* (2013.01); *A61B 2017/00367* (2013.01); *A61B 2017/00973* (2013.01)

(56) References Cited

U.S. PATENT DOCUMENTS

| | | | |
|---|---|---|---|
| 5,117,165 A | | 5/1992 | Cassat et al. |
| 5,223,771 A | | 6/1993 | Chari et al. |
| 5,342,356 A | * | 8/1994 | Ellman ............... A61B 18/14 606/32 |
| 5,422,521 A | * | 6/1995 | Neer .................. A61C 1/0023 200/86.5 |
| 5,608,300 A | | 3/1997 | Kawabata et al. |
| 5,609,560 A | | 3/1997 | Ichikawa et al. |
| 5,786,681 A | | 7/1998 | Kalpathi |
| 5,821,713 A | | 10/1998 | Holling et al. |
| 5,854,548 A | | 12/1998 | Taga et al. |
| 5,969,496 A | | 10/1999 | Yamada et al. |
| 5,998,946 A | | 12/1999 | Kim |
| 6,017,354 A | * | 1/2000 | Culp .................. A61B 17/1626 604/22 |
| 6,037,724 A | | 3/2000 | Buss et al. |
| 6,172,498 B1 | | 1/2001 | Schmidt et al. |
| 6,623,423 B2 | | 9/2003 | Sakurai et al. |
| 6,750,627 B2 | | 6/2004 | Holdaway |
| 6,951,535 B2 | | 10/2005 | Ghodoussi |
| 7,148,786 B2 | | 12/2006 | Wllems |
| 2003/0093103 A1 | | 5/2003 | Malackowski et al. |
| 2004/0158237 A1 | | 8/2004 | Abboud et al. |
| 2005/0093491 A1 | | 5/2005 | Kruger |
| 2005/0149004 A1 | * | 7/2005 | Schmieding ....... A61B 17/1626 606/1 |
| 2005/0182393 A1 | | 8/2005 | Abboud |
| 2006/0073048 A1 | | 4/2006 | Malackowski |
| 2007/0250098 A1 | | 10/2007 | Malackowski et al. |

OTHER PUBLICATIONS

"ConMed/Linvatec, PowerPro Advantage console Advertisement www.conmed.com Sep. 2004".

"Fairchild Semiconductor, App. Brief 42020 the Smart Start Technique for BLDC Motors, Oct. 2000".

"PCT App. No. PCT/US2005/034800, Search Report and Written Opinion of the International Search Authority, dated Jun. 29, 2006".

English language abstract for JPH 11-512596 extracted from espacenet.com database on Dec. 18, 2017, 2 pages.

Filka, R. et al., "A Seamless Whole Speed Range Control of Interior PM Synchronous Machine Without Position Transducer", Power Electronics and Motion Control Conference, 12th International, 2006, 9 pages.

\* cited by examiner

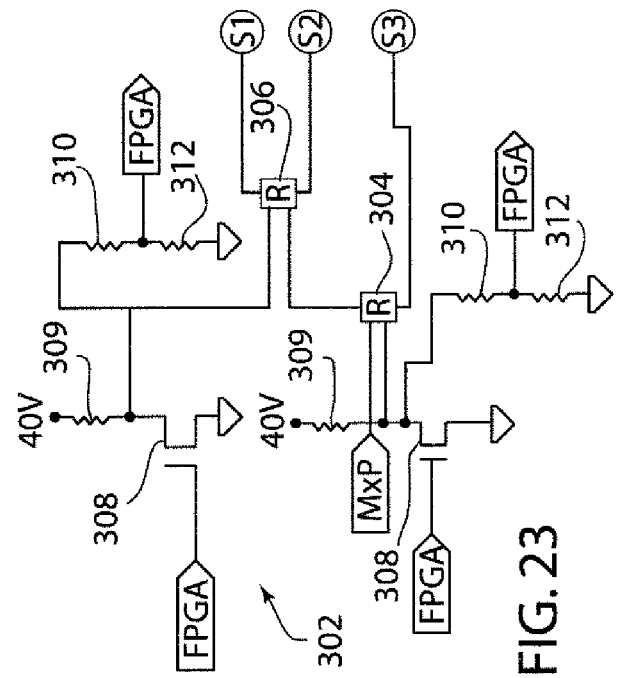
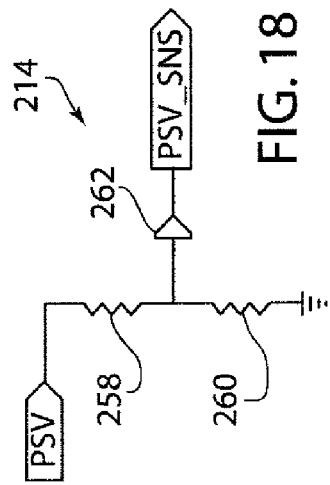
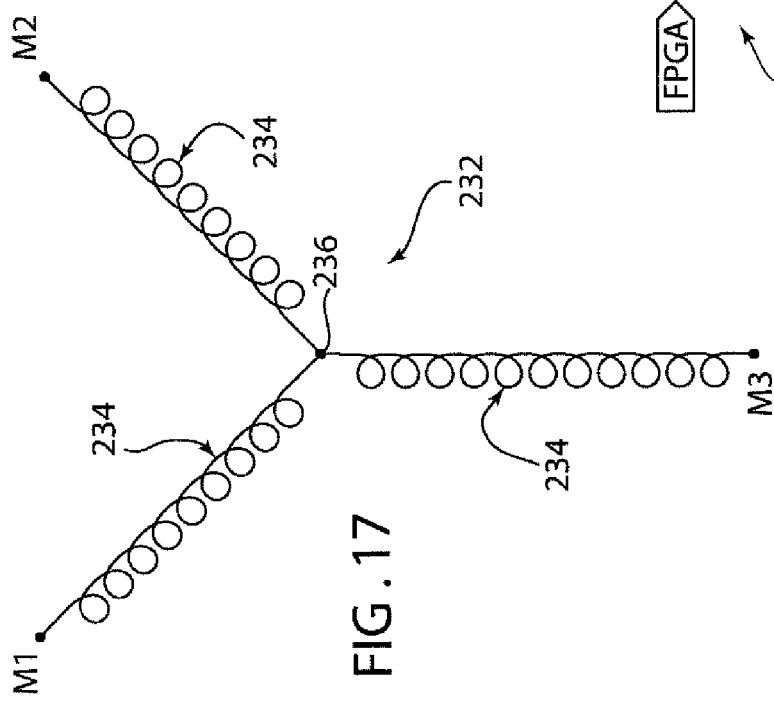

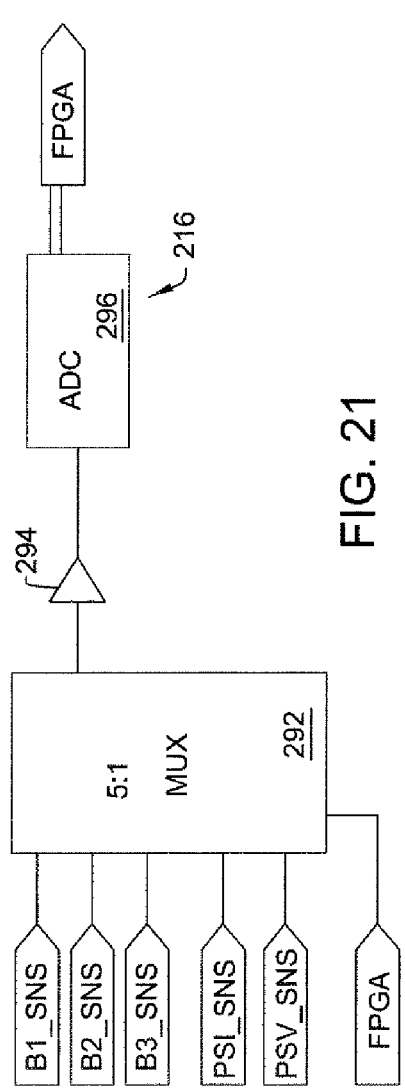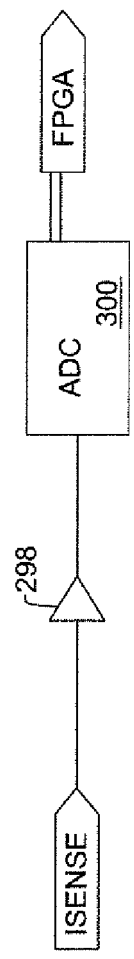

| POWER DRIVER NO. 1 ASSNMNT | 322 |
|---|---|
| POWER DRIVER NO. 2 ASSNMNT | 322 |

| POT. MAX. PWR DRW H_P_1 | 542a |
|---|---|
| POT. MAX. PWR DRW H_P_2 | 542b |
| POT. MAX. PWR DRW H_P_3 | 542c |
| POT. MAX PWR DRW ACT H_Ps | 544 |

FIG. 36

| SWITCHING FREQUENCY | 588 |
|---|---|
| DEAD TIME PERIOD | 590 |
| MAXIMUM CURRENT | 616 |

FIG 40.

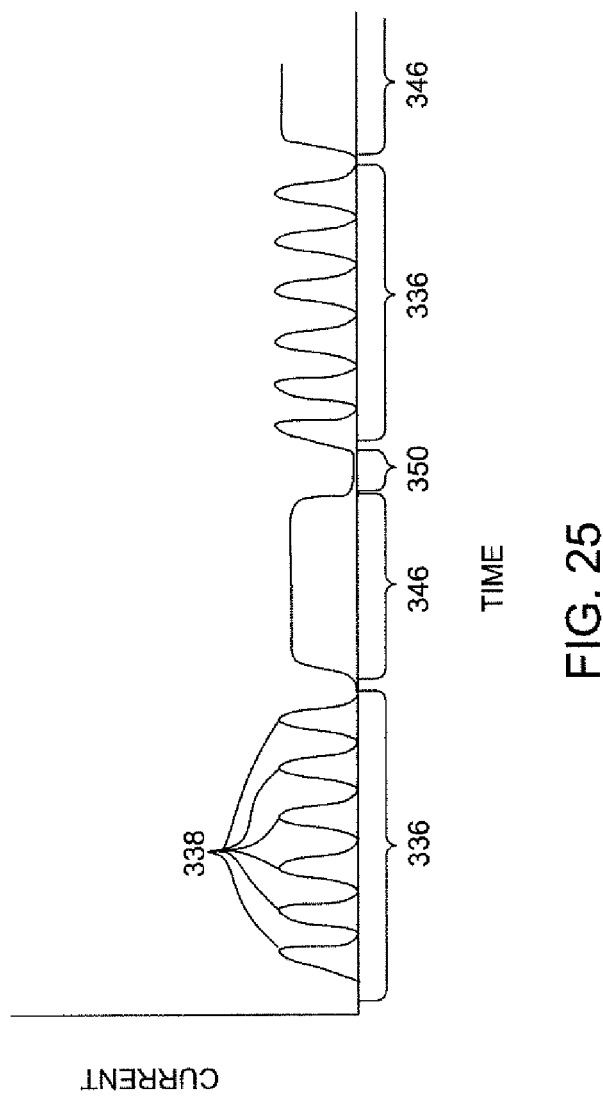

| | 72 |
|---|---|
| BEMF/IF SET POINT | 339 |
| M1 POS GAIN | 340 |
| M1 POS OFFSET | 342 |
| M1 NEG GAIN | 340 |
| M1 NEG OFFSET | 342 |
| M2 POS GAIN | 340 |
| M2 POS OFFSET | 342 |
| M2 NEG GAIN | 340 |
| M2 NEG OFFSET | 342 |
| M3 POS GAIN | 340 |
| M3 POS OFFSET | 342 |
| M3 NEG GAIN | 340 |
| M3 NEG OFFSET | 342 |
| BEMF/IF RVS ENGZTN SEUQNECE | 368 |
| IS SGNL PRFIL MODEL DATA | 370 |
| POWER SHARING | 540 |
| OSCILLATE TIME CVOMP. FACTOR | 665 |
| START UP TORQUE | 678 |
| START UP TORQU TIME OUT | 680 |

FIG. 27

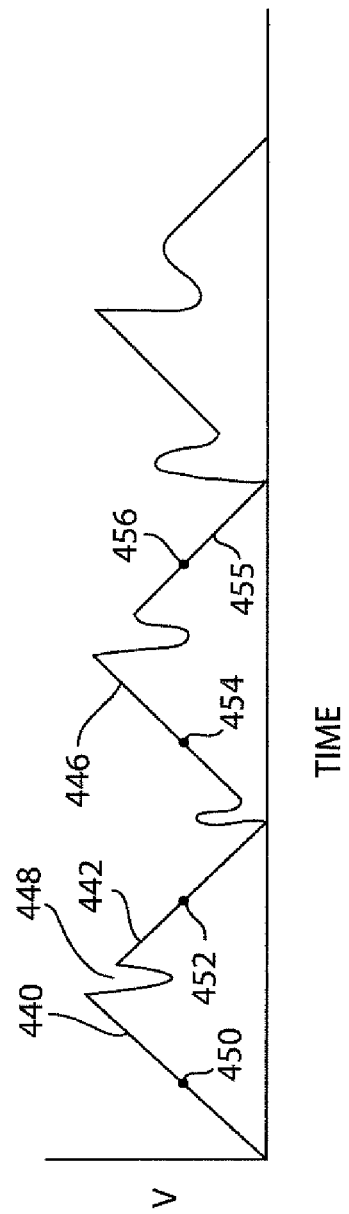
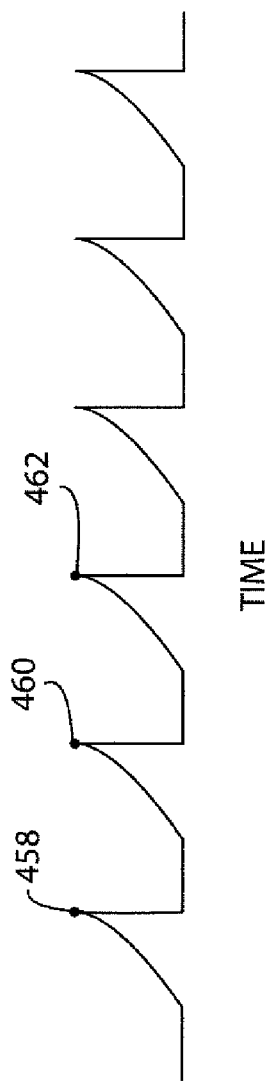

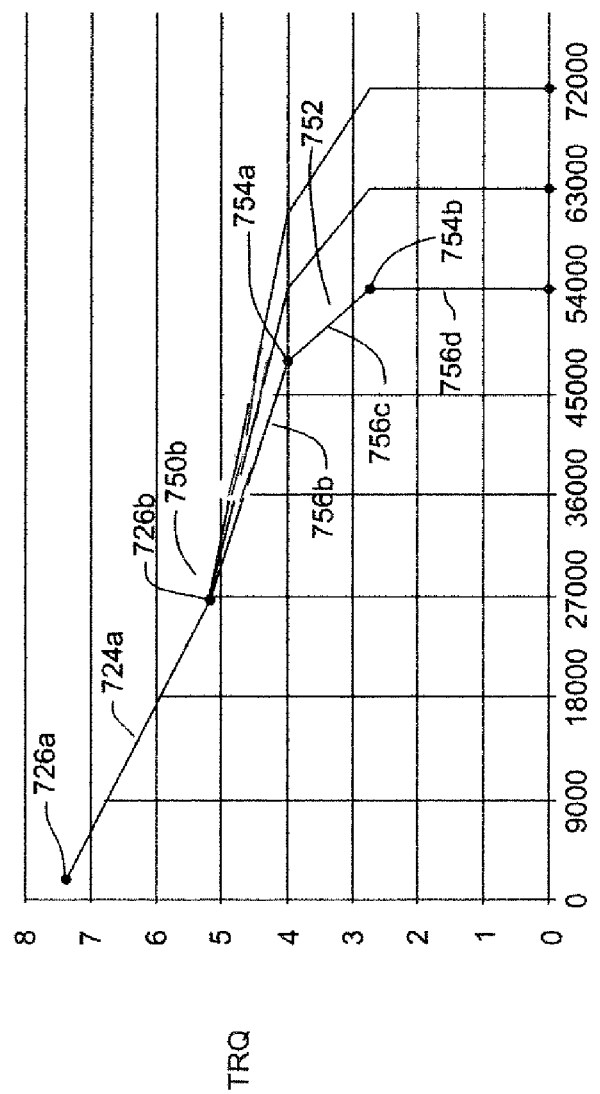

SURGICAL TOOL ASSEMBLY INCLUDING A CONSOLE, PLURAL SURGICAL TOOLS AND A FOOTSWITCH, WHEREIN THE CONSOLE IS ABLE TO CUSTOM MAP THE FOOTSWITCH TO EACH SURGICAL TOOL

RELATIONSHIP TO EARLIER FIELD APPLICATIONS

This application is a divisional of U.S. patent application Ser. No. 11/691,767 filed 27 Mar. 2007, now abandoned. Application Ser. No. 11/691,767 is a continuation of International Application PCT/US2006/034800, filed 28 Sep. 2005, now abandoned. International Application PCT/US2006/034800 claims priority from and is a continuation-in-part from U.S. patent application Ser. No. 10/955,381, filed 30 Sep. 2004, now U.S. Pat. No. 7,422,582. Patent application Ser. No. 10/955,381 claims priority from U.S. Prov. Pat. App. No. 60/614,089, filed 29 Sep. 2004, now expired. The contents of the above-identified applications are incorporated herein by reference.

FIELD OF THE INVENTION

This invention is related generally to a system for powering surgical tools. More particularly, this invention is related to a system for powering a motorized surgical tool based on the inductively sensed position of the motor rotor.

BACKGROUND OF THE INVENTION

In modern surgery, powered surgical tools are some of the most important instruments medical personnel have available to them for performing certain surgical procedures. Many surgical tools take the form of some type of motorized handpiece to which a cutting accessory like a drill bit, a bur or a saw blade is attached. These tools are used to selectively remove small sections of hard or soft tissue or to separate sections of tissue. The ability to use powered surgical tools on a patient has lessened the physical strain of physicians and other personnel when performing surgical procedures on a patient. Moreover, most surgical procedures can be performed more quickly and more accurately with powered surgical tools than with the manual equivalents that preceded them.

A typical powered surgical tool system, in addition to the handpiece, includes a control console and a cable that connects the handpiece to the console. The control console contains the electronic circuitry that converts the available line voltage into energization voltage suitable for powering the motor integral with the handpiece. Typically, the control console is connected to receive a signal from the hand or foot switch used to control the tool; based on that signal, the console sends appropriate energization signals to the handpiece so as to cause it to operate at the desired speed.

As the use of powered surgical tools has expanded, so has the development of different kinds of powered surgical tools that perform different surgical tasks. For example, a femoral reamer, used in hip replacement surgery is a relatively slow speed drill that operates at approximately 100 RPM, yet it draws a relatively high amount of power, approximately 400 Watts. Neurosurgery requires the use of a craniotome which is a very high powered drill that operates at approximately 75,000 RPM and that requires a medium amount of power, approximately 150 Watts. In ear, nose and throat surgery, micro drills are often employed. A typical micro drill rotates between approximately 10,000 and 40,000 RPM and requires only a relatively small amount of power, approximately 40 Watts.

As the number of different types of powered surgical tools have expanded, it has become necessary to provide each type of handpiece a mechanism for ensuring that it receives the appropriate energization signals. The conventional solution to this problem has been to provide each handpiece with its own power console. As can readily be understood, this solution is expensive in that it requires hospitals and other surgical facilities to keep a number of different consoles available, in the event a specific set of tools are required to perform a given surgical procedure. Moreover, in the event a number of different surgical tools are required in order to perform a given surgical procedure, it is necessary to provide the operating suite with the individual consoles required by the different handpieces. Having to provide these different consoles contributes to clutter in the operating suite.

An attempt to resolve this issue has been to design consoles that supply power to different handpieces. While these consoles have performed satisfactorily, they are not without their own disadvantages. Many of these consoles are arranged so that the medical personnel have to manually preset their internal electronics in order to ensure that they be provided the desired energization signals to the tools to which they are connected. Moreover, given the inevitable human error factor, time also needs to be spent to ensure that once configured for a new tool, a console is, in fact, properly configured. Requiring medical personnel to perform these tasks takes away from the time the personnel could be attending to the needs of the patient.

The Applicant's Assignee's U.S. Pat. No. 6,017,354, INTEGRATED SYSTEM FOR POWERED SURGICAL TOOLS, issued Jan. 25, 2000 the contents of which is explicitly incorporated herein by reference, appreciably eliminates the need to bring different control consoles into an operating room when surgical handpieces having different power requirements are used. In the disclosed system, each handpiece contains a NOVRAM. The NOVRAM stores data identifying the electrical power needs of the energy-producing component in the handpiece. The system includes a control console with a processor and an energization circuit for supplying energization signals applied to the handpiece. The types of energization signals the energization circuit supplies to the handpiece vary as a function of command signals sent by the processor. Upon the connection of a handpiece to the control console, the data in the handpiece NOVRAM are read. These data are then used by the processor to regulate the output of energization signals by the energization circuit so that the appropriate energization signals are supplied to the handpiece.

Still another feature of the prior art system is that it is possible to simultaneously connect plural handpieces to the control console. The processor simultaneously stores the energization signal-describing data for each connected handpiece.

Thus, the prior art system, for many surgical procedures, essentially eliminated the need to provide an operating room with plural control consoles just because the handpieces being used had different power requirements. Moreover, the above system was further designed so that the console could be used to sequentially energize different handpieces without first having to remove the first and handpiece and then install the second handpiece.

Clearly, the prior art system provided a number of different cost and time efficiencies to the operating room. However, this system can, at a given instant, only supply power to a single handpiece. There are instances wherein for efficiency or necessity it is desirable to simultaneously actuate plural handpieces during a surgical procedure. For example, sometimes one surgeon will be harvesting tissue from one portion of a patient while a second surgeon is preparing another portion of the patient's body for insertion of the tissue. The present system is not able to simultaneously power the two separate surgical handpieces used to perform these separate procedures. If, in the interest of efficiency, there is an interest in performing these procedures simultaneously, two separate control consoles must be provided.

Moreover, many surgeons use footswitches to control their surgical handpieces and accessory instruments, for example, irrigation and suction pumps. It is a common practice to provide, on a single footswitch assembly, a number of different footswitches for controlling a number of different functions. For example, a single footswitch assembly may have individual footswitches for controlling the on/off state of the handpiece motor, the speed of the handpiece motor, the forward/reverse/oscillate direction of the handpiece motor and whether or not irrigation fluid is to be supplied.

Another limitation associated with known systems for driving motorized surgical handpieces concerns their ability to control the associated handpieces when the motors are operating at low RPMs. This problem is especially prevalent in systems employed to drive handpieces that include brushless, sensorless DC motors. The known systems operate by monitoring the back electromotive force voltage (BEMF signal) produced at the unenergized winding of the motor. A limitation associated with this control technique is that, when the motor is operating at a low RPM, the BEMF signal is often so low that it is difficult, if not impossible, to measure. Once this signal is undetectable, it can be no longer user to regular the commutation of the windings. Instead, brut force means are often used when the motor is started up in order to initially actuate the rotor. Also, this typical means that once a motor stalls as result of the motor reaching limit as the amount of torque that it can develop, the surgeon must totally deactivate, turn off, the motor before, the complementary control console can again apply a commutation signal to the windings. This results in the undesirable slowing of the surgical procedure.

SUMMARY OF THE INVENTION

This invention is related to a new and useful surgical tool system. The surgical tool system of this invention includes a handpiece for actuating a cutting accessory. Internal to the handpiece is a brushless, sensorless motor. A control console selectively applies energization signals to the windings integral with the motor. The particular windings to which the current is supplied is a function of motor rotor position. At motor start-up and slow speeds, includes speeds down to stall speeds, the control console determines rotor position based on the inductance through the motor windings. In one version of the invention, this inductance sensing is performed by monitoring the current flow through the windings. Above a threshold speed, rotor position is determined based upon the back electromotive force developed across the windings.

BRIEF DESCRIPTION OF THE DRAWINGS

The invention is pointed out with particularity in the claims. The above and further features of the invention may be better understood by reference to the following description taken in conjunction with the accompanying drawings in which:

FIG. 17 is schematic representation of the stator windings of a handpiece motor;

FIG. 18 is a block and partial schematic diagram of the circuit used to monitor the power supply voltage;

FIG. 21 is a block diagram of the circuit used to convert a number of the monitored signals into digital signals;

FIG. 22 is a block diagram of the circuit used to convert the monitored current signal into a digital signal;

FIG. 23 is a block and partially schematic of one of the relay assemblies that for the motor multiplexer of the motor controller;

FIG. 24 depicts the records contained in the power driver assignment table;

FIG. 25 is a graph of current over time depicting the measured current of a handpiece motor when the system is an inductance sensing mode for the motor;

FIG. 27 depicts how a handpiece NOVRAM of the system of this invention includes gain and offset data to facilitate the inductive signal sensing of the handpiece rotor;

FIG. 34A is a graphic depiction of the BEMF signal over time and FIG. 34B depicts how, according the BEMF signal is measured according to this invention to determine motor rotor position.

FIG. 36 represents some of the data types stored by the power supply current limit module in order to perform selective power supply sharing;

FIG. 40 depicts some of the data stored in NOVRAM memory in order to regulate the application of energization signals to a transform;

FIGS. 49A and 49B are graphical representations of, respectively, first and second means of torque map scaling of this invention;

DETAILED DESCRIPTION

Figure 1:
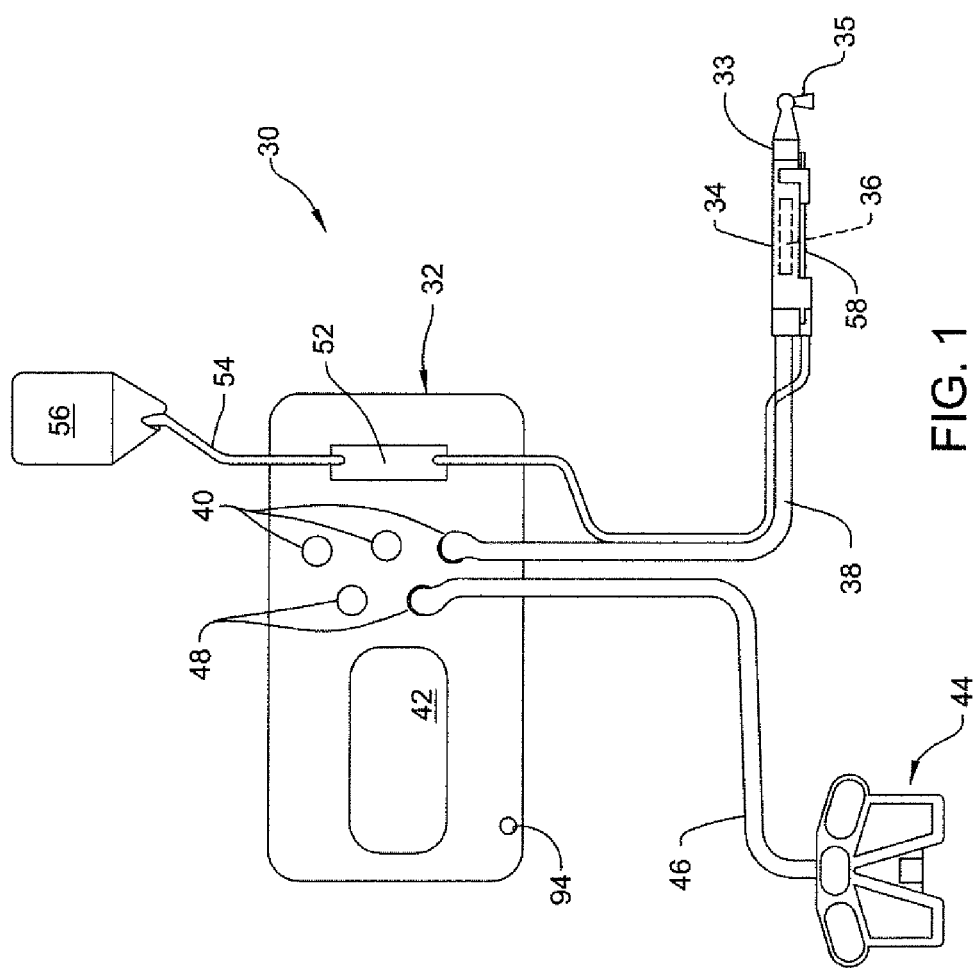
FIG. 1 depicts the basic components of the system of this invention.
Figure 2A:
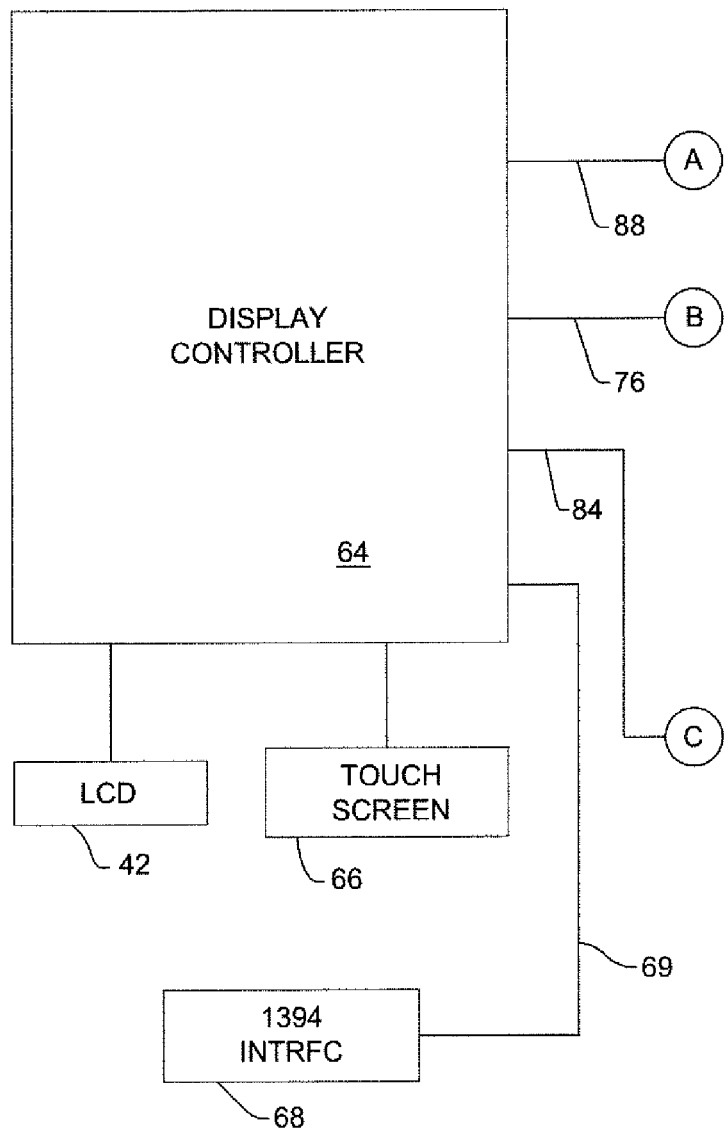
FIGS. 2A and 2B collectively form a block diagram of the major components internal to the control console of the system of this invention.
Figure 2B:
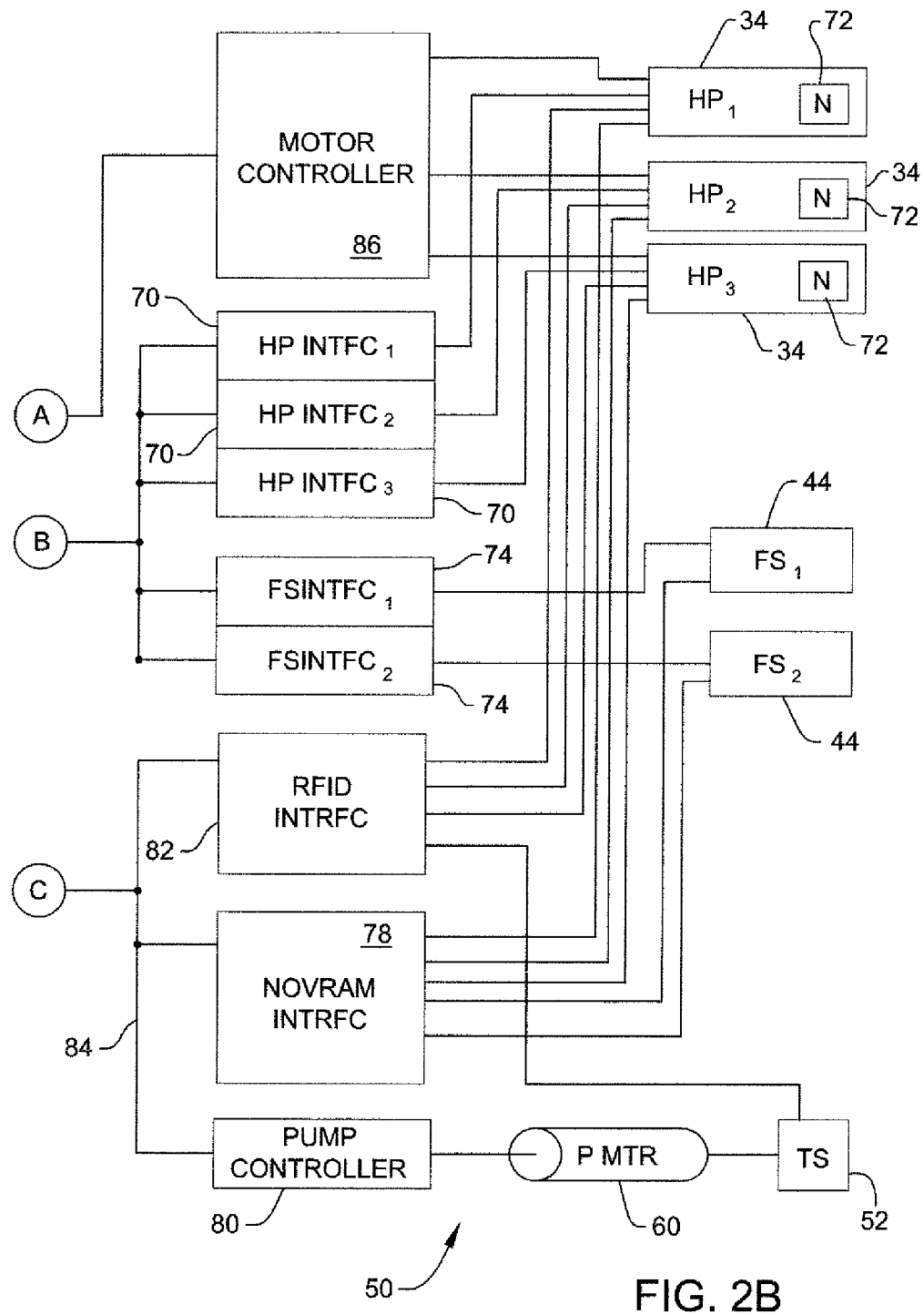

FIGS. 1, 2A and 2B illustrate the basic features of a surgical tool system 30 of this invention. System 30 includes a control console 32. The control console 32 is used to actuate one or more handpieces 34. In FIG. 1, a single handpiece 34, a saw, is illustrated. As seen by reference to FIG. 2B, it is possible to simultaneously connect three handpieces 34, to the control console 32. In the depicted version of the invention, internal to the handpiece 34 is a motor 36 (depicted as a phantom box) and a gear assembly (gear assembly not illustrated). Each handpiece 34 drives a cutting accessory 35 that is typically removably attached to the handpiece. In the illustrated handpiece 34 of FIG. 1, cutting accessory 35 is a saw blade that is removably attached to the distal end of the handpiece. ("Distal" means away from the surgeon/towards the patient. "Proximal" means towards the surgeon/away from the patient.) The illustrated handpiece 34 has a gear assembly designed to oscillate the saw blade back and forth. Other motorized handpieces 34 may be provided with other motor and gear assemblies to drive the associated cutting accessories in rotational movement. It is also recognized that a handpiece 34 typically has coupling assembly, represented by identification number 33 in FIG. 1, that releasably holds the cutting accessory 35 to the handpiece.

Each handpiece 34 is removably attached to a control console 32 by a flexible cable 38. The control console has multiple sockets 40. Each socket 40 is capable of receiving a separate cable 38. This allows the multiple handpieces 34 to simultaneously be connected to the control console 32.

Control console 32 has a display 42 with a touch screen surface. Commands for regulating the components of the system 30 are entered into the control console by depressing buttons presented as images on display 42. Commands are also entered into control console 16 by other control switches. These switches may be integral with the handpieces 34. Alternatively, these switches may be individual switches that are part of a footswitch assembly 44 also attached to the control console 32. In FIG. 1, a single footswitch assembly 44 is shown connected to the control console 32 by a cable 46. Control console 32 is provided with two sockets 48 for receiving two cables 46. This allows two footswitch assemblies 44a and 44b as seen in FIG. 2B to be simultaneously attached to the control console 16.

A pump 50 is also attached to the control console 32. Pump 50 includes a tube set 52 that is removably attached to the control console 32. Tube set 52 includes tubing 54 that provides a fluid path from a bag of irrigation fluid 56 to an irrigation clip 58 attached to the handpiece 34. Pump 50 also includes a motor 60 (FIG. 2B) disposed inside the control console 324.

FIGS. 2A and 2B, when assembled together, illustrate the main components internal to control console 30. These components include a display controller 64. Display controller 64 controls the output of images presented on display 42, represented as LCD (liquid crystal display) in FIG. 2A. The display controller 64 also serves as the overall controller for the control console 32. Thus, the display controller 64 receives the various input signals generated to control the operation of the equipment attached to the console 32, and causes the other components internal to the console to generate the appropriate output signals.

Display controller 64 is connected to a touch screen signal processor 66. The touch screen signal processor 66 monitors the depression of the touch screen layer over the display 28. Touch screen processor 66 upon detecting the depression of a portion of the touch screen layer, informs the display controller 64 of which section of the screen was depressed. Display controller 64 uses this information to determine which of the buttons presented on the display 42 was depressed.

Display controller 64 is also connected to a network interface 68, represented as the 1394 Interface in FIG. 2A. Network interface 68 serves as the device over which, by a network (not illustrated), the display controller 68 exchanges information about system 30 with other equipment used to facilitate the performance of the surgical procedure. One such piece of equipment may be a surgical navigation unit. When the control console 32 is connected to this type of component, display controller 64 informs the surgical navigation unit about the types of handpieces 34, 34, 34 that are connected to the control console and the specific types of cutting accessories attached to the individual handpieces. The surgical navigation unit uses the data to generate information displaying where, on or in the patient's body, the handpieces and cutting accessories are located.

Alternatively, the control console 30 may be connected to a voice recognition surgical control head. This type of device receives the surgeon's voice commands directing the operation of the surgical equipments. Examples of such commands are "Shaver, faster" and "Irrigation, on". In response to receipt of a specific spoken command, the voice recognition control head converts the command into a specific instruction packet. This packet is forwarded to the display controller 64 through the network interface 68.

Display controller 64 and network interface 68 exchange signals over a dedicated SPI bus 69.

Control console 32 also includes three handpiece interfaces 70. Each handpiece interface 70, is through a separate one of the sockets 40 and a cable 38 is connected to a separate one of the handpieces 34. Each handpiece interface 70 exchanges signals with components internal to the associated handpiece 34.

Components internal to a handpiece 34 that exchange signals with the handpiece interface 70 are sensors. For example, one handpiece may have a first sensor that monitors the temperature of the motor 36 internal to the handpiece. The same handpiece 34 may have a second sensor that generates an analog signal as function of the displacement of a switch lever on the handpiece. The output signal from this sensor represents the surgeon-selected speed for the handpiece motor 36. Another handpiece may have a sensor that generates a signal is a function of the open/closed state of valve that regulates irrigation flow through the handpiece. Based on the state of this valve, the display controller 64 may reset the speed of the pump motor 60 to increase/decrease the rate at which irrigation fluid is supplied to the handpiece 34.

Handpiece interface 70 is also capable of forwarding signals to components internal to the handpiece 34. For example, a handpiece may include a component that emits light, RF waves or an acoustic signal. The signal emitted by this device is used by the surgical navigation system to track the location of the handpiece. The energization signal for that actuates this component is transmitted from the control console 32 through the handpiece interface 70.

Control console 32 also includes two footswitch interfaces 74. Each footswitch interface 74, through a separate one of the sockets 48 and a cable 46, exchanges signals with a separate one of the footswitch assemblies 44. More particularly, each footswitch 44 includes one or more pressure sensitive sensors that generate signals in response to depression of a specific pad on the footswitch assembly. Each footswitch interface 74 reads the data from the footswitch sensors of the footswitch to which the interface is connected.

The handpiece interfaces 70 and footswitch interfaces 74 are connected to the display controller by a common first UART bus 76.

Control console 32 also includes a NOVRAM interface 78. The NOVRAM interface reads the data in memories internal to the handpieces 34 and footswitch assemblies 44. Specifically, internal to each handpiece 34 that exchanges signals with the handpiece interface is a NOVRAM 72. Each NOVRAM 72 contains data specific to the operation of the handpiece 34 to which the NOVRAM is mounted. Examples of such data include the minimum and maximum speeds at which the motor internal to the handpiece should develop, and the maximum torque the motor should produce at a given speed. The handpiece NOVRAMs 72 also contain data that identifies the type of sensors in the handpiece 34 and data that facilitates the processing of the output signals from the sensors. The above-referenced U.S. Pat. No. 6,017,354, which is incorporated herein by reference, offers a more detailed list of types of data stored in the NOVRAM 72.

While not illustrated, it should be understood that each handpiece also contains an EEPROM. NOVRAM interface 78 is capable of reading data from and writing data to the handpiece EEPROMs. The data written to the handpiece EEPROMs include data indicating elapsed time the handpiece 34 has been actuated and data identifying any faults detected during the operation of the handpiece.

Each footswitch assembly 44 also contains a NOVRAM (footswitch assembly NOVRAMs not illustrated). Each footswitch NOVRAM contains data describing the configuration of the associated footswitch assembly 44 and data useful for processing the signals generated by the sensors internal to the assembly.

A pump controller 80 is also incorporated into the control console 34. Pump controller 80, in response to commands from the display controller 64, regulates the on/off actuation of the pump motor 60. The pump controller 80 also regulates the speed at which the pump motor 60 is actuated so as to regulate the rate at which irrigation fluid is discharged from pump 50. In one version of the invention, the primary component about which the circuit forming the pump controller 80 is constructed is the ATmega8 microcontroller available from Atmel Corporation of San Jose, Calif., USA.

Control console 32 also has an RFID interface 82. The RFID interface 32 exchanges signals with any radio frequency identification devices (RFIDs) that are connected to the control console 32 (RFIDs not illustrated). Each RFID contains a memory and a circuit that facilitates the reading of data from and writing of data to the memory. Each cutting accessory 35 attached to an individual handpiece 34 may have an RFID. Each RFID integral with a cutting accessory 35 contains data describing the characteristics of the cutting accessory. These data may describe the physical characteristics of the cutting accessory and/or the speed and direction at which the cutting accessory should be driven. The Applicant's U.S. patent application Ser. No. 10/214,937, SURGICAL TOOL SYSTEM WITH COMPONENTS THAT PERFORM INDUCTIVE SIGNAL TRANSFER, filed Aug. 8, 2002, U.S. Patent Publication No. US 2003/0093103 A1 which is explicitly incorporated herein by reference, provides a detailed instruction of how data in a cutting accessory RFID is used to regulate the actuation of the handpiece 34 to which the cutting accessory 35 is attached.

An RFID may also be attached to either the tube set 52 of the pump 50 or the bag 56 holding the pumped irrigation fluid. The data in the tube set RFID describes the characteristics of the tube set 52. The data in the bag RFID describes the characteristics of the contents of the bag 56. The Applicant's U.S. patent application Ser. No. 10/952,410, SURGICAL TOOL SYSTEM WITH INTEGRATED PUMP, filed 28 Sep. 2004, U.S. Patent Publication No. US 2006/0073048 A1, which is explicitly incorporated herein by reference, provides a detailed explanation of how the data in the RFIDs within a tube set 52 and a fluid bag 56 are used to regulate the actuation of the pump 50.

The RFID interface 82 reads the data from and writes data to the cutting accessory, tube set and fluid bag RFIDs. Signals are transferred between the RFID interface 82 and the individual RFIDs by inductive signals transfer. Not shown are the coils in the control console 32 that facilitate signal transfer between the tube set 52 and fluid bag 56 RFIDs. Similarly not shown are the coils internal to the handpieces 34 that facilitate the signal exchange between the control console 32 and the cutting accessories 35 attached to the handpieces. RFID interface 82 is constructed out of one or more SL RC400 I•CODE Readers available from Philips Semiconductors of Eindhoven, The Netherlands.

The NOVRAM interface 78, the pump controller 80 and the RFID interface 82, forward data to and receive instructions from the display controller 64 over a second UART bus 84

Control console 32 also includes a motor controller 86. Motor controller 86 is the circuit that, based on instructions from the display controller 64, generates the energization signals to the motors 36 other power-consuming units internal to the handpiece 34. Motor controller 86 is simultaneously connected to the three handpieces through the sockets 40 and cables 38. The motor controller 86 provides data and receives instructions from the display controller 64 over a second SPI bus 88.

Figure 3:
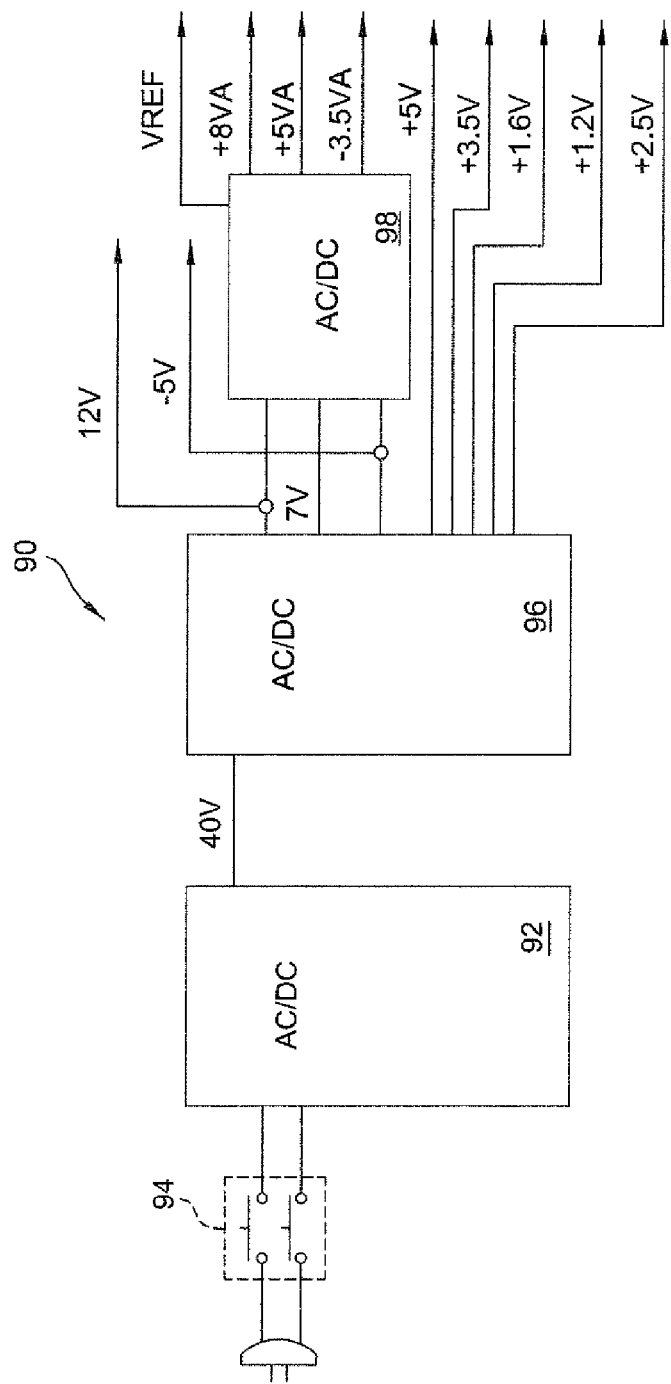
FIG. 3 is a block diagram of the sub-circuits internal to the power supply of the control console.

As seen by reference to FIG. 3, also internal to the control console is a power supply 90. Power supply 90 includes an AC to DC converter 82. The AC/DC converter 92 converts the line signal into a 40 VDC signal. This 40 VDC is the signal applied to the handpiece 34 by motor controller 86. The signal flow of the line voltage into the AC/DC converter is controlled by a single pull double throw switch 94. Switch 94 thus functions as the main on/off switch for the control console 94. Internal to the AC/DC converter are a series of chokes that filter the line signal and a bridge rectifier that converts and filters the line signal into a DC voltage. A UCC38500 power manager available from Texas Instruments of Dallas, Tex., is used to perform power factor correction of the output signal. A boosted DC signal, at 380V, is then pulse wave modulated across a step down transfer. The output signal from the transformer is rectified and filtered to produce the 40 VDC output signal. In order to reduce the complexity of the drawings, unless necessary, the buses along which the 40 VDC signal and the other output signals produced by power supply 40 are not shown.

In addition to being applied to the handpieces 34, the 40 VDC is also applied to a digital power supply 96 also part of the power supply 90. The power supply 96, components not illustrated, converts the 40 VDC signal into a 12 VDC, 7 VDC, 5 VDC, 3.3 VDC, 2.5 VDC 1.8 VDC 1.26 VDC and −5 VDC signals. All of the above signals but the 7 VDC signal are made available on buses for use by other components internal to the control console 32.

The 12 VDC, 7 VDC and −5 VDC signals produced power supply 96 are forwarded to an analog power supply 98, also part of power supply 90. Based on the input signals, power supply 98 produces 8 V, 5 V and −3.5 V precision, constant analog signals. The analog signals produced by converter 98 are used by sensing circuits internal to the control console 32. Power supply 98 also produced a VREF signal. Typically the VREF signal is 2.5 Volts.

Figure 4:
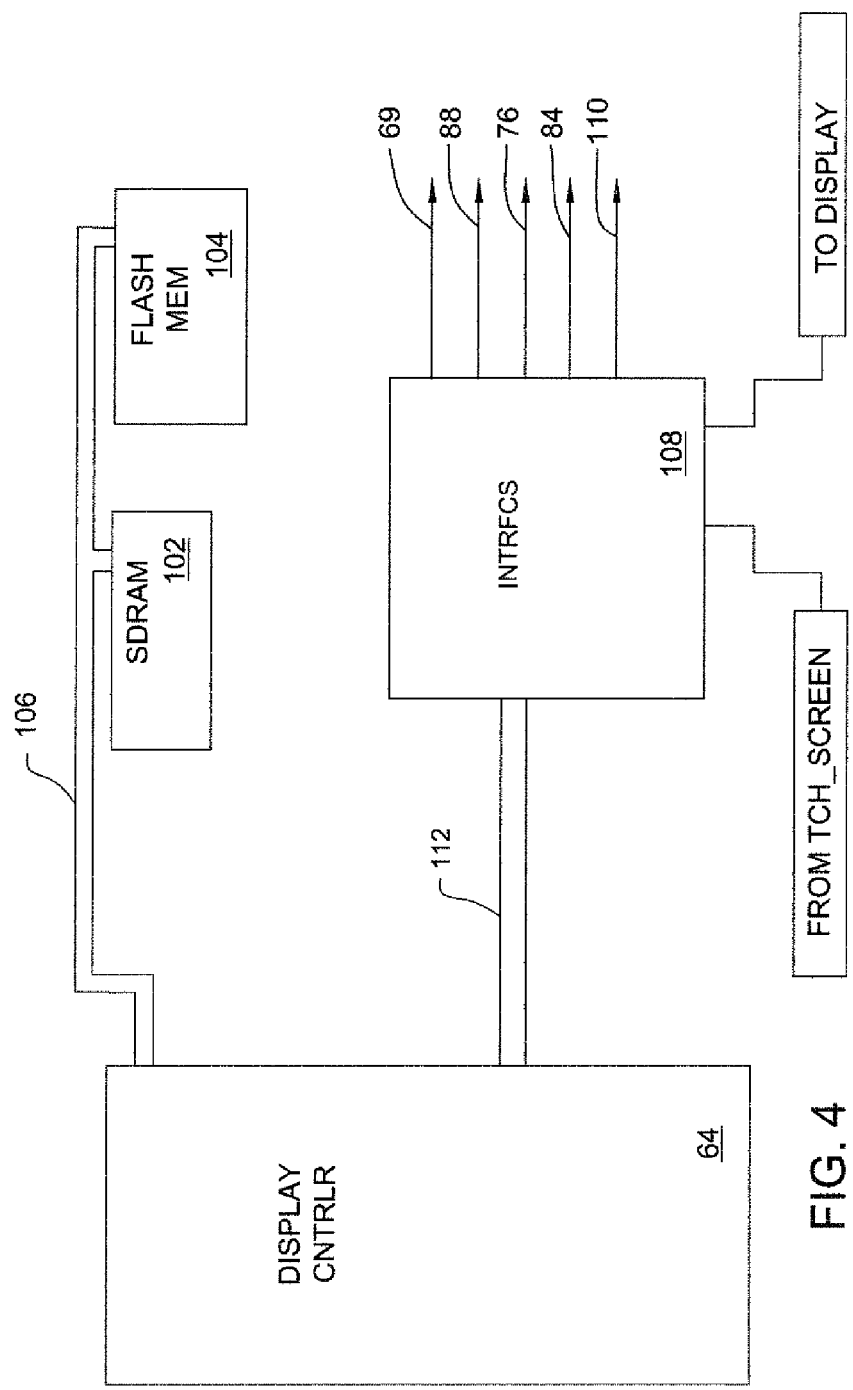
FIG. 4 is a block diagram of the display controller and the components peripheral to the display controller.

Display controller 64 and the components peripheral to it are now described by reference to FIG. 4. The display controller 64 is any suitable microprocessor. One potential microprocessor is the GDPXA255A0C300 processor from the Intel Corporation of Santa Clara, Calif. Both SDRAM 102 and a flash memory 104 are connected to the display controller 64. The SDRAM 102 holds operating instructions and data for run time use by the display controller 64. Flash memory 104 is a non-volatile memory that stores the permanent operating instructions for the display controller 64 and calibration data for touch screen 66. The SDRAM 102 and flash memory 104 are connected to the display controller 64 by a common bus 106.

A collection of sub-circuits, broadly referred to as interface 108, are also connected to display controller 64. Internal to interface 108 are the individual sub-circuits that control the exchange of signals between the display controller 64 and the buses internal to the other components within control console 32. These sub-circuits include the circuits that facilitate the exchange of signals over the two SPI buses 69 and 88, the UART buses 76 and 84 and with the display 42 and touch screen signal processor 66. Interface 108 also includes a circuit for facilitating signal exchange over a USB bus 110 internal to the control console 32.

Signals are exchanged between display controller 64 and the sub-circuits forming interface 108 over a collection of conductors generally identified as bus 112. It should be recognized that the exchange of signals between the display controller and the individual sub-circuits forming interface 108 is, between the sub-circuits, asynchronous.

A number of additional peripheral devices, while not illustrated should further be understood to be connected to display controller 64. These parts include a crystal that provides a clock signal to the display controller 64. There are circuits that provide a stable power supply and short life back-up power supply to the display controller 64 and the sub-circuits forming interface 108.

When system 10 of this invention is initially set up to run, display controller 64 reads the data in the handpiece NOVRAMs 72, the footswitch assembly NOVRAMs, and the RFIDs' internal to the cutting accessories 35 and the pump tube set 52. Based on these data as well as any additional data entered by the operating room personal, the system is configured for operation. For example, absent any additional instructions, based on the data received from a handpiece NOVRAM 72 and the RFID of the complementary cutting accessory 35 attached to the handpiece, display console 64 establishes for the handpiece the speed range in which its motor 36 should operate and preferred or default speed. This latter speed is the initial operating speed of the motor if it is operated at single speed. Display controller 64 also causes to be presented on display 42 an image that identifies the handpiece and cutting accessory combination.

Based on data read from the footswitch assembly NOVRAM, display controller 64 determines what correction factors need to be provided to the analog input signals generated by the sensors internal to the assembly. Based on data from the RFID internal to the pump tube set 52, the display controller 64 establishes the speed at which the pump motor 62 should run in order to discharge irrigation fluid at a specified flow rate.

Once the system 10 is configured for operation, surgeons actuate the various components, i.e., the handpieces 34 and pump 50 by entering commands into the control console 32. These commands may be entered by depressing pedals on the footswitch assemblies 44 or by depressing control buttons on the handpieces 34 or that are presented on display 42. Spoken commands may also be entered with a voice recognition surgical control head through network interface 68. Based on these commands, display controller 64 sends specific commands to the components internal to the control console. Primarily, these commands are sent to motor controller 86 to actuate one or more of the handpieces 34. Some commands are sent to the pump controller 80 to actuate the pump motor 60.

Figure 5:
FIG. 5 depicts the records contained within an exemplary procedure preference file.

Internal to flash memory 104 associated with the display controller 64 are a number of procedure preference files 116, one of which is now described by reference to FIG. 5. Each procedure preference file 116 indicates how, as an alternative to the default settings, one or more components of the system 10 are to be configured for operation during a specific surgical procedure. Each procedure preference file 116 contains one or more component preference fields 118. Each preference field contains two sub-fields, (not identified). The first sub field includes data identifying the component to be configured; the second sub field identifies how the component is to be configured.

In the illustrated preference file 116, the first component preference field 118 contains data indicating that the preferred setting, the initial setting for the speed of a universal drill handpiece is to be set at rate different than the default setting in the handpiece NOVRAM 72. The second component preference field 118 contains data indicating the maximum speed for the universal drill handpiece is to be set at a rate different than the rated maximum speed specified by NOVRAM 72. (This alternative maximum speed is less than the rated maximum speed.) The third component preference field 118 contains data indicating whether or not the pump 50 is to be actuated when the handpiece 34 is actuated. Data regarding the preferred flow rate at which the pump 50 is to be actuated are stored in the fourth component preference field 118. The fifth component preference field 118 contains data regarding which individual footswitch pedals should be mapped to control the operation of the handpiece 34 and pump 50.

Figure 6:
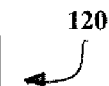
FIG. 6 depicts the records contained within an exemplary master users directory.

Preference files 116 may be established for specific procedures, for specific surgeons and for specific procedures performed by specific surgeons. Specifically, as seen by reference to FIG. 6, display controller 64 stores in memory a master user directory 122. User directory 122 includes a number of user fields 124 each of which contains data that identifies a specific individual surgeon or procedure. The first two and fifth user fields 124 of FIG. 6 identify specific surgeons. The third and fourth user fields 124 identify specific procedures.

Figure 7:
FIG. 7 depicts the records contained within an exemplary preference directory.

Each user field 124 links to a specific preference directory 126, described with reference to FIG. 7. The depicted preference directory 126 is for a specific doctor. Internal to the preference directory 126 are preference fields 128 that identify the procedures for which this doctor has certain instrument preferences. Each preference field thus contains data identifying a procedure for which the doctor has established a preference and data identifying the specific preference file 116 for that procedure. The preference directory 126 for a procedure identifies the system settings individual surgeons have for the procedure. Each preference field 128 within the directory thus identifies both the doctor and contains a pointer to that doctor's specific preference file 116 for the procedure.

Figure 8:
FIG. 8 is an example of the records contained within the active preference table.

Display controller 64 of this invention also maintains an active preference table 130, described by reference to FIG. 8. Active preference table 130 contains records of four system setting preferences it is system setting preference is stored in a separate active preference file 132. Each active preference file 132 identifies the specific active preference and contains a pointer to the specific preference file 116. The selective active setting preferences can be set on as needed basis.

Figure 9:
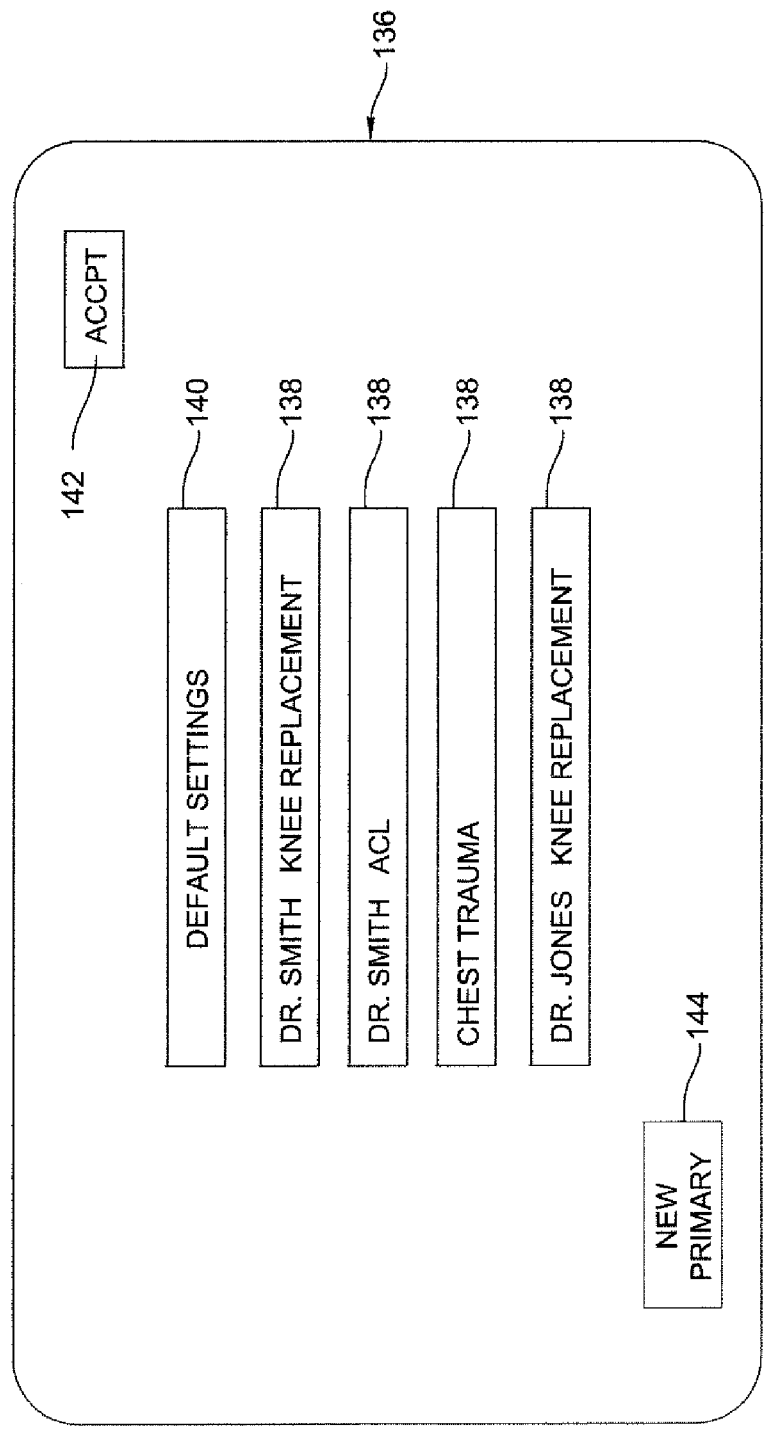
FIG. 9 depicts the image presented on the display to invite the selection of an active preference.

When the system is set to run, operating personnel can relatively easily access an active preferences image 136 on display 42 now described by reference to FIG. 9. The active preferences image 136 includes four bars 138 on which the active preferences stored in table 130 are listed. Also presented is a default bar 140. The operating room personnel can then press one of the bars 138 or 140 to select a particular preference. Confirmation of the acceptance is performed by depressing the accept (ACCPT) button 142. Once the selected setting preference is confirmed, display controller 64 configures the system according to the data in the file 116 for the selected preference.

Alternatively, selection and confirmation of the default setting results in the display controller 64 configuring the system based on the default settings for the handpieces 34 and cutting accessories 35.

Replacement of one of the active preferences is initiated by selecting the preference and depressing the NEW PRIMARY button 144.

An advantage of the above feature of the system 10 of this invention is that it eliminates the need, for commonly used system configurations, to have to go through a longer multi-step selection process to retrieve the data in a specific preference file 118.

Figure 10:
FIG. 10 is a table illustrating the data fields within footswitch assignment table.

System 30 of this invention is further configured so that either footswitch assembly 44 can be used to control any one of the handpieces 34 connected to the control console 32. In order for system 30 to perform this function, it should be understood that the display controller 64 maintains a table 150, illustrated by FIG. 10, for each footswitch assembly 44. The individual fields 152 in table identify the control function assigned to a separate one of the pedals integral with the footswitch assembly. In the depicted version of the invention, footswitch assembly has five pedals. Therefore, table 150 for the footswitch assembly has five pedal assignment fields 152. Display controller 64 writes data identifying the function assigned to each footswitch pedal into its complementary assignment field 152 based on either entered established default settings, manually entered preference commands or data regarding an individual surgeon's preference that are retrieved from storage.

When a signal is received from one of the footswitch sensors indicating the complementary pedal has been actuated, display controller 64, based on reference to the data in table 150 for the footswitch, generates the appropriate command to cause the appropriate state change of the other component connected to the system.

Display controller 64 also updates the data in the footswitch function tables to facilitate the switching of control of the handpieces to between the footswitches as discussed below.

Specifically, the display controller 64 monitors whether or not a handpiece cable 38 is connected to each socket 40 and whether or not a footswitch cable 46 is connected to each socket 48. It is assumed that if a cable 38 is connected to a socket 40, a handpiece 34 is connected to the distal end of the cable 38. Each footswitch assembly 44 is integrally attached to a cable 46. Therefore, the connection of a cable 38 to the control console automatically results in the connection of a footswitch to the console.

Figure 11:
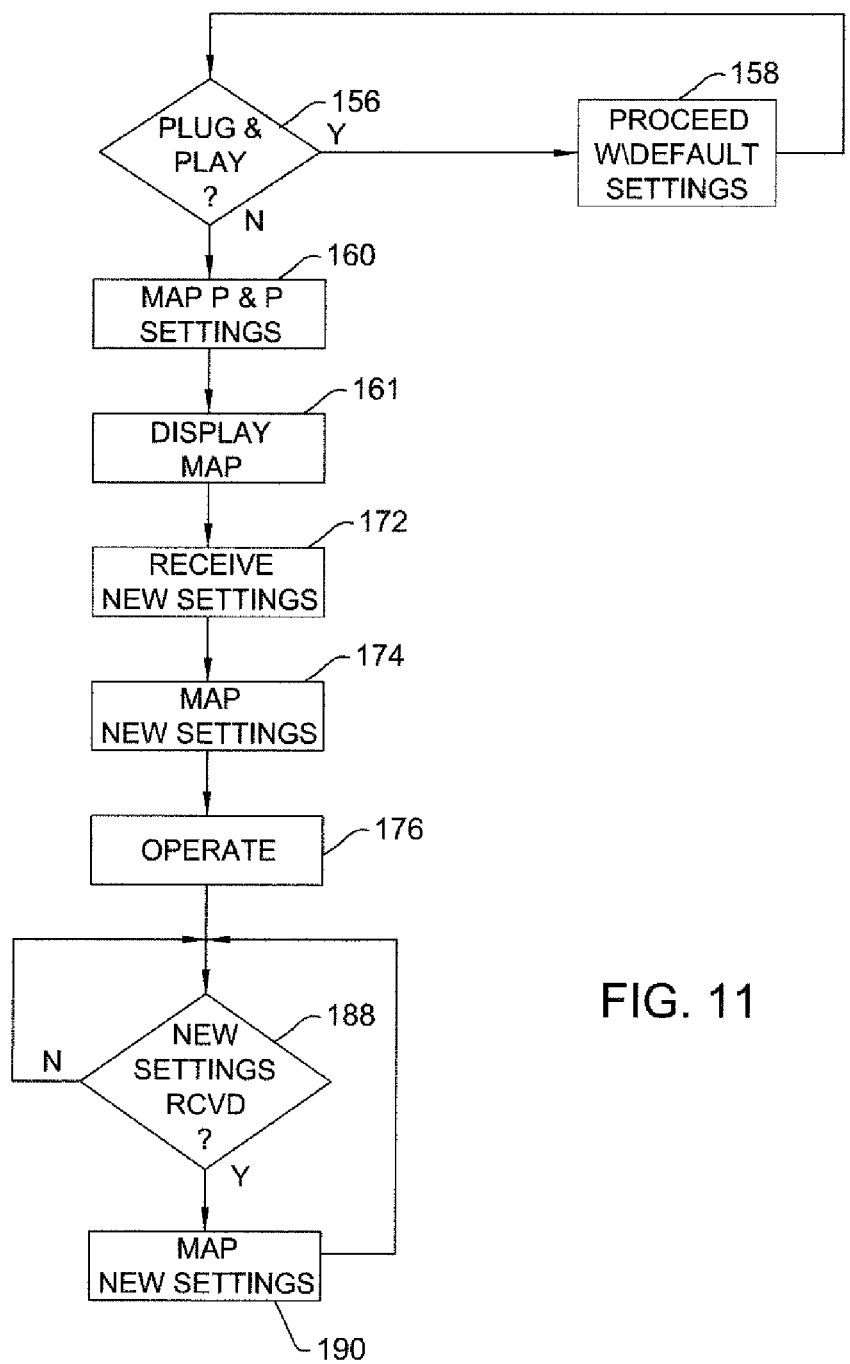
FIG. 11 is a flow chart of the basic process steps used by the control console to assign the footswitches control of the handpieces coupled to the control console.

As represented by step 156 in the flow chart of FIG. 11, the initial monitoring of the handpiece 34 and footswitch 44 connections to the control console 32 is referred to as monitoring whether or not the system 30 is in the plug and play mode. System 30 is considered in the plug and play mode if, at a given time less than two handpieces 34 or less than two footswitch assemblies 44 are connected to the control console 32.

If the system is in the plug and play mode, display controller 64, in step 158, assigns that handpieces to the footswitches according to a default scheme. Specifically under this scheme, if there is just a single footswitch assembly 44 attached to the control console 32, the control of each attached handpiece 34 is assigned, or mapped, to that footswitch. Thus, for each attached handpiece 34, display controller 64 writes to the pedal assignment table 150 for the footswitch assembly 44 data in one of the function fields 152. These data indicate that the footswitch pedal associated with the function field 152 controls the specific handpiece.

Similarly, the system 30 is considered in the plug and play mode when there are plural footswitch assemblies 44 and a single handpiece 34 attached to the control console 32. Display controller 64 performs default mapping for this version of the plug and play mode by mapping control for the handpiece to each footswitch assembly. Thus the display controller 64 writes into the pedal assignment tables 150 for both handpieces data indicating that each footswitch can control the handpiece 34. When both footswitches can control a handpiece, the handpiece is considered to be in the below discussed dual-control state.

If, as a result of the cable connection monitoring of step 156, display controller 64 determines that two or more handpieces 34 and both footswitch assemblies 44 are connected to the control console 32, the system is considered to be in the multiples mode. Initially, when the system 30 enters the multiples mode, display controller 64 maps the footswitch assignments to what they were in the immediate past plug and play mode, step 162. Thus, if a single footswitch assembly 44 was controlling the plural handpieces, that footswitch assembly initially retains control of those handpieces. If both footswitch assemblies had a single handpiece under dual control, both footswitch assemblies maintain this control.

Figure 12:
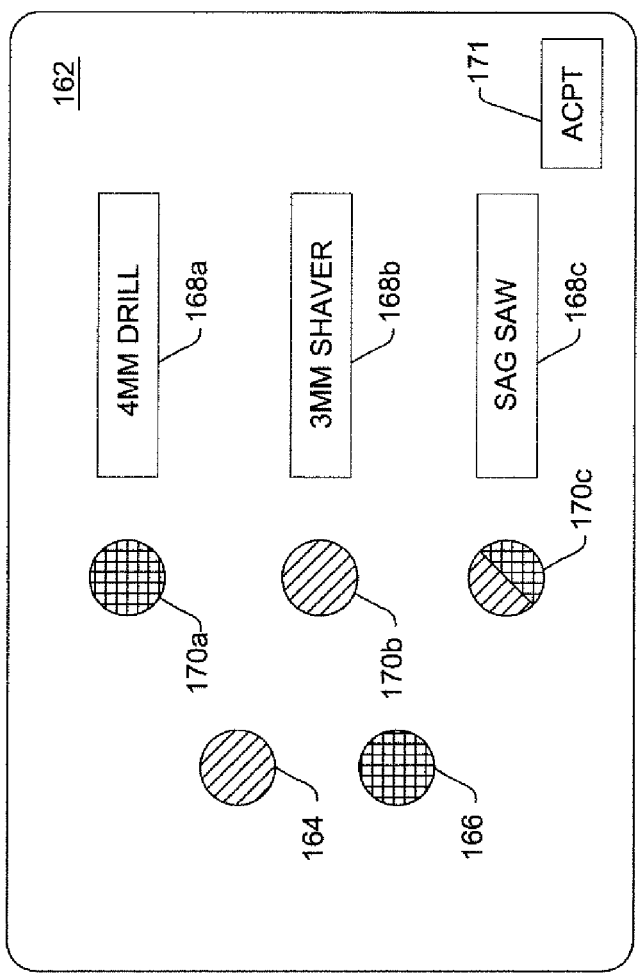
FIG. 12 is a diagram depicting a basic footswitch mapping image that is presented on the control console display.

After the mapping of step 160 is complete, display controller 64, in step 161, causes a footswitch assignment map 162 to be presented on the display 42, as illustrated by FIG. 12. On map 162, each footswitch assembly is represented by a different color button on the left side of the image. In the displayed map a green button 164 is used to represent a first footswitch assembly; a yellow button 166 represents the second footswitch assembly. Legends 168*a*, 168*b* and 168*c* identify each handpiece connected to the control console 34. The data identifying each handpiece so this information can be presented in map 162 is from the handpiece NOVRAMs 72.

Also present on the image of map 162 are color-specific buttons 170*a*, 170*b* and 170*c* that identify to which footswitch assembly 44 each handpiece is presently assigned. Each button 170*a*, 170*b* and 170*c* is immediately to the right of the legend image 168*a*, 168*b* and 168*c*, respectively, of the handpiece with which the button is associated. The color of each button 170*a*, 170*b* and 170*c* corresponds to the color associated with the footswitch assembly 44 presently mapped to control the button's handpiece. Map image 162 of FIG. 12 indicates that the 4 mm drill is under the control of the yellow footswitch assembly, the footswitch assembly connected to the bottom of the two sockets 48.

As represented by button 170*c* of map 12, a handpiece being under dual control is shown by its associated button being half one color and half the second color.

The surgeon then indicates what footswitch assignments are wanted for the present operation, step 172 of FIG. 11. This step is performed by depressing the touch screen image of each legend 168*a*, 168*b* or 168*c* of each handpiece 34 that is to be mapped to a new footswitch assembly 44. Upon each depression of the legend image, display controller 64 changes the footswitch mapping for the handpiece. Specifically, the display controller cycles the mapping through the following sequence: footswitch assembly associated with upper socket 48; footswitch assembly associated with lower socket 48; dual control mode; and no footswitch control. As the mapping changes, the color of the button 170*a*, 170*b*, or 170*c* changes appropriately to indicate the new assignment for the associated handpiece.

As mentioned above, it is possible to separate a handpiece 34 from footswitch control. This option may be selected for example, when the surgeon chooses to use a handpiece mounted switch to regulate the actuation of the handpiece 34. When this option is selected, the associated button 170*a*, 170*b* or 170*c* on map 162 is presented as a grey. Acceptance of specific footswitch assembly assignment map is performed depressing the image of the accept (ACPT) button A23 also presented of the image of map 162.

It should be understood that the footswitch assignment mapping can only be performed by pressing buttons presented on display 42. This prevents inadvertent depression of the footswitch pedals for unintentionally serving to transfer control of a handpiece 34 from one footswitch assembly 44 to the second footswitch assembly 44.

In response to the surgeon performing step 172, display controller, in step 174 maps the new footswitch assignments into the footswitch assignment tables 150. The surgeon(s) is(are) then able to use actuate each handpiece 34 by depressing the appropriate pedal on the footswitch assembly 44 assigned to control that handpiece, step 176.

Figure 13:
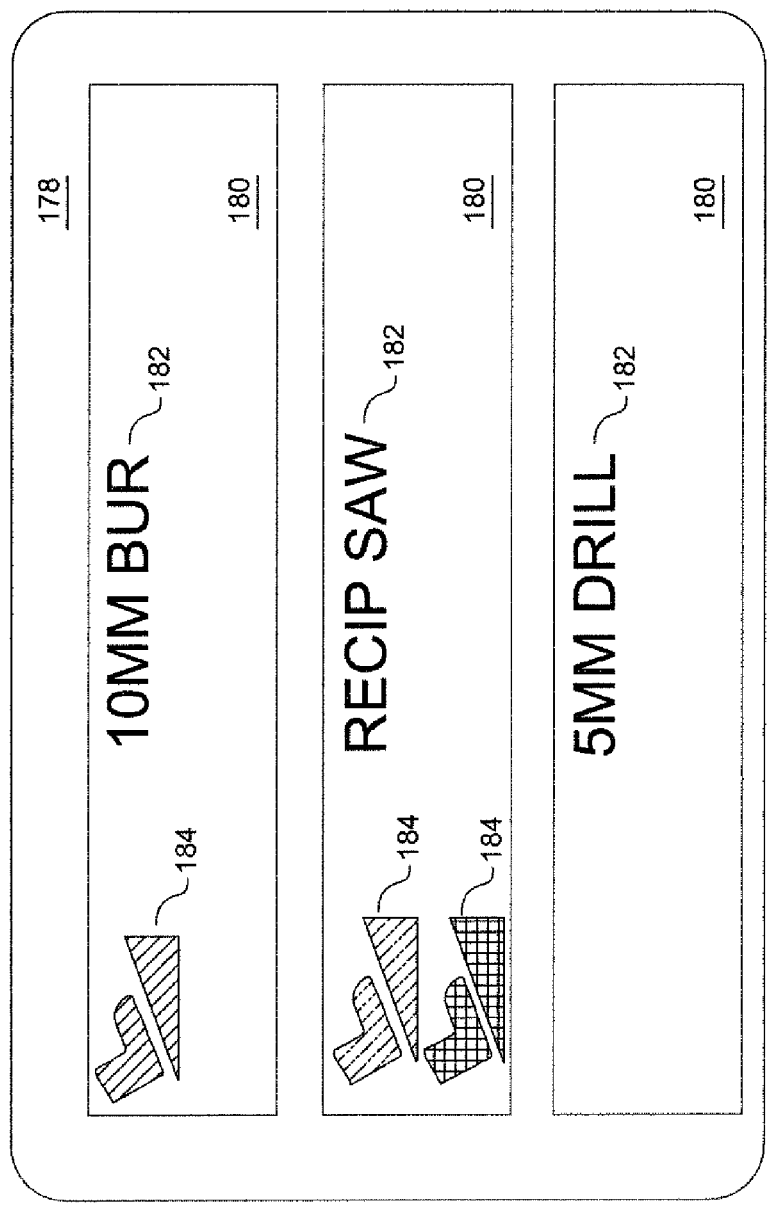
FIG. 13 is a diagram depicting components of the run time image presented on the control console display.

In order to allow operating room personnel to readily keep track of which, if any, footswitch assembly 44 controls a specific handpiece 34, information about this relationship is presented on the run time display 178, depicted in FIG. 13. Specifically, a bar 180 is presented for each handpiece connected to control console. Integral with each bar 180 is a legend 182 that identifies the handpiece. On the left side of the bar 180 a footswitch icon 184 appears if the handpiece is under footswitch control. The color of the icon 184 identifies the footswitch assembly 44 controlling the handpiece 34. In FIG. 13, a green icon 184 is presented with the 10 mm bur bar 180. This means the green footswitch assembly 44 controls this instrument. Both a green icon 184 and a yellow icon 184 are presented with the bar associated with the reciprocating saw bar 180. This means that this instrument is in the below described dual control mode. However, one icon 184 is displayed at full brightness, here the yellow icon; the second icon, here the green icon 184, is displayed at reduced brightness (represented by the phantom presentation). This means that at, the present instant, the yellow footswitch assembly has control of the saw.

In FIG. 13 there is no footswitch icon within the 5 mm drill bar 180. This serves as indication this handpiece 34 is not under the control of either footswitch assembly 44.

Once the desired footswitch assembly 44 assignment maps have been entered into the control console 32, the surgeons can then perform the procedure, represented by step 176.

During the course of a surgical procedure, there may be movement of the surgeons, handing off of the handpieces 34 between surgeons or movement of the footswitch assemblies 44. As a result of any one of these events, there may be confusion regarding which surgeon is using which footswitch assembly 44 to control which handpiece 34. If this confusion arises, surgeons can easily place the handpieces in an up position, away from the patient, and actuate each handpiece. As each handpiece is actuated, the run time image changes to show which handpiece is running. This provides the surgeons with a quick means to determine which footswitch assembly 44 is controlling which handpiece 34.

Once the operation begins, the map assignments for the footswitch assemblies 44 may be changed as represented by step 188. Specifically, by depressing other buttons presented on display 42, it is possible to have display controller 64 represent the image of the footswitch assignment map 162. The new footswitch assembly 44 assignments are then entered. These assignments are then mapped into the footswitch assignment tables 150, step 190. System 10, with the new footswitch assemblies' assignments, is again available for use.

Figure 14:
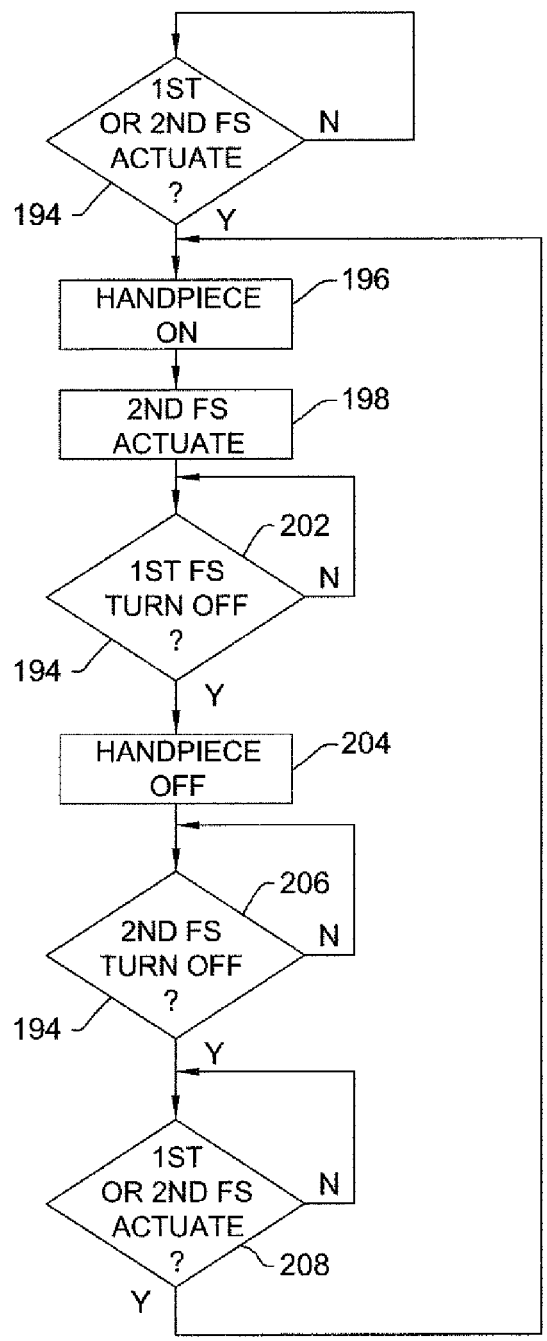
FIG. 14 is a flow chart of the process steps performed by the control console when a handpiece is placed in the dual control mode.

As mentioned above whether the system is in either the plug and play mode or the multiples mode, there may be a situation when one or more of the handpieces 34 are placed in the dual control mode. When a handpiece 34 is in this mode, the depression of an assigned foot pedal on either footswitch assembly 44 will actuate the handpiece. When a handpiece 34 is in this mode, display controller 64 executes the process steps of FIG. 14 to prevent both footswitch assemblies 44 from simultaneously controlling the handpiece. Initially as represented by step 194, display controller 64 monitors the output signals from both footswitch assemblies 44 to determine if either assembly actuates a handpiece under dual control.

If, in step 194, an actuation signal is received from either footswitch assembly 44, display controller 64 instructs motor controller 86 to actuate the handpiece, step 196. Also in step 196, the run time display A26 is changed so as to brighten the image of the icon 184 associated with the activating footswitch assembly 44.

The surgeon using the actuating footswitch assembly 44 may then press the pedals so as to instruct the control console 32 to turn off the handpiece 34. If this event occurs, the display controller causes the handpiece to be deactivated. The display controller 64 returns to step 194. (Above steps not shown.)

However, during step 196, the surgeon operating the second footswitch assembly 44 may attempt to turn the handpiece on, as represented by step 198. Display controller 64 ignores this signal. Instead, as represented by step 202, display controller waits to receive from the first footswitch assembly signals indicating the handpiece is to be turned off. Upon receipt of this signal, in step 204, display controller 64 turns of the handpiece. Display controller 64 takes this action even though the second footswitch assembly is still generating a command calling for the handpiece to be actuated. Also as part of step 204, display controller dims the intensity of the icon 184 associated with the actuating footswitch assembly 44. At this time both footswitch icons 32 associated with the handpiece under dual control are in dim state. This provides operating room personnel with an indication that, at the present time, neither footswitch assembly 44 has control of the handpiece 32.

Instead, as represented by step 206, waits to receive a signal from the second footswitch assembly 44 to turn off the handpiece 34. Until this signal is received, display controller 64 prohibits either footswitch assembly 44 from actuating the handpiece 34.

Once, in step 206, a signal is received from the second footswitch assembly to turn off the handpiece, display controller is able to execute step 208. In step 204, display controller 64 again monitors the output signals from both footswitch assemblies 44 to determine if either of them has turned on the handpiece 34. Thus, step 208 is essentially identical to first described step 194. Once this type of signal is received, display controller 64 reexcutes step 196 to reactuate the handpiece 34.

Figure 15A:
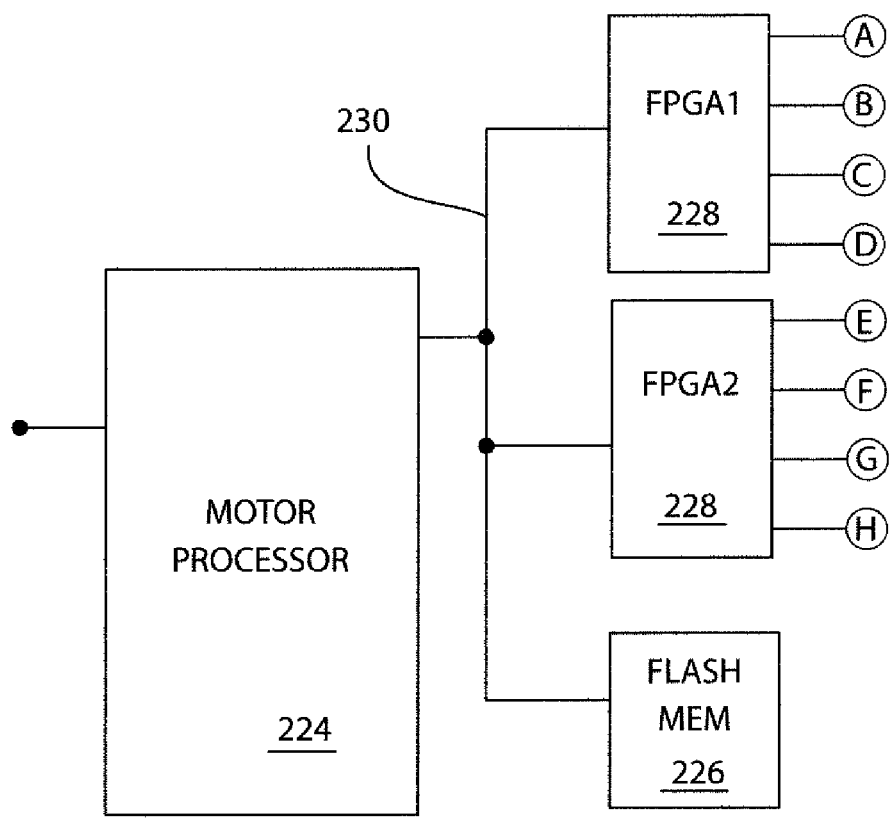
FIGS. 15A and 15B, when assembled together, form a block diagram of the main components of the motor controller.
Figure 15B:
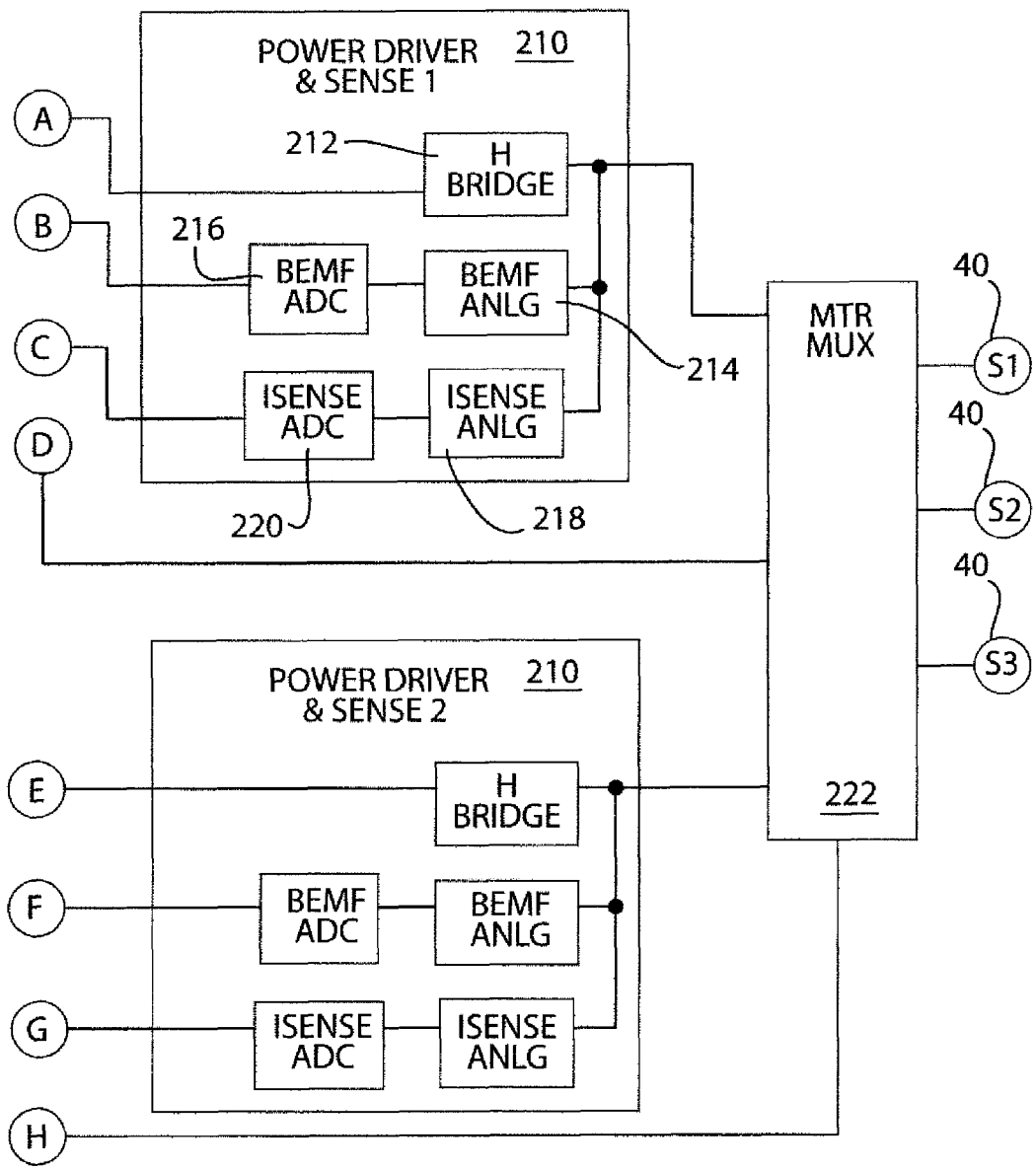

Motor controller 86 is now generally described by reference to FIGS. 15A and 15B. Specifically, the motor controller 84 includes two identical power driver and sense circuits 210. Each power driver and sense circuit 210 is capable of supply the power to the motor 36 of any handpiece 34 connected to any one of the sockets 40. (In FIG. 15B and the following figures, the individual sockets 40 are identified as S1, S2 and S3.) Specifically, internal to each power driver and sense circuit is an H-bridge 212. The H-bridge is the sub circuit that selectively ties each winding of the connected to either the 40 V power line or ground.

The power driver and sense circuit 210 also monitor signals generated as a consequence of the actuation of the handpiece motors. In order to perform this monitoring, each circuit 210 has a BEMF analog circuit 214 The BEMF analog circuit extracts the BEMF signal produced across the unenergized winding internal to the motor. Motor 36 is a brushless, sensorless motor that produces this type of signal. A BEMF analog to digital circuit 216 converts the extracted BEMF signal to a digital signal. AN ISENSE analog circuit 218 monitors the currents drawn by the handpiece motor 36 as well as currents internal to the control console 32. An ISENSE analog to digital circuit 220, also internal to circuit 210, converts the signals representative of the monitored currents into digital signals.

The power signals, the energization signals, to the motor windings output by the H bridges 212 are applied to a motor multiplexer 222. Motor multiplexer 222 is capable of generating the power signals generated by H-bridge 212 to any one of three sockets 40.

A motor processor 224, also part of the motor controller 86, regulates the operation of the power driver and sense circuits 210 and the motor multiplexer 222. In some preferred versions of the invention, a DSP processor is employed as the motor processor 224. One processor from which motor processor 224 can be constructed is the TMS320C6713 floating-point digital signal processor available from Texas Instruments of Dallas, Tex. Certain data used by motor processor 224 are written to and read from a flash memory 226. One such flash memory is available the Intel Corporation. Data stored in flash memory 226 include the instructions executed by motor processor 224, configuration data for the FPGAs 228 and calibration data for the current sensing circuits.

The actual control signals generated to the power driver and sense circuits 210 are generated by field programmable gate arrays (FPGAs) 228. Each FPGA 228, in response to instructions from the motor processor 224, generates control signals to a separate one of the motor driver and sense circuits 210. Each FPGA 228 also receives the digitized BEMF and sensed current signals from the circuit 210 to which the FPGA is connected. The FPGAs 228 also control the settings of motor multiplexer 222. Suitable FPGAs can be manufactured from the XC2S3x Spartan Series programmable gate arrays available from the Xilinx Corporation of San Jose, Calif.

Motor processor 224 is connected to the flash memory 226 and the FPGAs 228 by a parallel bus 230. (Bus 230 shown as a single line in FIG. 15A.).

Figure 16A:
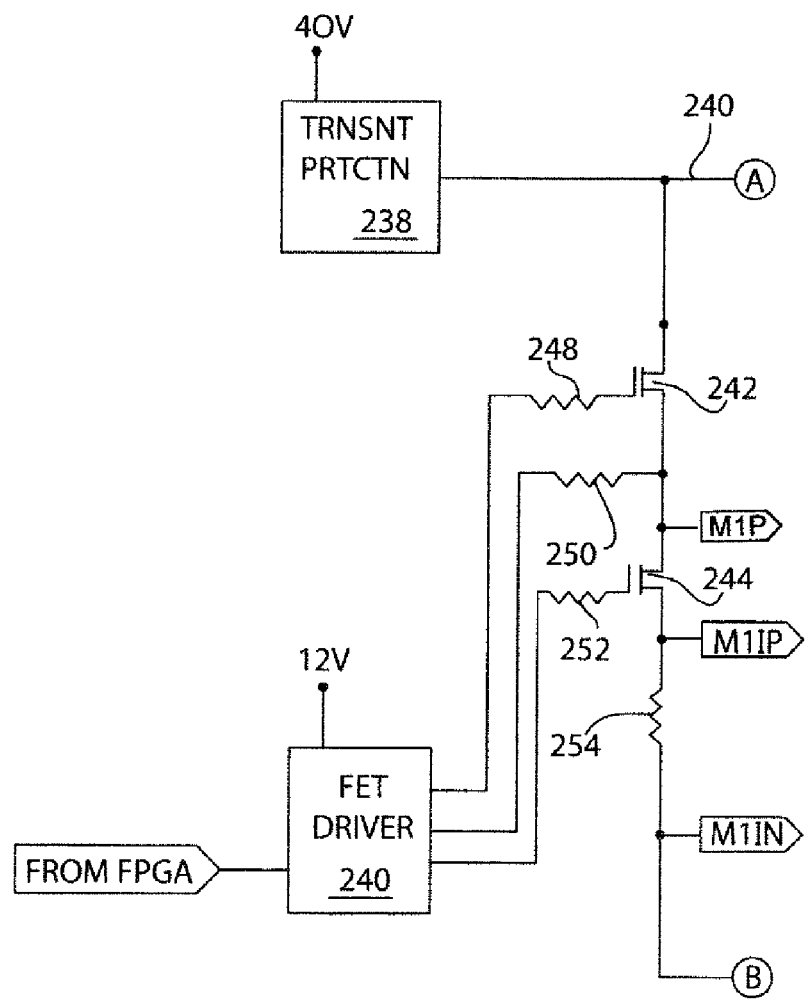
FIGS. 16A, 16B and 16C, when assembled together form a block and partial schematic diagram of the H bridge of the motor controller.
Figure 16B:
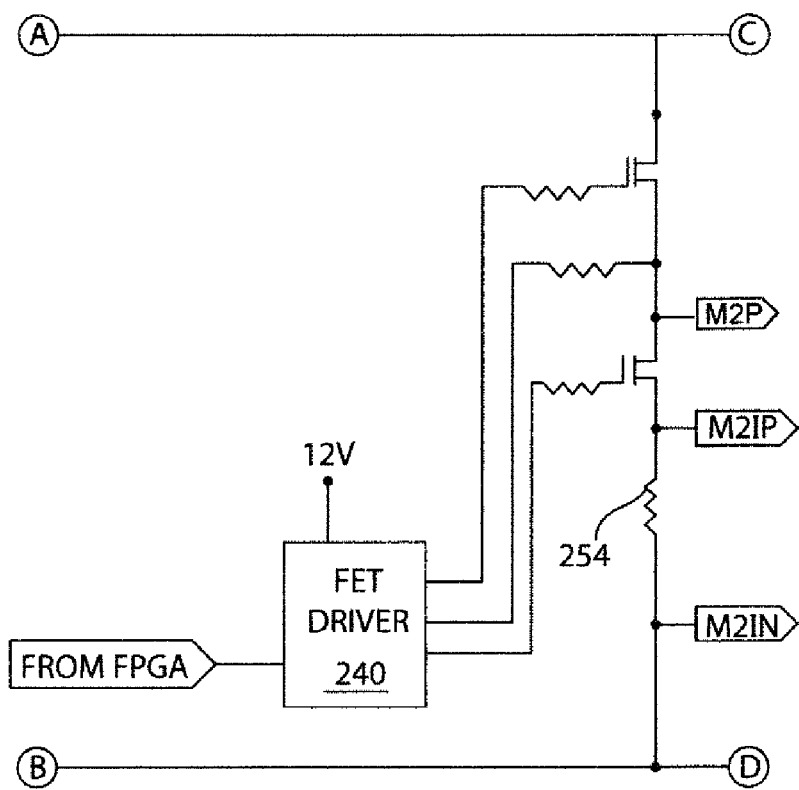
Figure 16C:
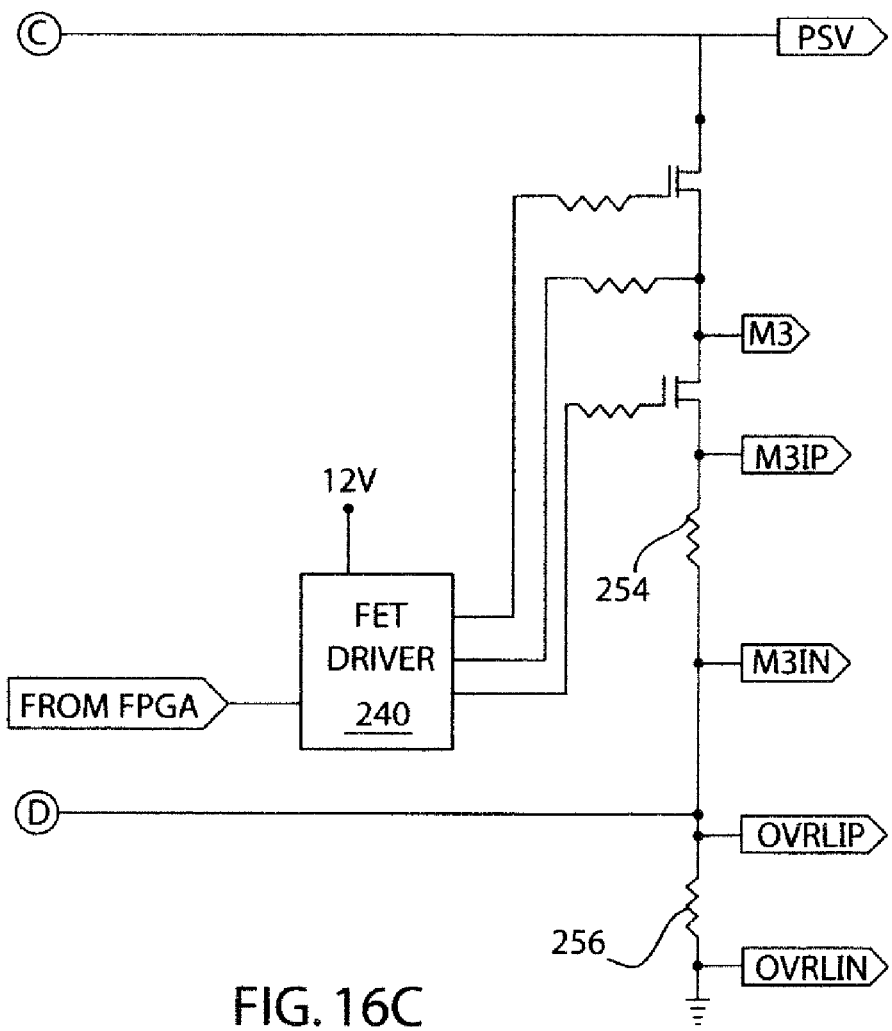

The basic structure of an H bridge 212 is shown in the block and schematic diagram formed by FIGS. 16A, 16B and 16C. By point of reference a stator 232 of a handpiece motor 36 to which the energization signals are applied is illustrated in FIG. 17. Stator 232 has three windings 234 that are tied to a common center point 236. The individual winding terminals that are tied to the 40 V power line, ground, or the BEMF analog circuit 214, are identified as M1, M2 and M3.

In FIG. 17, the depicted winding arrangement is of a wye-connected motor. It should be appreciated that system 10 of this invention can also be used to regulate the actuation of delta-connected motors.

The 40 V power signal is received by a transient protection circuit 238 internal to the H bridge 212. Transient protection circuit 238 selectively inhibits the outputting of the 40 V signal to prevent any braking transient signals from one winding 234 from glitching over to a second winding. Internal to the transient protection circuit is a FET (not illustrated) that controls the outputting of the 40 V signal. This FET is gated by a control signal from the complementary FPGA 228 (connection not shown). The 40 V power signal is output from transient protection circuit 238 over a 40 V rail 240 internal to the H bridge.

For each winding 234, the H-bridge 212 has two FETs 242 and 244, which, respectively, tie the winding terminal to the 40 V rail 240 or ground. In FIGS. 16A, 16B and 16C, the terminals tied to the winding terminals M1, M2 and M3, are identified as M1P, M2P and M3P, respectively. FET 242 is tied between the 40 V rail 240 and the MxP terminal. FET 244 is tied between the MxP terminal and ground. Not shown are the reverse biased zener diodes connected across the sources and drains of FETs 242 and 244, one each per FET, for voltage protection.

Each pair of FETs 242 and 244 are controlled by a FET driver 246. Each FET driver 246, in response to control signals from the complementary FPGA 228, assert the gate signals to the complementary FETs 242 and 244. A base driver that can be used as the foundation of a FET driver is the IR218x Series High Voltage Gate Driver available from International Rectifier (Richardson Electronics) of LaFox, Ill. The control signal generated by the FET driver 246 to the gate of FET 242 is applied to the gate through a resistor 248. The FET driver monitors the voltage at the source of the FET 242 through a resistor 250. The control signal to tie a winding 234 to ground is applied to the gate of FET 244 through a resistor 252.

A resistor 254 is connected between the source of each FET 244. The opposed ends of each resistor 254 are tied together and connected to a common resistor 256. The opposed end of resistor 256 is tied to ground. The voltage across each resistor 254 is measured as being a signal representative across the motor winding 234 with which the resistor 254 is associated. This voltage is measured off the MxIP and MxIN terminals in FIGS. 16A, 16B and 16C. The voltage across resistor 256 is measured as being a signal representative of the total current drawn by the handpiece motor 36. This signal is measured across the OVRLIP and OVERLIN terminals of FIG. 16C.

One sub-circuit of the BEMF analog circuit 214 is now described by reference to FIG. 18. This particular sub-circuit is used to measure the voltage of the power supply. Specifically, the 40 V rail signal from H bridge 21 is applied to this circuit; the PSI terminals in FIGS. 16C and 18. The signal on this circuit is tied to ground through two series connected resistors 258 and 260. The divided 40 V signal at the junction of resistors 258 and 260 is buffered by a unity gain amplifier 262. The output signal for amplifier 262 is the PSV_SNS signal representative of the power supply voltage.

Figure 19:
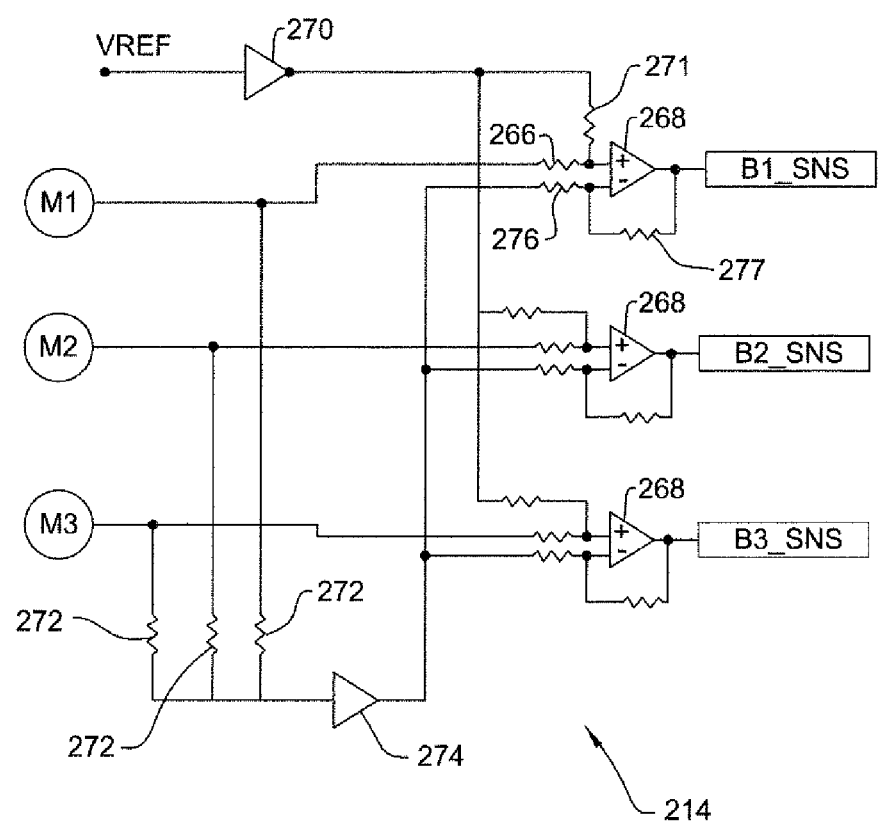
FIG. 19 is a block and partial schematic diagram of the circuit used to monitor the BEMF signals produced across the windings of the handpiece motor.

BEMF analog circuit 214 also includes the sub-circuit illustrated in FIG. 19. This is the actual sub-circuit that measures the BEMF signals developed across the motor windings 234 when they are not energized. In FIG. 19 the winding terminals are shown as being directly connected to the circuit. In actuality, each winding terminal M1, M2 and M3 is connected to a voltage divider and applied to a buffer amplifier. Thus the BEMF signals are preprocessed in manner similar to how the 40 V power signal is processed to form the PSV_SNS signal.

Each divided and buffered winding terminal signal is applied to through a resistor 266 to the noninverting input of an amplifier 268. Also applied to the noninverting terminal of each amplifier 268 is a V_REF signal. This V_REF signal, prior to application to amplifiers 268 is buffered by a unity gain amplifier 270. The signal from amplifier 270 to amplifier 268 is applied through a resistor 271.

Each winding terminal is also connected to a separate resistor 272. The free ends of the resistors 272 are tied together and applied to a unity gain buffer amplifier 274. The output signal from amplifier 274 is applied to the inverting input of each amplifier 268. The signals to the separate amplifiers 268 are applied through separate resistors 276. A feedback resistor 277 is tied between the output and inverting input terminals of each amplifier 268. Thus, amplifier 268 is used to produce a recreated neutral voltage for the motor consisting of the sum of the Bx_SNS signals divided by three.

The output signal of each amplifier 268 is the measure of the BEMF signal at the winding terminal to which the amplifier is connected. These signals are represented as the B1_SNS, B2_SNS and B3_SNS signals in the drawings. It is understood that individually each of these signals is representative of the voltage at the associated winding terminal minus the recreated neutral voltage for the motor 36.

Figure 20:
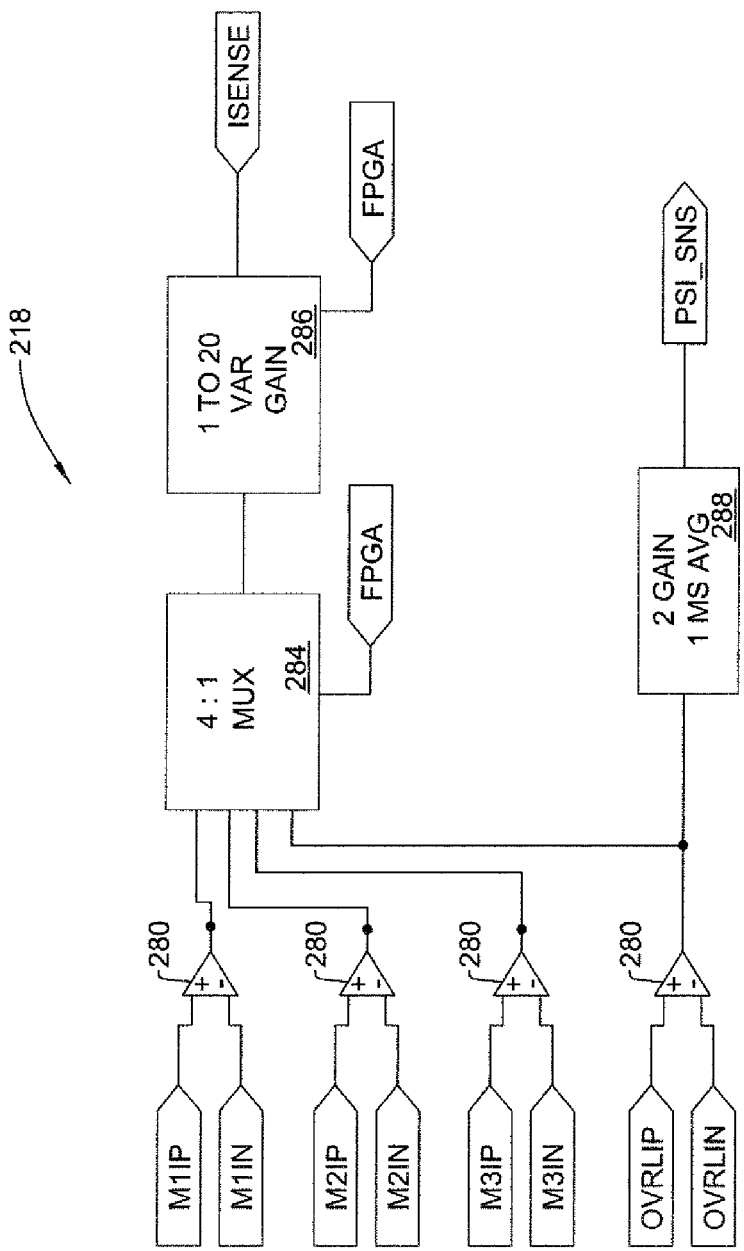
FIG. 20 is a block diagram of the circuit used to monitor the current drawn by the handpiece motor.

Referring to FIG. 20, a detailed description of the ISENSE analog circuit 218 is now provided. Each pair of MxIP and MxIN signals from the H-bridge 212 are applied to, respectively, the noninverting and inverting inputs of separate differential amplifiers 280. The OVERLIP and OVERLIN signals are similarly applied, respectively, to the noninverting and inverting inputs of a differential amplifier 280. While not shown, it should be understood a buffered VREF signal is applied to each noninverting input of the amplifiers 280. Individual buffer amplifiers, (not illustrated) are used to apply the buffered VREF signal to the amplifiers 280. Each amplifier 280 serves as a x10 gain circuit for the signal with which the amplifier is associated.

The signals from the individual amplifiers 280 are applied to a 4:1 multiplexer 284. Control signals from the FPGA 228 selectively forward one of the sensed current signals for further processing. The selected signal is forwarded from multiplexer 284 to a variable gain amplifier 286. In one version of the invention, amplifier 286 has a variable gain from 1 to 20. Amplifier 286 is a digital amplifier such that the gain can be adjusted in 256 steps. The command signals for establishing the gain of amplifier 286 come from the FPGA 228.

The output signal from amplifier 280 to which the OVERLIP and OVERLIN signals are applied is also applied to a gain and average circuit 288. This circuit multiplies the total motor current sensed circuit by 2. Circuit 288 also averages the signal over a select period, for example 1 millisecond. The output signal from gain and average circuit 288 is output as an average power drawn signal (PSI_SNS).

The BEMF analog to digital circuit 216 is now described by reference to FIG. 21. Circuit 216 includes a 5:1 multiplexer 292. Three input signals to multiplexer 292 are the three Bx_SNS BEMF signals from the BEMF analog circuit 214. A fourth input to multiplexer 292 is the PSV_SNS signal from buffer 262 representative of the power supply voltage. The remaining input to the multiplexer 292 is the PSI_SNS signal from gain and average circuit 288 representative of power supply current. Control signals from the FPGA 228 selects one of the five signals for further processing.

The signal selected by processing is output from multiplexer 292 to a high speed DC accurate buffer amplifier 294. Not illustrated is the feedback resistor tied between the output and inverting input of amplifier 294. Also not illustrated are the voltage limit diodes that are reverse biased tied to the output of amplifier 294. A first diode is tied between the amplifier 294 and the 5 Volt analog bus. A second diode is reverse bias tied between the output of amplifier 294 and ground.

The signal produced by amplifier 294 is applied to an analog-to-digital converter 296. The output signal from converter 296 is supplied to the FPGA 228.

The ISENSE analog to digital converter circuit 220 is illustrated in FIG. 22. The output signal from variable gain amplifier 286 is applied to a high speed buffer amplifier 298. Amplifier 298 and its supporting components, a feedback resistor and voltage limit diodes (components not illustrated) are similar to those attached to buffer amplifier 294. The output signal from buffer amplifier 298 is applied to an analog to digital converter 300. The output signal from converter 300 is applied to the FPGA 228.

Motor multiplexer 222 consists of six relay circuits 302, one of which is illustrated in FIG. 23. Each relay circuit receives a separate MxP signal. Three relay circuits 302 receive the M1P, M2P and M3P signals from one H-bridge 212. The remaining relay circuits 302 receive the M1P, M2P and M3P signals from the second H-bridge 212.

Each relay circuit 302 includes a first relay 304 and a second relay 306. The MxP signal is applied as input to relay 304. Relay 304 selectively applies the MxP signal to either one of the sockets 40, S3 in FIG. 23, or to relay 306. Relay 306 selectively applies the MxP signal to one of the remaining sockets 40, S1 or S2 in FIG. 23. The states of the relays 304 and 306 are regulated by control signals from the FPGA 228. These control signals are each applied to a FET 308. Each FET 308 controls the application of the 40 V signal to solenoid of the relay 304 or 306 with which the FET is associated. The 40 V signal is applied to each FET 308 through a resistor 309. The signal present at the drain of each FET 308 is applied to ground through two series connected resistors 310 and 312. The signals present at the resistor 310 and 312 junctions are applied back to the FPGA 228. The FPGA 228 uses these returned signals as status signals to verify the state of the relay circuits It should also be appreciated that only a pair of control signals from each FPGA 228 control the setting of the three relay circuits 302 that complement the specific FPGA. Similarly, only two status signals for the three relay circuits are returned to the FPGA 228.

Display controller 64 and motor processor 224 exchange signals over SPI bus 88. As part of the process of maintaining overall control of system 30 of this invention, display controller 64 maintains a power driver assignment table 320, FIG. 24. Internal to table 32 are two power driver assignment fields 322. Each power drive assignment field 322 is associated with a separate one power driver and sense circuits 210. The data in each field 322 indicates whether or not the associated power driver and sense circuit 210 is being used to energize a particular handpiece 34.

When the surgeon actuates one of the handpieces, display controller reads the data in the power driver assignment fields 322. Base on these data, display controller determines whether or not one of the power driver and sense circuits 210 is available to supply the energization signals to the handpiece 34. If one of the circuits 210 is available, the circuit is assigned to handpiece. Display controller 64 rewrites the data into the power driver assignment table 320 to indicate to which handpiece the newly assigned power driver circuit 210 has been assigned.

Display controller 64 also sends an initialization packet to motor processor 224. This packet contains data identifying which of the power driver and sense circuits 210 has been assigned to a handpiece 34. The types of data contained in the initialization data packet are discussed below.

Figure 32A:
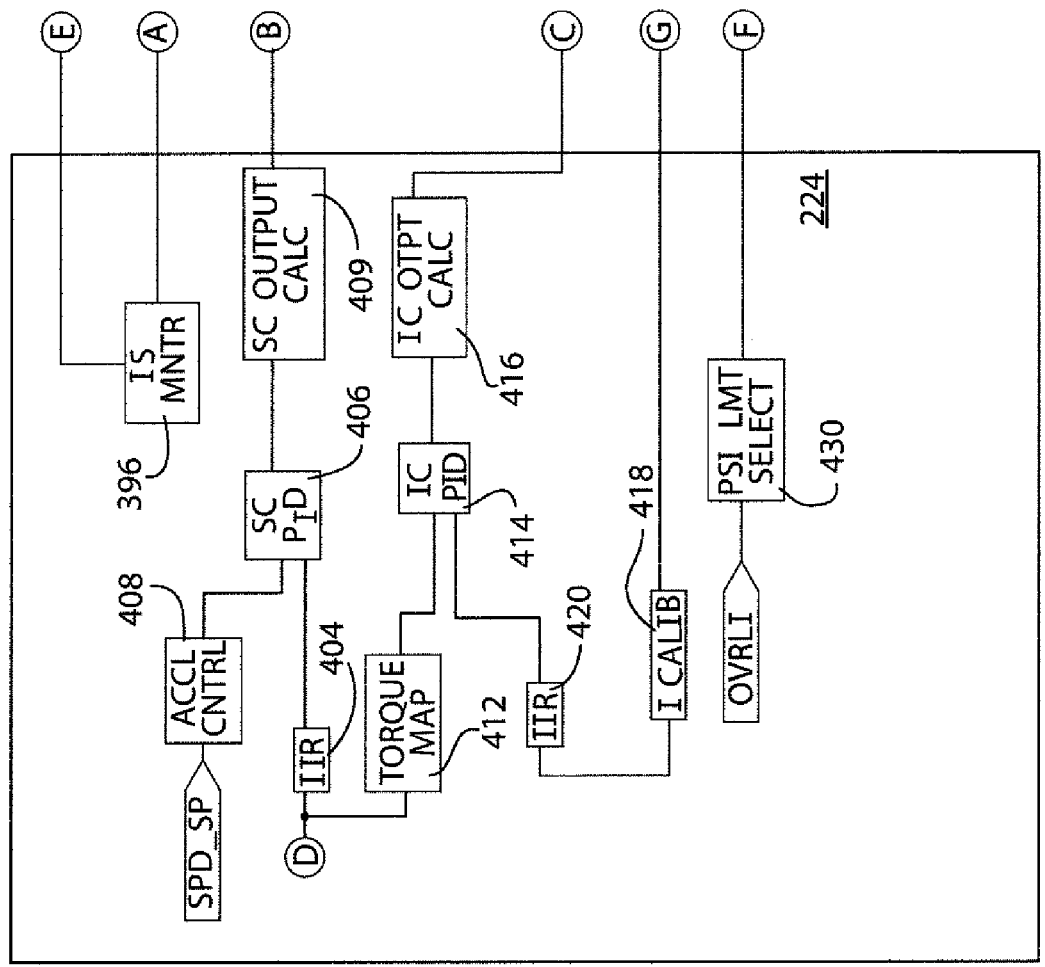
FIGS. 32A and 32B collectively represent the processes executed by the motor processor and a single field programmable gate array of the motor control to regulate the energization of a handpiece.
Figure 32B:
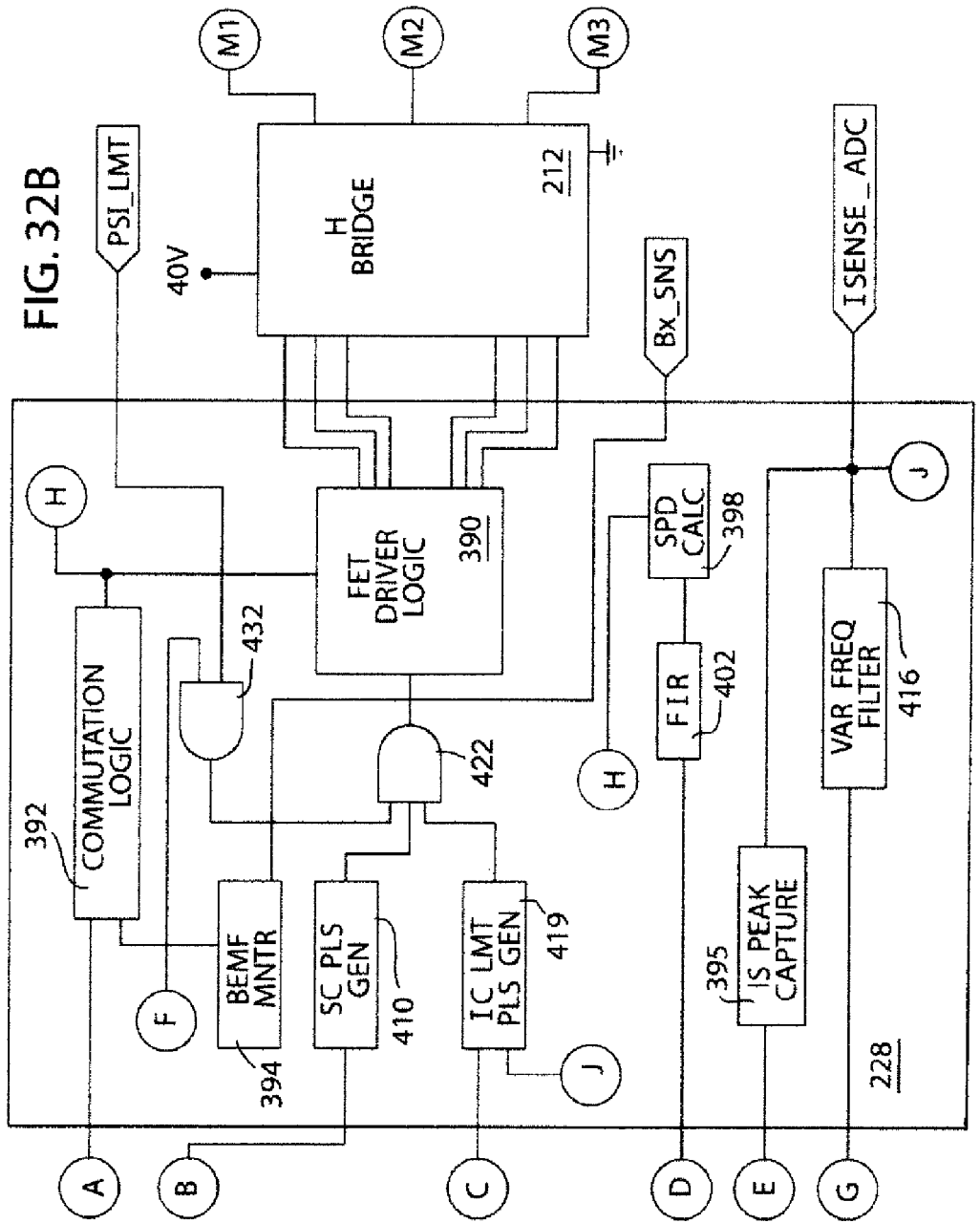

FIGS. 32A and 32B collectively illustrated the control processes executed by motor controller 224 and an FPGA 228 to regulate the application of energization signals to the windings 234 of an attached handpiece motor 36. FIG. 32A illustrates the processes run on the motor processor 224. The processes run of the FPGA 228 are illustrated in FIG. 32B. Generally it should be understood that the goal of these processes is to generate six (6) driver signals, one to each of the FETs 242 and 244 internal to H bridge 212. The turning on and off of FETs 242 and 244 is what causes current flow through the selected pair of windings at the selected chop rate.

One process module internal to the FPGA 228 is a FET driver logic module 390. Module 390 is the module internal to the FPGA that generates the signals to gate FETs 242 and 244. In FIG. 32B this is represented by the six conductors that extend from the FET driver logic module 390 to the H-bridge. In order to minimize confusion, subsequent discussed connections are illustrated with only a single line conductor even when multiple conductors are present. Also, it should be recognized that many of the subsequent discussed connections are within the same integrated circuit component.

The input signals to the FET driver logic module 390 are the instruction signals used to regulate the commutation of the windings and the driving of the windings. The commutation instruction signals inform FET driver logic module 390 across which pair of windings the energization signals should be applied. The drive signals inform FET driver logic module 390 of what the PWM rate and on duty cycle should be for the energization signals. Based on these instructions, module 390 generates the gate signals to turn FETs 242 and 244 off in an appropriate sequence.

The commutation instruction signals are generated by a commutation logic module 392 also internal to FPGA 228. Module 392, receives as input signals indicating the angular position of the motor rotor. Based on these signals, commutation logic module 392 generates the commutation instruction signals to FET driver logic module 390.

In the system of this invention, there are two alternative processes by which motor rotor position is determined. Internal to the FPGA 228 is a BEMF monitor module 394. Module 394 receives as input the digitized BEMF signals from the BEMF analog to digital converter 216. In FIG. 32B, these signals are represented as Bx_SNS signals. Based on these signals, the BEMF module 394 determines rotor position. Module 394 provides this information to the commutation and logic module 392.

As discussed below, when the handpiece motor 36 is operating at a low speeds, the BEMF signals cannot be used to determine rotor position. Thus, when the handpiece 34 is in this state, control console uses the second method of determining rotor position, inductance sensing. Inductance sensing is performed by an inductance sensing (IS) monitor module 396 internal to the motor processor 224. Generally, it should be understood that in inductance sensing, current through the windings 234 is measured to determine rotor position. The inputs signals into the IS monitor module 396 are measurements of the captured peaks of the measured current flows through the individual windings 234. These peaks are captured by a IS peak capture module 395 located in the FPGA 228. The input signals into module 395 are the digitized current measurement signals from the individual windings. It should be appreciated that, in inductance sensing mode, the current across resistor 256 is the current that is measured.

These currents are proportional to the voltages across resistors 254 of the H-bridge. Digitized representations of these signals are passed from the ISENSE analog to digital circuit 220 are passed from the FPGA 228 to the motor processor 224, connection not shown. A discussion of how inductance sensing processes are used to determine rotor position is set forth below. The rotor position determinations made by inductance sensing monitor module 396 are provided to the commutation logic module 392.

It should further be appreciated that motor controller 224 determines when the commutation logic module 392 should rely on BEMF sensed determinations of rotor position and when the module 392 should rely on the inductance sensed determinations. Motor processor 224 makes this determination based on the actual speed of the handpiece motor and speed cutoff data from the handpiece NOVRAM 72. This cutoff data, the field in which it is stored not shown, indicates below what speed inductance sensed rotor position determinations are used to regulate commutation. This cut off speed is supplied to the motor processor 224 as part of the initialization packet. Thus while the input connections are not show, it should be further understood that inductance sensing monitor module 396 also receives an indication of motor speed and the cutoff speed to perform the required comparison.

It should further be understood that inductance sensing monitor module 396 also communicates with BEMF module 394, connection not shown Specifically, inductance sensing monitor module 396 provides the initial start logic data to the BEMF module 394 that module 394 needs to perform BEMF monitoring of rotor position.

Three basic input variables are used to cause the windings to be driven. One input is based on the difference between the actual and user-selected speed for the handpiece motor. A second input is based on the current drawn by the motor 36. The third input is based on the overall power that is, at any given instant, being consumed by the system 10.

The digitized BEMF signals, the Bx_SNS signals in FIG. 32B, are what are used by the FPGA 228 to determine raw speed of the handpiece motor 36. Specifically, internal to the FPGA 228 is a speed calculator module 398. Speed calculator module 398, receives the output commutation instruction signals from the commutation logic module 392, connection H in FIG. 32B. Based on the times between the commutations as designated by these signals, speed calculator module 398 generates a digital representation of rotor speed. This speed value is filtered by an FIR filter 402 internal to the FPGA. The coefficients for this filter from the handpiece NOVRAM 72 are contained in the initialization packet. (It should likewise be appreciated, the filter coefficients for all filters in the DSP 224 and FPGA 228 come from the NOVRAM 72 in the initialization packet.

The filtered speed signal is forwarded from the FPGA 228 to an IIR filter 404 internal to motor controller 224. The filtered signal IIR filter 404 is applied as one input variable to a speed control (SC) proportional integral derivative (PID) algorithm module 406.

The second variable into the SC PID module 406 is a user speed set-point signal. This signal is generally a digital representation of the user selected speed for the handpiece. This signal is provided by display controller 64 in both the initialization packet and in speed set-point packets. These speed set-packets are repeatedly sent by the display controller 86 to motor processor 224 as long as the handpiece remains actuated. Each speed set-point contains data identifying the handpiece 34 with which the packet is associated and data indicating the user-set speed for the handpiece 34. These latter data are determined by the display controller by reference to the input device the surgeon actuates to change motor speed. While a handpiece remains actuated, display controller 64 typically sends a speed set-point packet once every 10 milliseconds.

Prior to the speed set-point signal being received by the SC PID module 406, the signal may be processed by an acceleration control module 408. This is because over time, the speed set-point signal will change as a result of the surgeon speeding up, slowing down, or braking the handpiece motor 36. Depending of the rate of change of the actual speed set-point signal, acceleration control module 408 adjusts the rate at which the set-point signal applied to the SC PID module 406 actually changes. This is done to minimize any jerking or other uneven operation of the handpiece motor 34 that may occur as a result of rapid acceleration, deceleration or braking.

It should be recognized that the parameters the acceleration control module uses to modify the rate of change of the speed set-point signal come from the handpiece NOVRAM 72 in the initialization packet.

The SC PID module 406, based on the difference between the actual (filtered) motor speed and the speed indicated by the set-point signal determines an SC PID output signal. The algorithm by which this signal is generated is made is known in the art.

While there are two constantly changing inputs into the SC PID module 406, it should be appreciated that there are other variables into the algorithm. These variables include, proportional gain, integral gain derivative, gain and derivative time constant, output max and output min. These variables, which are essentially constant, are supplied from the handpiece NOVRAM 72 by the initialization packet. For some motors, different sets of these variables are employed for speed control purposes at different speed ranges. The multiple sets of variables are supplied in the initialization packet. Based on the current speed range in which the handpiece motor 36 is operating, motor processor 224 loads the appropriate set of variables into the SC PID module 406.

The above mentioned constant-over-speed range variables are also supplied to a current control (IC) PID module 414. It should be appreciated that the set of variables applied to the SP PID and IC PID modules 406 and 414, respectively, are different.

The SC PID output signal from module 406 is applied to an SC output calculation module 409. A second input into module 408 is a motor PWM frequency. This variable is from the handpiece NOVRAM 72 and is supplied in the initialization packet. Based on these inputs, SC output calculation module 409 determines two values, the PWM period and the PWM on time for the drive signal.

Output signals representative of the values produced by the SC output calculation module are forwarded to a SC pulse generator 410 internal to the FPGA 228. The SC pulse generator 410, based on the inputs from module 409 produces a train of speed control-based PWM drive pulses.

The current based drive signals are based on both a current set-point for the handpiece motor 36 and the actual current drawn by the motor. A torque map module 412 produces the current set-point value. The three variable form which the current set-point are determined are, the speed of the motor, a torque map and a constant. Torque map module 412 receives the filtered speed signal from the FPGA FIR 402. The torque map is a relationship specific to the motor of the torque the motor can develop at a specific speed. The constant converts the speed-based torque into a current set-point. The data for the torque may and the constant are from the NOVRAM 72 and contained in the initialization packet.

Thus, for a given speed, based on the torque map, module 412 determines the torque the motor should developed. Based on this determination and the constant, module 412 determines the current the motor should draw. Torque map module 412 supplies data representative of this current set-point to the IC PID 414 algorithm module.

The second continually varying input into the IC PID module 414 is the actual current drawn by the motor. The current measurement supplied to module 414 is based on the interleaved individual winding current measurements from across resistors 254 of the H-bridge 212, the MxI signals in FIG. 32B. These signals are supplied to a two stage variable frequency filter 416 in the FPGA 228. Filter 228 removes the high frequency ripple in this current signal to commutation switching.

The filtered current signal from filter 228 is applied to a current calibration module 418 internal to the motor processor 224. Current calibration module 418 calibrates the current for subsequent processing. A variable module 418 employs to determine the extent the current drawn signal needs to be calibrated is the value indicating the extent the analog version of the current signal was amplified by variable gain amplifier 286. This value, as well as the setting for amplifier 286 are from the handpiece NOVRAM 72 and contained in the initialization packet.

The calibrated current reading is filtered by an IIR 420 also in the motor processor 224. The filtered sensed current is applied to the IC PID module 414 as the second variable.

Based on the current set point and the filtered and calibrated measurement of actual current, the IC PID module produces a midpoint current value. The midpoint current value is forwarded to a current control output calculation module 416. From the initialization packet, module 416 previously received current range window data. These data indicate a range between which the motor current should oscillate. Based on these window range data and the midpoint current value, current control output calculation modulation produces ILIMITH (high) and ILIMITL (low) current limits. It should be appreciated that the midpoint current value is between these current limits. The range between the limits is based on the range data in the initialization packet.

The motor processor 224 provides the ILIMITH and ILIMITL values to a current control limit pulse generator 419 internal to the FPGA. Generator 419 receives as another input a measure of the actual motor current. In actuality the interleaved digitized versions of the three winding currents, the digitized MxI current signals are applied to generator 419. Based on the ILIMITx values and the measured current, current control limit pulse generator 419, based on a bang-bang process, selectively clocks out current control drive pulses.

The speed control-based PWM drive pulses from the SC pulse generator 410 and the current control drive pulses from the current control limit pulse generator 419 are two of the signals used to control the generation of driving of the windings 234. The third input signal is a power supply limit (PSI_LMT) signal. As discussed below, this signal is asserted when the components of system 10 consume more power than the console power supply 90 can provide.

These three signals are applied to an AND logic module 422 internal to the FPGA 228. The output from module 422 is applied to FET driver logic module 390 as the signal to drive the windings 234. AND logic module 422 is configured to assert the signal to drive the windings 234 only when the speed control-based PWM drive pulses and the current control drive pulses simultaneous indicate the windings are to be driven and the power limit exceeded signal is not asserted.

It should be recognized that a feature of the above assembly is that it provides for precise torque control of the operation of a handpiece 34. Specifically, by entering the appropriate commands, display controller 64 is directed to present on display 42 torque control setting images. By pressing the touch screen buttons associated with these images, the surgeon established the maximum torque the handpiece motor is to develop. This is useful because for certain procedures, such as the driving in of an implant into tissue, only a select maximum amount of torque should be applied. Once the surgeon establishes this torque limit, data regarding its value is provided by display controller 64 to motor controller 224 in the initialization packet. Based on these data, motor processor 224 configures the torque map module 412 to ensure that the module never generates a signal indicating that the handpiece motor 36 should produce more torque than the defined maximum amount.

Figure 33:
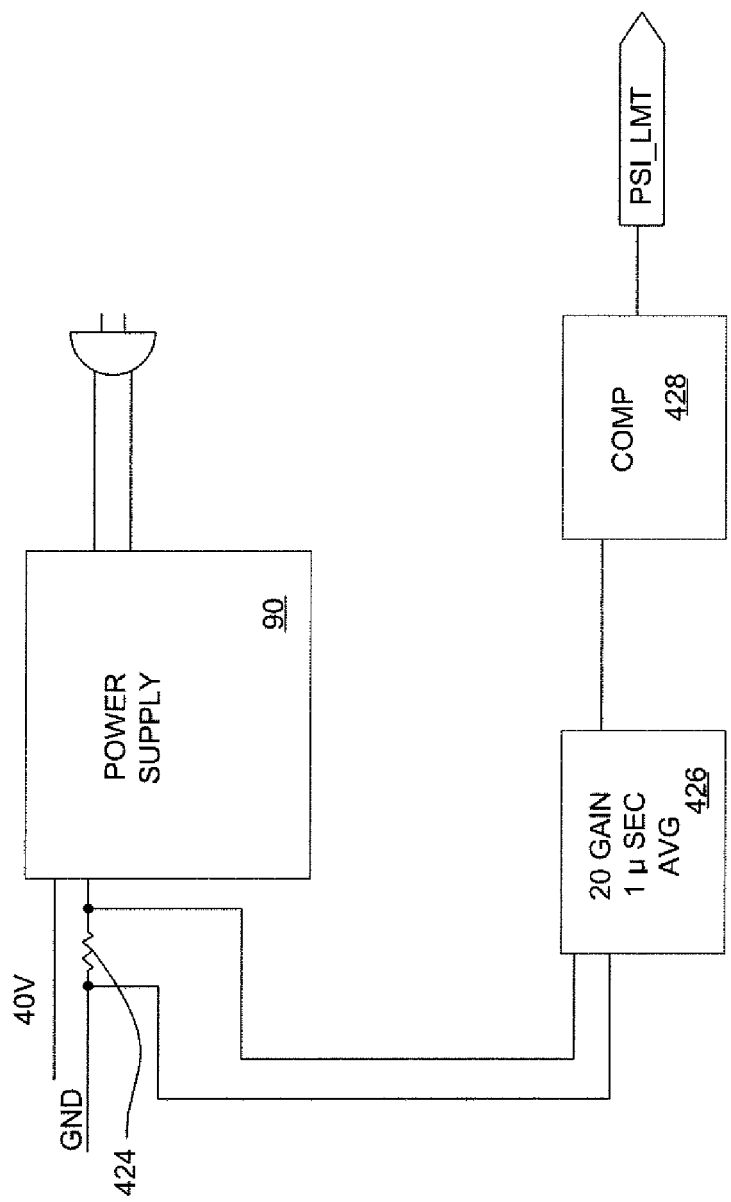
FIG. 33 is a block and partial schematic drawing of the circuit that selectively asserts the power supply limit signal.

An understanding of when and how the power supply limit signal is asserted can be obtained by initial reference to FIG. 33. Initially it should be understood that the reason a means for power limiting is provided is that there may be times when surgeons may attempt to simultaneously drive two instruments that collectively consume more power than control console 32 can provide. This is because amount of power any power supply can provide is invariably limited. By way of example, it should be understood that in some versions of the invention it is anticipated power supply 90 provides up to 400 Watts of power. For reasons of size and to minimize the amount of heat emitted by the control console 32, it is often considered reasonable design consideration to so limit the amount of power the control console can provide. Moreover, there are seldom instances when both handpieces being simultaneously driven by the control console will need more than 400 Watts of power. Therefore, it should be appreciated that is not an efficient use of resources to provide a power supply that could supply more power.

However, there may occasionally be instances when two high-power consuming handpieces 34 are simultaneously connected to and energized by the control console 32. The power supply limit circuit of system 10 of this invention allows both handpieces to be so actuated.

As seen by reference to FIG. 33, the power supply limit circuit includes a resistor 424 connected to the ground out of the power supply across which the current out of the power supply 40 is measured. The voltage across resistor 424 is applied to a gain and average circuit 426. In one version of the invention, this current drawn signal is multiplied by 20 and averaged over 1 microsecond.

The multiplied and averaged power supply current signal from circuit 426 is applied to a comparator 428. The second input to comparator 428 is a reference signal, not shown, representative of the maximum current the power should draw. The power is provided to the handpieces in the form of a 40 volt potential. Therefore, the maximum current the power supply should draw to ensure that it does not consume more than 400 Watts is 10 Amps. In actuality, the power supply 90 is capable of producing up to 500 Watts, the additional, however, is used by the internal console components such as pump motor 60. Performing the power limit monitoring at a level less than power supply's actual power limit, essentially eliminates the likelihood the power supply could consume so much power there could be component failure.

Thus, comparator 428 continually monitors the adjusted power supply current to determine whether or not the power supply is consuming too much current. If this condition occurs, comparator 428 asserts the PSI_LMT signal.

The PSI_LMT signal is applied to both FPGAs 228. As part of the overall process of regulating the energization of the handpiece motors 36, motor processor 224 continually determines which motor, in view of the power limit being exceeded, should temporarily be deactuated. This determination is made by a power supply current (PSI) limit select module 430 internal to the motor processor 224. The inputs into module 430 are values of the current presently being drawn by each handpiece motor 36. Specifically these are current drawn measurements through the H bridge resistors 256. In FIG. 32A this is depicted by a single OVERLI signal directly into module 430. In actuality it is understood that digitized forms of these motor current signals are forwarded from both FPGAs 228 to the PSI limit select module 430. By comparing these signals, module 430 determines which of the two actuated handpiece motors 36 at any given instant is drawing more current, consuming more power. The PSI limit module 430 selects this handpiece motor 36 for potential power limited necessitated deactivation.

Specifically, PSI limit module 430 asserts a power limit enable signal to an AND logic module 432 internal to the FPGA 228 associated with the selected handpiece motor 36. The PSI_LMT signal, when asserted, is simultaneously received by the AND logic modules 432 of both FPGAs 228. Only the module 432 to which power limit enable signal has been asserted forwards the PSI_LMT signal. Specifically, this signal is forwarded to AND logic module 422. As discussed above, when AND logic module 422 receives the PSI_LMT signal, module 422 inhibits the assertion of the drive signals to FET driver logic 390.

Thus, the assertion of the PSI_LMT signal causes the enabled FPGA 228 to temporarily stop asserting drive signals. This momentarily stops the application of energization signal across the windings of the motor 36. This momentary cessation of the application of the energization signals to the motor 36 causes the average power drawn by the motor to momentarily drop. This prevents power supply 90 from outputting more than the amount of power it is designed to produce.

As discussed above, at normal operating speeds, the FPGA 228 associated with the driver power driver and sense circuit 210, regulates the commutation switching of the motor windings 234 by monitoring the BEMF signals generated across the unenergized motor winding 234. However, at low speeds, speeds 10% or below of the maximum operating speed of the handpiece motor 36, and for some handpieces, speeds 5% or below the BEMF signal across a winding drops to a level at which it cannot be detected.

When this event occurs, motor controller 86 employs inductance sensing to determine the position of the motor rotor. More particularly, as seen in FIG. 27 internal to handpiece NOVRAM 72 there is a BEMF/IS set point field 339. Field 339 contains data that indicates the speed above which motor controller 86 should employ BEMF sensing to determine rotor position. At speeds at or below the speed set forth in field 339, motor controller 86 employs the below-described inductive sensing process to determine rotor position. The speed level in the BEMF/IS set point field is supplied by display controller 64 to the motor processor 224 in the initialization packet. Based on the data indicating motor speed and the value from field 339, motor processor 224 selectively uses BEMF sensing or inductive sensing to regulate the energization of the handpiece motor 36.

The motor controller 86 starts the inductive sensing process by measuring the inductance across the windings in each of the six motor phases. This is performed by first negating the application of energization signals to the windings 234 as represented by time period 336 in the plot of FIG. 25.

Then, during time period, short voltage pulses are applied across each motor winding 234. In order to measure inductance in a first phase, one of the windings is tied to the 40 V rail 240 of the H-bridge 212, the remaining two windings are tied to ground. The current developed by the winding connected to the 40 V rail 240 is then measured. To measure inductance in a second phase opposite the first phase, the power connections of the windings are reversed. Thus, the two windings just tied to ground are connected to the 40 V rail 240; the winding 234 attached to the rail is tied to ground. Current through the ground tied winding is then measured. These measurements are made for all three windings 234. Thus as depicted in FIG. 25, there are six measured current pulses 338 from the motor 36.

In theory, for any given position of the motor rotor, the measured current for one of the motor phases should be higher than measured current for the remaining five phase measurements. This is because the position of the rotor magnets affects the inductance across the windings and therefore, the current through windings.

Figure 26:
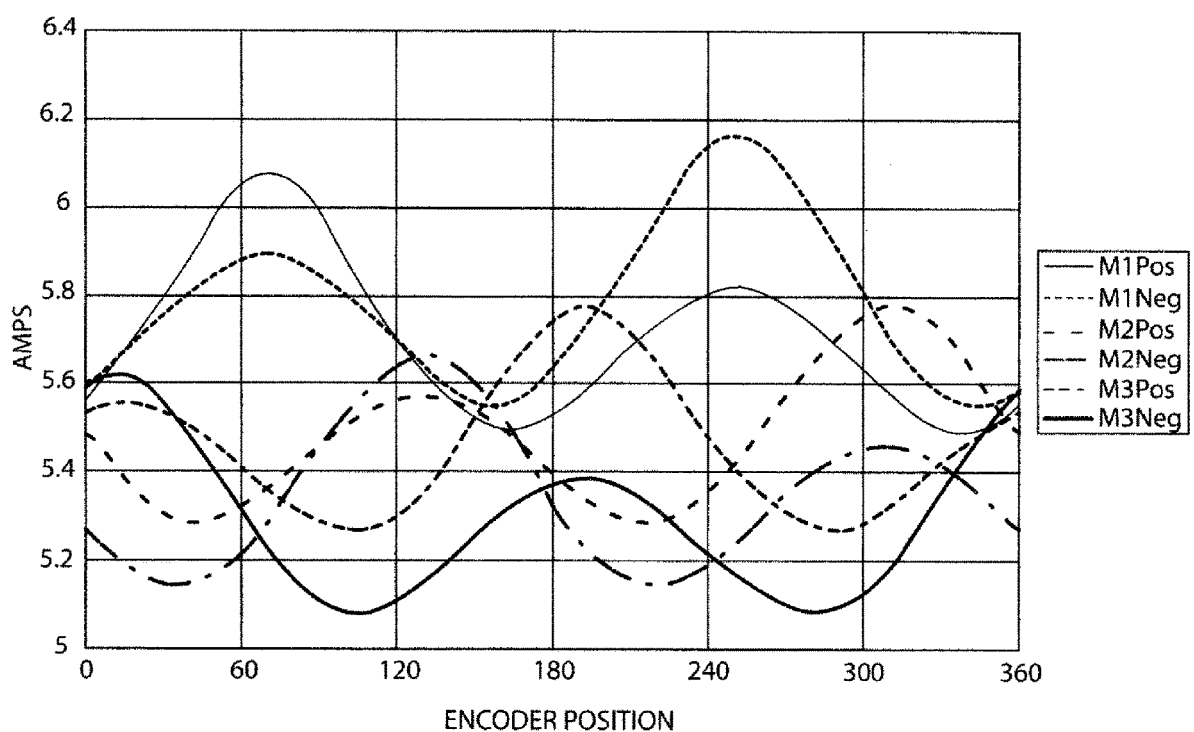
FIG. 26 is a graph of the relationship of measured current to motor rotor position for a surgical handpiece.

However, as indicated by reference to the graph of FIG. 26, in actuality, it has been found that for the DC motors of surgical handpieces 34, there is a poor correlation of measured inductance to rotor position. It is believed this poor correlation is due to the fact that the handpieces 34 integral with system 30 of this invention have motors 36 with relatively small rotors. In particular the rotors typically are 0.5 inches or less in diameter. Still other of the motor rotors have diameters of 0.25 inches or less. Due to the relatively small size of the magnets integral with these rotors, the magnets do not change the inductance of the adjacent motor windings 234 to the degree at which inductance changes alone can be used to determine rotor position.

Thus, in system 30 of this motor processor 224 applies gain and offset values to the six measured motor phase currents. These gain and offset values come from data fields 340 and 342, illustrated in FIG. 27, within handpiece NOVRAM 72. Specifically, for each rotor position, NOVRAM 72 contains data in field 340 that includes the coefficient for multiplying the measured current, to produce the gain. Data in each field 342 contains a constant that is applied to the multiplied gain, the offset. These data, as well as the data in the BEMF/IS speed set point field 339 are forwarded from display controller 64 to motor processor 224 as part of the initialization packet.

It should be understood that for each type of motor 36, the gain and offset values for fields 340 and 342, respectively, are developed by empirical analysis of the operation of the motor.

Figure 28:
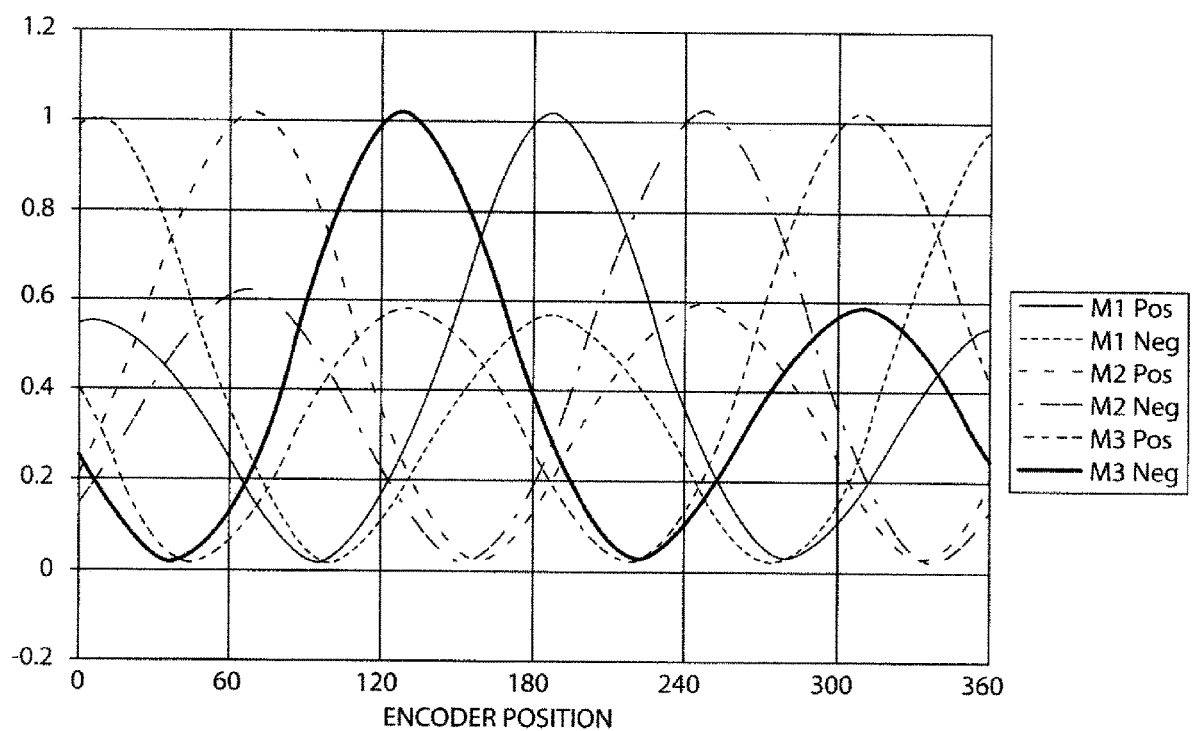
FIG. 28 is a graph of calibrated measured rotor current to motor rotor position when inductive sensing is performed.

Based on these retrieved gain and offset data, motor processor 224 is able to produced a calibrated, normalized current measurement for each current value. As seen by reference to FIG. 28, these calibrated normalized values result in a plot wherein for each rotor position a single one of the current values is higher than the other current values.

Thus based on these calibrated and normalized measurements of winding inductance, motor processor 228 is able to determine the position of the motor rotor. Based on this determination, motor processor 228 is able to determine through which windings 234 current should next be applied. This is represented in FIG. 25 by period 346 an energization signal is applied to across the appropriate two of the motor windings 234. It will be noted also from this figure that a quiescent period 350 that proceeds period 336 so the current measurements can made. Collectively, periods 336 and 350 are approximately 10% of the size of period 346 in which a signal is applied to a single winding pair to actuate the motor. Generally the combined period for a single cycle of periods 336, 346 and 350 is 1 millisecond.

It should be recognized that this use of inductance measurement sensing to monitor rotor position and regulate the energization of windings can be used in situations other than when the handpiece motor 36 is operating in a low speed state. This inductance measurement sensing can be used to regulate winding energization even when the motor is stopped, a 0 RPM speed. Thus, inductance measurement sensing can be used to regulate motor start up when the handpiece is initially actuated. Inductance measurement sensing can also be used to regulate motor actuation when, as a result of the motor developing an amount of torque that approaches or equals the maximum torque it can develop, the motor rotor slows to a very low speed or even stops.

Figure 29:
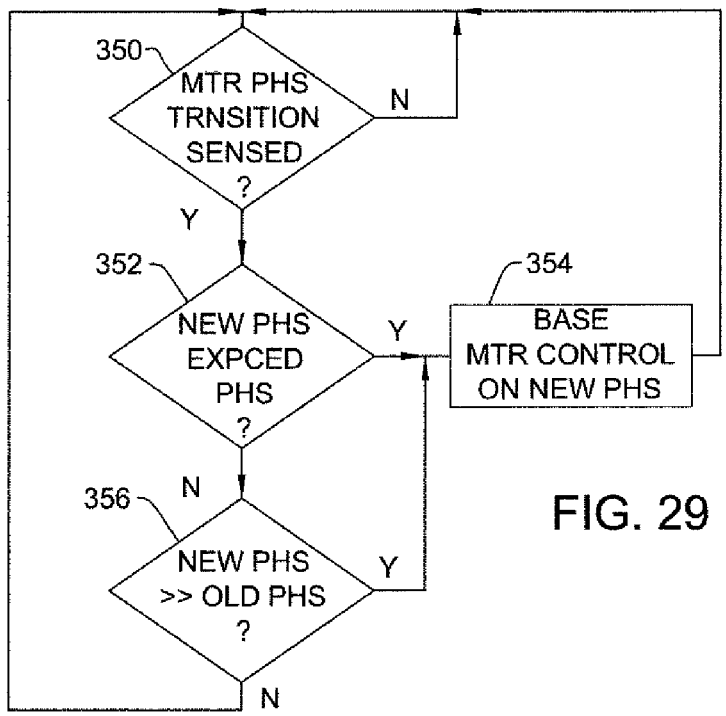
FIG. 29 is flow chart of the process steps executed by the motor controller during inductance sensing mode to determine whether or not, based on a transition to particular motor pole state, the motor rotor should be have considered to have shifted position.

A step in the inductance sensing of rotor position that is also practiced involves commutation state calculation. Specifically, in the system 30 of this invention, motor processor 224 does more than base commutation state on a calibrated and normalized measure of motor phase inductance. Motor processor also reviews whether or not after one given commutation phase in inductance sensing is determined, the next determined phase is appropriate. Based on this determination, motor processor then places the motor 36 in the next appropriate commutation state. This process can be understood by reference to the flow chart of FIG. 29. Step 350, represents the transition from one peak sensed inductive current phase to a second peak sensed inductive current phase. After this transition occurs, in step 352, motor processor 224 determines whether or not the second peak sensed inductive current phase is one that is immediately adjacent the previously determined first peak sensed inductive current phase. By way of example to the calibrated and normalized peak currents of FIG. 28, if the immediate past current phase was the M3 Negative phase, than the immediately adjacent phases are the M2 Positive, in one direction, and M1 Positive phase, in the opposite direction. In step 352 if the sensed phase is from one of these two phases, it is assumed that motor is working properly. Then, in step 354, motor processor 224 instructs the appropriate FPGA 228 to make the next appropriate commutation shift of the energization signals applied to the windings.

However, in step 352 it may be determined, for example, that immediately after the M3 Negative sensed inductive current phase is highest, the next sensed highest inductive current is from the M3 Positive phase. This is because due to manufacturing tolerances, during the transition between from the M3 Negative and the M1 Positive phases being highest, the inductive sensed current corresponding to the M3 Positive phase is highest.

In response to this determination, in step 356, motor processor 224 determines whether or not the peak inductive sensed current for this new phase is reaches a level that is significantly higher than level for at which the phase transition between sensed currents occurs. In present example, motor processor 224 would only switch from motor driving based on the M3 Negative sensed phase to driving based on the rotor being in the M3 Positive phase, if the normalized inductive sensed current for the M3 Positive phase exceeds that of the last measured M3 Negative phase by a value of 0.5.

If, in step 356, it is determined that the apparently out of sequence inductance measurement is appreciably higher than the preceding measurement, the measurement is accepted as accurate. Step 354 is executed. In this version of step 354, motor processor 224 instructs the appropriate FPGA 228 to make the next appropriate commutation shift of the energization signals based on the motor being in the detected phase.

Alternatively, in step 356 it may be determined that the apparently out of sequence inductive measurement is below this threshold value. If this determination is made, this highest determined inductive sensed phase is ignored. Instead, step 350 is reexecuted. In this, and in all executions of steps 350 and 352, inductance sensing monitor module 396 basis its determination on whether or not there has been a change in motor phase when the next expected phase is only marginally higher than the present phase. In the present example, the calibrated and normalized inductance sensed signal for the expected M1 Positive stage only has to be 0.1 higher than that of the present phase, the M3 Negative phase, for the motor processor 224 to determine that the motor rotor is now in a position corresponding to the M1 Positive phase.

In step 356 it may be determined that the out-of-sequence inductance sensed measurement is appreciably higher than the value of the inductance sensed measurement of the last phase. This "last phase inductance sensed value" is from the crossing of the two inductance sensed signals. If this event occurs, it is interpreted by motor processor 224 as meaning that the motor rotor is actually in the position indicated by this new highest inductance sensed measurement. In this event, motor processor applies energization signals to the motor windings based on this new determination of rotor position.

An advantage of this feature of system 30 of this invention is that it essentially eliminates the likelihood that small out-of-sequence determinations of next highest motor phase that occur because of operation glitches and motor winding variations do not cause the motor controller 86 to incorrectly energize the windings based on erroneous determinations of rotor position.

Figure 30:
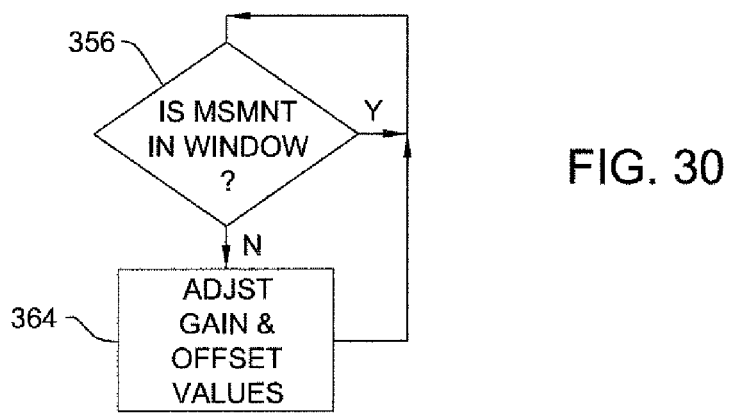
FIG. 30 is a flow chart of the process steps executed by the motor controller to during the inductance sensing mode to determine whether or not the gain and offset calibration values for a particular motor phase should be recalibrated.

Motor processor 224 of this invention further configured to adjust the gain and offset constants for the motor phases. Specifically as indicated by the flow chart of FIG. 30, in step 362 motor processor 224 determines, for each motor phase, whether or not, for a rotation of the rotor, the calibrated and normalized inductance sensed measurements are within a predefined window. This window can, for example be between −0.1 and 1.1. If in step 362 it is determined that the calibrated and sensed inductance sensed measurements for the phase are in this range, no recalibration is performed.

However, in step 362 it may be determined that the calibrated and normalized inductance sensed measurement is outside of the defined window. If this state is detected, in step 364, motor processor 224 performs adjustments of the gain and offset coefficients. These adjustments are performed iteratively until, in a subsequent execution of step 362 it is determined that the calibrated and normalized inductance sensed measurements for the motor phase are within the defined window.

This feature of the invention ensures that shifts of the inductance waveforms over time due to changes in temperature and component wear do not result in incorrect motor states from being calculated.

Still other methods of performing this recalibration is by locking the motor rotor in set of known positions and then taking inductance measurements. Recalibration is then made based on the measured inductance. Long term averages of sensed inductance measurements can also be employed to determine how to appropriate adjust the gain and offset values.

In some versions of the invention, display controller 64, through the NOVRAM interface 78, writes the recalculated gain and offset values from the motor phases into the handpiece EEPROM. These data are then read by the display calculator and used the next time the handpiece 34 is plugged into the control console.

In practice, this on the fly recalibration of the motor pole gain and offset values may be performed as soon as the inductance sensing process is initialized. The maximum and minimum normalized sensed inductance values are captured. If through a rotation of the motor rotor it is determined the peak-to-peak normalized sensed values exceed a value of 1.0 or are less than 1.0, the gain and offset values are recalculated by the motor processor 224 for this current run of the handpiece 34.

Many handpiece motors are constructed so that when rotor position based control switches from the inductance sensing mode to the BEMF sensing mode that energization sequence for the windings remains constant. Some motors 36 are, however, constructed so that when control shifts from between the inductance sensing and BEMF sensing modes, the energization sequence of the windings is reversed. Handpiece NOVRAM 72 thus contains a data flag, represented by BEMF/IS Reverse Energization Sequence field 368 in FIG. 27. The setting of this flag in field 368 indicates whether or not motor controller 86 upon switching between BEMF sensing and inductance sensing of rotor position should reverse the energization sequence of the windings.

Based on the setting of the flag in field 368, motor processor 224, upon changing sensing modes selectively also reverses the sequence in which the windings are commutated.

The above means of inductance sensing monitoring of motor rotor position is used to control the operation of the handpiece so the handpiece can provide the maximum amount of torque. In an alternative method of inductance sensing of rotor position, control console 32 is able to also provide precision speed regulation of the handpiece motor to 0 RPM.

Figure 31:
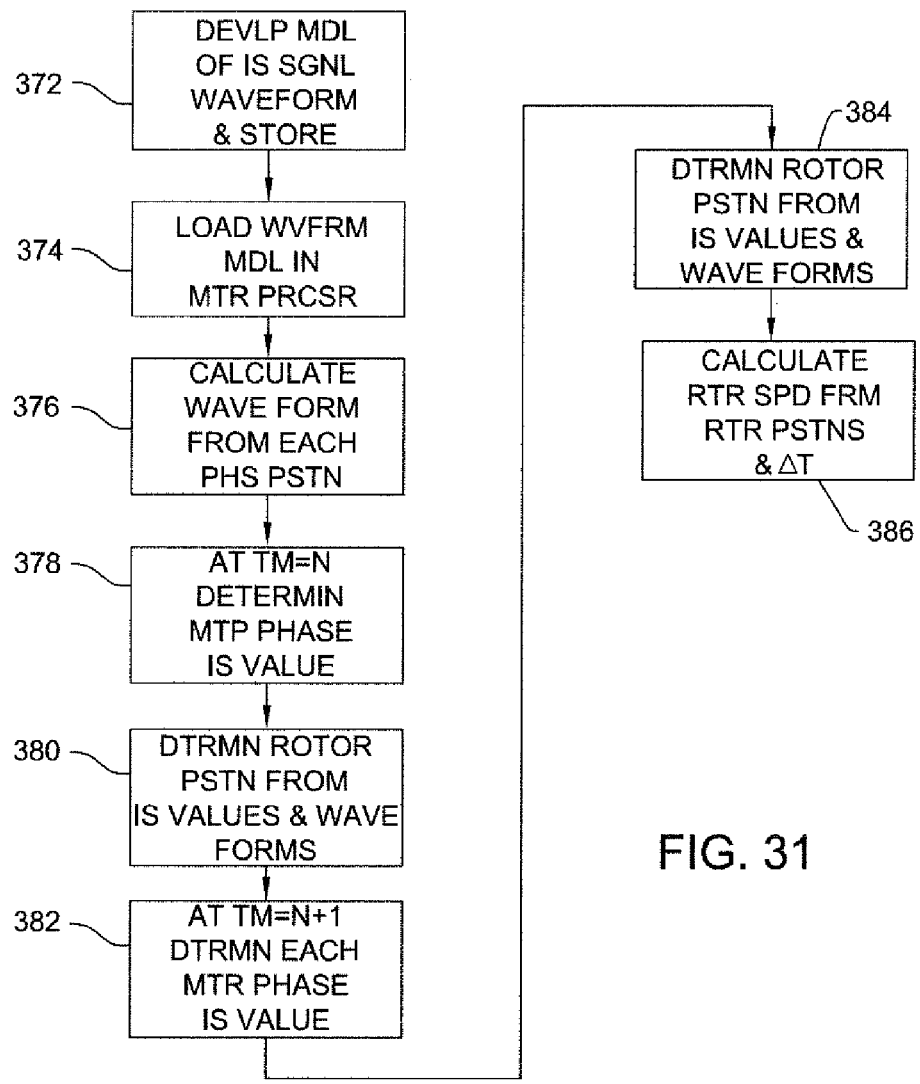
FIG. 31 is a flow chart of the process steps employed during handpiece manufacture and during operation of the system to user inter-commutation position calculations to, in inductance sensing mode, determine motor rotor position.

Specifically, in an alternative version of this invention, a mathematical model of the inductance sense signal profile for a single motor pole is developed, step 372 in FIG. 31. A Fast Fourier Transformation can be used to create this model. (It is understood that not all inductance sensed signals have the sine wave profile of motor poles depicted in FIG. 28. The coefficients describing this signal profile are stored in the handpiece NOVRAM, field 370 in FIG. 27. These data are provided to the motor processor 224 in the initialization packet, step 374.

Upon receipt of the data, the motor processor 224 uses the data describing the single signal profile to develop a table indicating for every degree of rotor position, the excepted inductance sensed signal for each of the motor phases, step 376. When the handpiece motor is in the inductance sensed mode, the calibrated and normalized inductance sensed signal values for each of the six motor phases are determined from the measured data, step 378. These six calculated values are then matched to the closest set of table values, step 380. Thus, the matching of step 380 serves to determine, based on the plural inductance sensed calibrated and normalized values, the angular position of the motor rotor.

Steps 382 and 384 are repeats of steps 378 and 380, respectively, at a later time. Based on the difference in determined rotor position from steps 380 and 384 divided by the time difference, motor processor 224 is the able in step 386 to determine rotor speed.

The above method of inductance sensed speed is employed at low speeds where the BEMF signals typically are not strong enough to facilitate precision speed control. Generally, low speed for this type of control is consider a speed of 15% or lower of maximum motor speed, and more often a speed of 10% or lower of maximum motor speed.

The method, inductance sensing for inter-commutation rotor position determination, can be used to determine rotor position for speeds down to 0 RPM.

The means by which system 10 of this invention monitors the BEMF signals is now explained by reference to FIGS. 34A and 34B. Line segment 440 of the plot of FIG. 34 illustrates the theoretical rise in the BEMF signal across the unenergized winding 234. Arbitrarily, line segment 440 can be considered the monitored BEMF signal across a first winding, the B1_SNS signal. Line segment 442 can be considered the monitored BEMF pulse across a second winding, the B2_SNS signal. Line segment 446 can be considered the monitored BEMF pulse across a third winding, the B3_SNS signal. The pattern then repeats.

In actuality, the changes in the switching of the commutation phases of the windings, a glitch is often present in the initial phase of a BEMF signal because of flyback currents. This is represented in by the down voltage glitch pulse 448 associated with line segment 442.

In order to avoid false determinations of rotor position based on these glitches, the FPGA BEMF monitor module 394 integrates the measured BEMF signals over time. More particularly, module 394 only integrates a particular BEMF signal starting from the time at which the signal is one-half through its rise or fall. Thus, with regard to the signal represented by line segment 440, BEMF monitoring module 394 only integrated the signal from the time represented by point 450. The BEMF signal represented by line segment 442 is only integrated from the time represented by point 452. The BEMF signal represented by line segment 444 is only integrated from the time represented by point 454.

The integrations of these BEMF signals are represented by the area under the integration curves in FIG. 34B. The BEMF monitor module 394 integrates each BEMF signal until a defined common threshold value is reached. This threshold value comes from the NOVRAM 72 in the initialization packet. This threshold value is represented by point 458 in FIG. 34B.

The time of the initial half way point for the initial BEMF signal, point 450 in FIG. 34A, comes from the commutation logic module 392. Module 392 also provides data upon which the time of second and third half way point, points 452 and 454, respectively, can be determined.

BEMF monitor module predicts when the next half way point, point 456 in FIG. 34A, according to the following process. Initially, module 394 determines when the peak integration value associated with the BEMF signal of line 440 occurs, point 458 on FIG. 34B. Then, the time at which the threshold value associated with the BEMF signal of line 442 occurs, point 460. The time between these two events is the actual time the BEMF signal of line 442 was at its true half way point. (For any given half-way time point of the BEMF signal, the difference between the predicted time and actual time is nominal.)

BEMF monitor module 394 determines the time at which the integration threshold value associated with the BEMF signal of line 446 is reached, point 462. Based on the time difference between the threshold values of points 460 and 462 occurred, module 394 determines the actual time, the BEMF signal of line 446 reached its half-way point. At this time BEMF monitor module 394 has in its memory data indicating when the signal of half way point 454 should have occurred and the time difference between when the half-way points of the transits of the BEMF signals of lines 442 and 446. BEMF monitor module 394 adds this time difference to the time at which the half-way transit represented by point 454 occurred. This sum is the prediction of when the BEMF signal represented by line 455 will occur, point 456. The BEMF monitoring module 394 thus starts it integration at this time.

In other versions of the invention, BEMF monitor module 394 may start integration before or after the half-way point of the BEMF signal transit. Generally though, switch glitches are over before this half-way point.

The half-way transit times of the transits of the later BEMF signals are repeatedly calculated in this manner. Thus, when the slope of the BEMF signals change as a result of speed changes of the handpiece motor 36, the predicted times of the half-way points of the signal's transits will similarly change. Thus, the half-way transit times predicted by the BEMF monitoring module, the times at which the module starts its integration process will, even with speed changes, closely approximate the true times.

It should be appreciated that the reason the signal is BEMF signal is integrated, as opposed to the monitoring of the occurrence of a zero crossing, is to eliminate false determinations of motor phase due to high frequency noise.

Figure 35A:
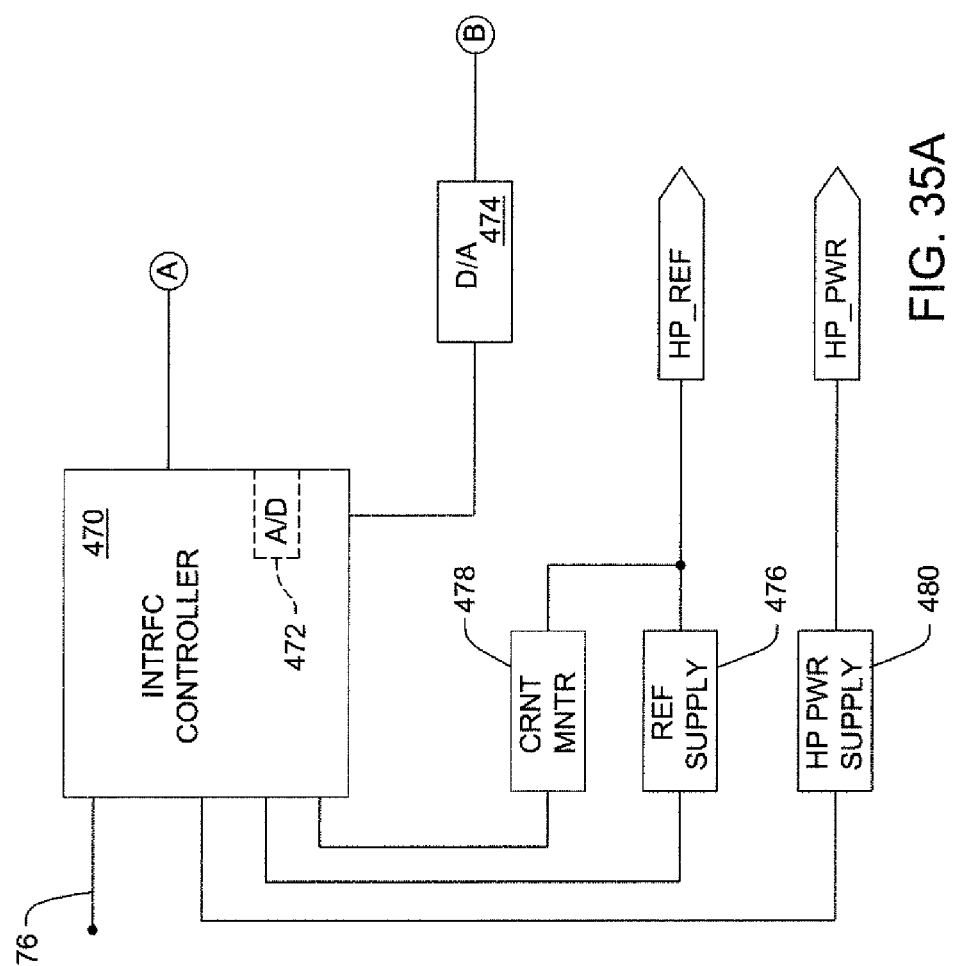
FIGS. 35A and 35B, when assembled together form a block and partial schematic diagram of the handpiece interface.
Figure 35B:
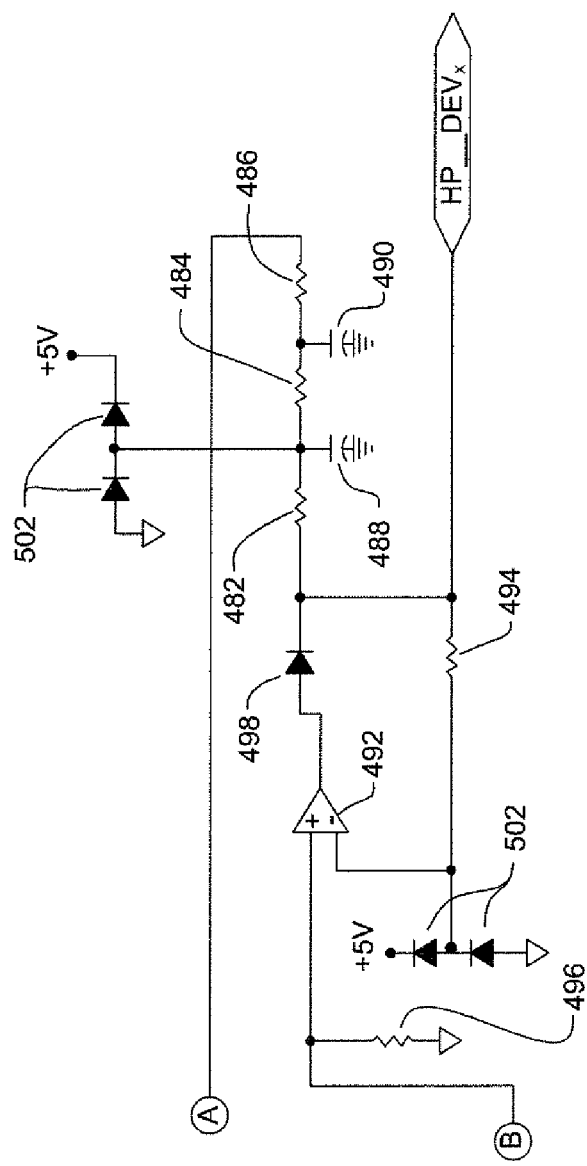

FIGS. 35A and 35B collectively illustrate the structure of a handpiece interface 70 of this invention. Interface 70 is able to connect to four devices integral with a handpiece 34 to which the interface is connected. For drawing simplicity, the connection circuit to only a single device, labeled the HP_DEVx connection is shown. Interface 70 is able to transmit and receive both analog and digital signals to each handpiece device to which it is connected.

Handpiece interface 70 includes an interface controller 470. One suitable interface controller 470 can be constructed from the ATmega8 microcontroller. Controller 470 has an internal analog to digital circuit 472 for digitizing analog signals received from the connected handpiece devices. Controller 470 serves as the interface between the connected handpiece 34 and the display controller over bus 76. Analog signals interface controller 470 outputs to any handpiece device are output in digital form to a digital to analog converter 474. One suitable converter 474 is available from the Texas Instruments Corporation.

Interface 70 has a precision voltage supply 476. Voltage supply 476 outputs a précising 5 VDC voltage to the handpiece 34, the HP_REF signal. This voltage is then available to any components internal to the handpiece that may require a precision voltage. A current monitoring circuit 478 monitors the current of the HP_REF signal. If this current exceeds a certain level, it is assumed that there is a fault internal to the handpiece. If this current level is detected, monitoring circuit 478 forwards a fault signal to interface controller 470. Interface controller 470, in turn, sends an appropriate fault message to display controller 64.

Upon receipt of the fault message, display controller 64 presents an appropriate warning on display 42. Display controller 64 also inhibits the actuation of the handpiece 34 based on any signals generated by the handpiece sensors, the on handpiece controls. This is because the high current HP_REF signal is assumed to indicate there is malfunction with these controls.

Handpiece interface 70 also includes a handpiece power supply 480. Power supply 480 provides a power signal to the handpiece, the HP_PWR signal. This signal is available to any device internal to the handpiece other than motor 36 that may need power. Such a device may be a transmitting unit that is part of surgical navigation system.

Analog signals from the handpiece device through the HP_DEVx connection travel from the connection through an RC filter that includes three series connected resistors 482, 484 and 486. This filter also includes capacitors 488 and 490. Capacitor 488 is tied between the junction of resistors 482 and 484 and ground. Capacitor 490 is tied between the junctions of resistors 484 and 486 and ground.

It is observed from FIG. 35B that the HP_DEVx connection is also attached to the inverting input of a buffer amplifier 492 through a resistor 494. The non-inverting input of buffer amplifier is connected to digital to analog converter 474. When the handpiece NOVRAM 72 data indicates analog signals are to be received from the connected device, based on instructions received from display controller 64, interface controller 470 configures the circuit. Specifically interface controller 470 causes digital to analog converter 474 to assert a signal to the non-inverting input of amplifier 492 that disables the amplifier. Since the amplifier is out of the circuit, signal flow is solely from the HP_DEVx connection to the RC filter.

The signal from the RC filter, the signal out of resistor 486 is applied to the controller analog to digital converter 472 for processing by the controller 470

In the event interface 70 is to output an analog signal to a handpiece device, controller 470 activates buffer amplifier 492. A digitized version of the signal is output from controller 470 to digital to analog converter 474. The analog signal produced by converter 474 is applied to the non-inverting input of buffer amplifier 492. Note a pull down resistor 496 is also tied between the non-inverting input to amplifier 492 and ground.

The analog signal out of amplifier 492 is applied through a diode 498 to the HP_DEVx connection.

Digital signals into interface 70 take the same conductive path from the HP_DEVx connection to controller 470 as the analog input signals. When digital signals are received, controller 470 disables its analog to digital converter 472. Consequently, the input signals are processed as digital signals.

Digital signals transmitted by the interface are transmitted by controller 470 through the controller terminal through which analog signals are normally received. The digital output signals thus pass through resistors 486, 484 and 482 to the HP_DEVx connection.

In FIG. 34B two zenner diodes 500 are shown reverse bias connected between the 5 VDC bus and ground. The junction between diodes 500 is connected to the junction between resistors 482 and 484. Two diodes 502 are similarly series connected and reverse biased between the 5 VDC bus and ground. Diodes 502 are connected at their common junction to the inverting input of buffer amplifier 492. Diodes 500 and 502 thus provide voltage protection for the interface.

In some versions of the invention a relay may be connected between the HP-DEVx connection and the interface circuit. This relay, when actuated, attaches the relay to the RFID interface 78. Thus, this relay is actuated to connect the HP_DEVx connection to the RFID interface 78 when the handpiece component is antenna designed to inductively exchange signals with a RFID associated with the handpiece.

It should be recognized that another feature of system 30 of this invention is that the display controller 64, motor controller 224 and the FPGAs 228 are totally reprogrammable. For example, by entering instructions through the 1394 Interface 68, the algorithms of the PID modules 406 and 414 can be significantly modified. Thus, one or more of the motor drive and sense circuits 210 can be reset to operate in a direct drive mode or provide open loop control. Similarly, one or more the motor drive and sense circuits 210 can be reprogrammed to supply the energization signals to a handpiece 34 with a power consuming component that does not include a motor. Such handpieces include RF ablation tools, light emitting devices, electracautery devices and devices that drive ultrasonic tissue forming accessories.

Further, system 30 of this invention is configured so that, when necessary, console 32 does not temporarily reduce the power supplied to one handpiece 34. In this version of the invention, handpiece NOVRAM 72 has a power sharing flag. This flag, when present, indicates that the handpiece can be operated in the manner described above wherein, if it appears the demands on the power supply 90 will start to exceed what it can provide, the power to the handpiece can be momentarily stopped in order to reduce the overall power drawn by the handpiece. Returning to FIG. 27, it can be seen that this flag is present/absent in a field 540. The state of the flag is read with the other data read from the handpiece NOVRAM 72.

In this version of the invention, the display controller 64 stores data indicating the maximum amount of power each attached handpiece could potentially draw. These data are stored in three fields 542a, 542b and 542c, represented by FIG. 36, associated with the display controller 64. Display controller 64 also stores data in a field 544 indicating at any instant, the potential maximum power that can be drawn by the currently actuated handpieces. For reasons that are apparent below, in versions of the invention with just two drivers 210, these data may simply be a pointer to the one field 542a, 542b or 542c associated with the currently active handpiece. In such a situation, the pointer has a zero value when no handpiece is actuated.

Figure 37:
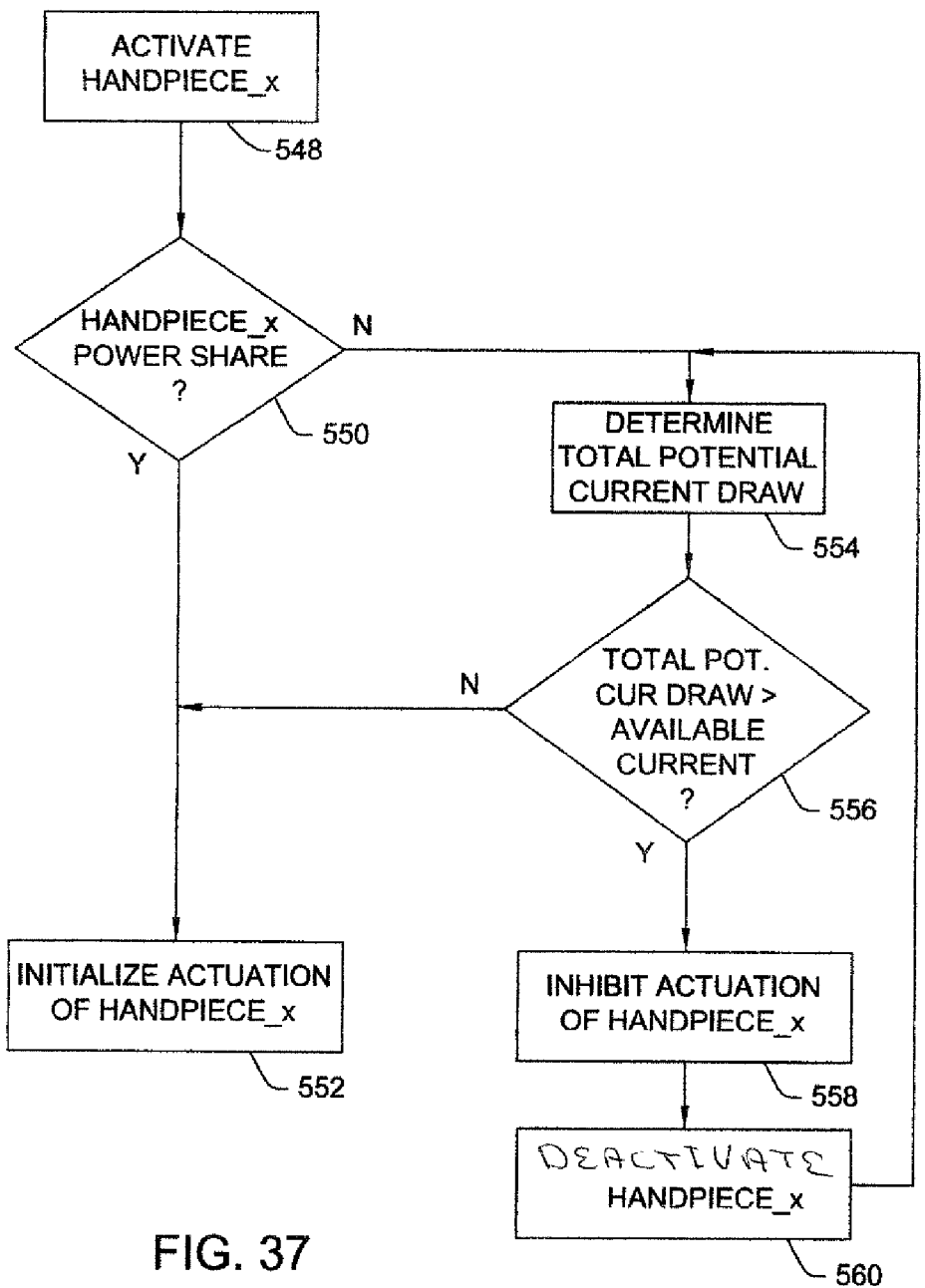
FIG. 37 is flow chart of process steps executed by the control console to regulate the actuation of surgical handpieces that may not be configured to perform power sharing.

The process by which the motor driver operates a handpiece that cannot be subjected to power sharing induced current interruptions is now explained by reference to FIG. 37. Initially, in a step 548, the display controller 64 receives an indication that the surgeon wants to use a particular handpiece_x. Based on the data read from the power sharing flag field 540 of the handpiece NOVRAM 72, display controller 64 determines if the handpiece power consuming module can be operated in the power sharing state, step 550. If the handpiece can be so operated, the display controller 64, in a step 552, sends a conventional initialization packet to the motor processor 224 so the handpiece can be actuated. Then, in the event the PSI_LMT signal is asserted, the power applied to the handpiece may be momentarily negated as described above.

However, if the flag in field 540 indicates the handpiece cannot be operated in the power sharing mode, the PSI limit module 430 proceeds to a step 554. In step 554, the PSI limit module 430 based on the data in field 544 indicating the maximum power the currently actuated handpiece/handpieces could draw and the data in field 542x indicating the maximum power this new handpiece determines the new potential maximum power draw for all handpieces. In a step 556 this power draw level is compared to the maximum power supply 90 could produce.

If the comparison of step 556 indicates that the total potential power the actuated handpieces could draw is within the amount the power supply can provide, step 552. Since, collectively, the amount of power the actuated handpiece could draw is less than the amount power supply 90 is capable of providing, there is no possibility that the PSI_LMT signal will be asserted. This means neither handpiece will have to be subjected to a power sharing operation.

Alternatively, in step 556, it may be determined that, potentially, the overall power that the handpieces, including the newly actuated handpiece, could draw exceeds the amount power supply 90 is capable of providing. In this event, the display controller does not output an initialization packet in order to start the process for energizing the new actuated handpiece. This non-event is represented by step 558. As part of the process of inhibiting the actuation of the handpiece, display controller 64 may generate a message stating why the handpiece was not actuated on display 42.

Eventually, the previously actuated handpiece is deactivated, step 560. Upon this event occurring, the display controller revises the data stored in field 542 to reflect the potential current drawn by the presently active handpieces. Again, if there are only two drivers 210, this current is zero.

Steps 554 and 556 are reexecuted. This time step 556 is executed. Display controller determines that the power supply 90 is able to supply all the power the handpiece not capable of power sharing will potentially draw. Therefore, step 552 is executed.

It should further be appreciated that a similar process is executed by the display controller 64 while a handpiece that cannot power share is being supplied with an energization signal. Here, steps identical to steps 554 are executed to determine if the power supply can supply the power the currently active handpiece may require. If the determination tests negative, even if the newly actuated handpiece can power share, display controller 64 inhibits actuation of the newly actuated handpiece. Actuation of the new handpiece remains inhibited until the handpiece not capable of power sharing is deactivated.

An advantage of this version of the invention is that it ensures that handpieces that should not be subjected to the momentary power limiting of the power sharing process are so power limited.

System 30 of this invention is further constructed to provide a programmed, current limited energization signal to certain heavy duty power consuming surgical handpieces 34. Often this type of handpiece is provided with an energization charge from a battery. While using a battery to provide power does offer advantages, one limitation is that the battery can only deliver the power stored within its cells. Once the battery charge is depleted, if continued use of the handpiece is desired, the surgical procedure is interrupted in order to remove and replace the battery.

Figure 38:
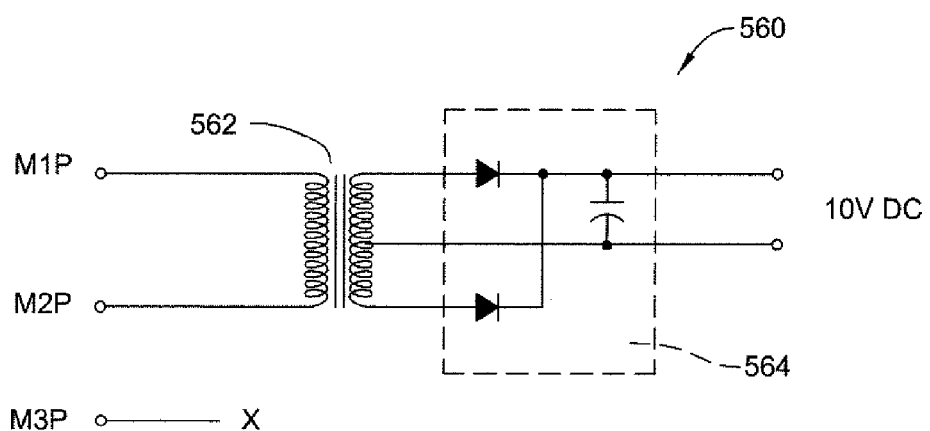
FIG. 38 is a schematic of how the components internal to a corded battery.

Thus, some surgeons prefer powering this type of handpiece with a device known as a "corded battery pack" 560 now described with respect to the schematic drawing of FIG. 38. Battery pack 560 includes a step down transformer 562. The M1P and M2P terminals from the H-bridge 212 are tied to the opposed ends of the primary winding of the transformer 562. A rectifier 564 is connected to the secondary winding of the transformer 562. The output signal rectifier 564 is a ripple-reduced DC energization signal. This signal is applied to the handpiece 34 to which the battery pack 560 is attached as the energization signal. Some battery packs 560 are designed to output a 10 VDC energizaiton signal.

Battery pack 560 does not employ either the power or ground connection that can be provided by through the H-bridge 212 M3P terminal. Therefore, during the application energization signals to battery pack 560, the M3P terminal is not connected to the battery pack 560.

Figure 39A:
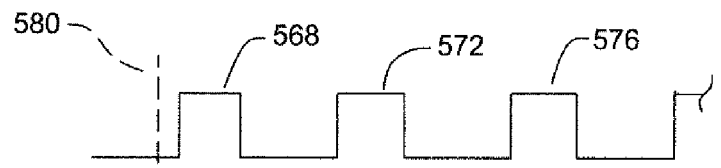
FIGS. 39A and 39B are timing diagrams of how power is pulsed to a component such as a transformer.
Figure 39B:
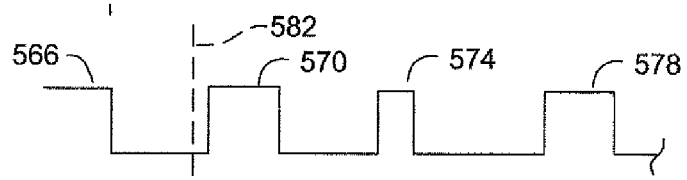

An energization signal is applied to alternatingly and sequentially establishing power and ground connections to the transformer winding through the H-bridge M1P and M2P terminals. FIGS. 39A and 39B illustrate the sequence in which these connections are established. FIG. 39A represents the H-bridge connections of one terminal, arbitrarily the M1P terminal, between the 40 VDC power line and ground. FIG. 39B represents the connections of the second terminal, arbitrarily the M2P terminal. Pulses 566, 570, 574 and 578 of FIG. 39B represent periods of time in which the 40 VDC power signal is applied to the transformer 562 through the M2P terminal. At these times, as represented by the waveform of FIG. 39A, the opposed end of the transformer 562 primary winding is tied to ground through the M1P terminal. Between the time periods in which the power signal is applied to the transformer 562 through the M2P terminal the power signal is applied to the transform through the M1P terminal. This is represented by pulses, 568, 572 and 576 of FIG. 39A. At these times, the H-bridge 212 established a ground connection between the transform primary through the M2P terminal.

It will further be observed that each disconnection of the transformer 562 from the 40 VDC power rail through a first one of the MxP terminals is not accompanied by a simultaneous connection to the power rail through the second MxP terminal. Instead there is a dead time between when the current flow is a first direction through the transformer 562 and when it starts to flow in the opposite direction. In FIG. 39A, the time between dashed line 580 (the time when pulse 566 ends) and the start of pulse 568, represents one of these dead time periods. In FIG. 39B, the time between dashed line 582 (the time when pulse 568 ends) and the start of pulse 570 represents a second dead time period.

While not illustrated, it is appreciated that corded battery 560 has a NOVRAM similar to handpiece NOVRAM 72. The data internal to the battery NOVRAM includes instructions indicating that, in order to provide an energization signal to the battery, only the M1P and M2P terminals of the associated H-bridge 212 are toggled between the power supply line and ground. As represented by FIG. 40, also internal to the corded battery NOVRAM are switching frequency and dead time data fields 588 and 590, respectively. Switch frequency field 588 contains data indicating the frequency at which the energization signal should be applied to transformer 562. Dead time field 590 contains data indicating the period of the dead time, $T_{DEAD\_TIME}$, between the successive periods in which the one end of the transformer primary winding is tied to the power supply line. These data are, like the other data retrieved from the battery NOVRAM, stored by the display controller 64 when the corded battery 560 is first attached to the control console 32.

When the display controller 64 sends an initialization packet to the motor processor 224 in order to start the application of energization signals to the corded battery, the switching frequency and dead time period data are included. Based on these data, the motor processor 224 determines the period in which each pulse 566-578 is to be asserted, $T_{PULSE}$. First, based on the switching frequency data, motor processor 224 determines the cycle time, $T_{CYCLE}$, for a single sequence in which the energization signal is to be applied to the transformer 562 from both the M1P and M2P terminals. The time period for each pulse is determined according to the following formula:

$$T_{PULSE}=0.5(T_{CYCLE}-2T_{DEAD\_TIME})$$

The $T_{PULSE}$ and $T_{DEAD\_TIME}$ values are then forwarded to the FPGA 228 responsible for applying the energization signal to the corded battery 560. Based on these data, the FPGA ensures that the opposed ends of the transformer windings are, through the M1P and M2P terminals, tied to the power supply rail and ground in the appropriate sequence.

This feature of system 30 of this invention makes it possible for control console 32 to apply the high powered energization signals needed by a transformer in the sequence that is best suited for that transformer. Such a transformer, in addition to be located in a device such as a corded battery, may also be contained within a powered surgical handpiece itself.

Figure 39C:
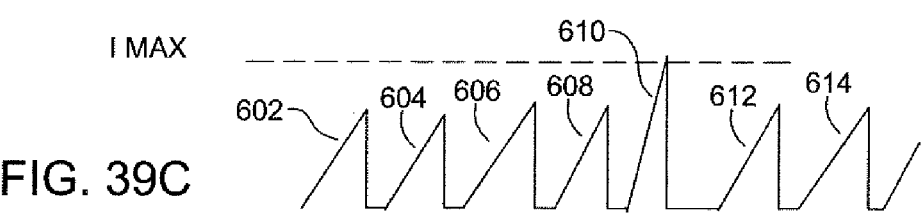
FIG. 39C is a waveform plot of the measurements of the current flow through the transformer when energized according to the pulse sequences of FIGS. 39A and 39B.

Control console 32 of this invention, also monitors and regulates the current drawn by transformer 562. Specifically, current flow through the primary winding of transformer 562 is monitored by monitoring the OVERLIP/OVERLIN version of the ISENSE signal. This signal is monitored by the FPGA module 419. FIG. 39C illustrates the current waveforms. This Figure comprises a number of waveforms 602-614. Each waveform 602-614 corresponds to the current flow through the transformer 562, during a separate one of the energization pulses 566-578, respectively. It is further observed that there is a small time gap between the start of one waveform 60-614 and the start of the subsequent waveform. This reflects the presence of the dead time time period between each energization pulse 566-578.

Returning to FIG. 40 it can be seen that the corded battery memory also contains a maximum current field 616. Field 616 contains data indicating a value representative of the maximum allowed current flow through the transformer. These data are part of the data also supplied to the motor processor 224 as part of the initialization packet.

Based on the data in the maximum current field 582, motor processor 224 determines a value for the maximum total current the transformer 592 should draw during a single energization pulse, $I_{MAX}$ of FIG. 39C. The module 419 continually monitors the level of the current waveforms 602-614 to see if any reach the $I_{MAX}$ level. In FIG. 39C, waveform 610, the waveform associated with pulse 574 of FIG. 39B, is shown as reaching the $I_{MAX}$ level. When this occurs, module 419 immediately opens the H-bridge MxP terminal through which the transform is tied to the power supply rail to ground. In FIG. 39B this is seen in that pulse 574 has a shorter period than pulses 566, 570 and 578. Module 419 continues to hold the MxP open through both the conclusion of the period in which the terminal would otherwise be tied to the power supply rail and the subsequent dead time period. Then, at the time normally scheduled the second MxP terminal is tied to the power supply rail. This is seen in FIG. 39A in that the time between the starts of pulses 572 and 576 is the same as the time between the starts of pulses 568 and 572.

Console 32 of this invention thus does more than apply power to devices such as transformer 562. Console 32 is also capable of ensuring that the amount of power provided to the device does not exceed the amount of power the device is designed to consume. Further in the event the device continually tries to draw power at the limits of ability to so consume power, the console will continue to provide the power at the frequency at which it should be provided to the device.

Figure 41:
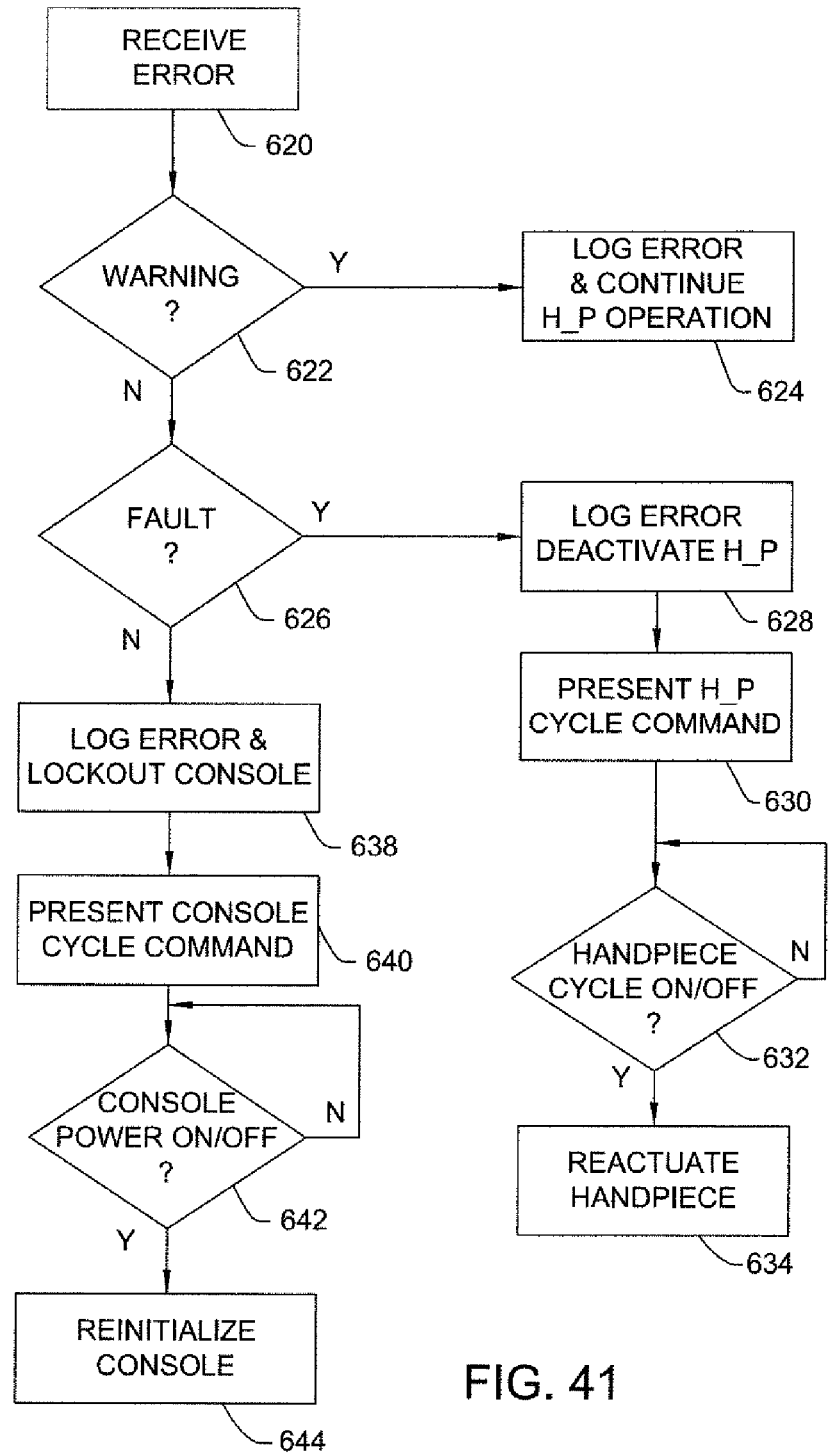
FIG. 41 is a flow chart of the process steps executed by the control console when the console receives in indication that a abnormal event, an error, occurred during the actuation of a handpiece.

Control console 32 of this invention is also configured to respond to out of bounds events that occur during the actuation of a handpiece 32 as function of the severity of the event. FIG. 41 is a flow diagram of how the console responds upon receipt of information regarding the occurrence of an event, called an error. In a step 620 the motor controller 86 reports the occurrence of the error, and a code identifying the type of error to the display controller. In a step 622, display controller 64 determines if the error is the lowest form of error a "warning". This type of error is the type of event that does not damage either the console 32 or the handpiece 34. One such warning-type error is the handpiece 34 drawing more power than it is intended to draw. If, in step 622 it is determined the error is a warning-type error, the display controller, in a step 624, logs the occurrence of the error. The display controller does not cause operation of the handpiece to be interrupted.

The next higher level error is a "fault" error. This type of error could potentially cause immediate damage to the console or handpiece. Examples are fault-type errors are the voltage across the handpiece power-consuming unit appreciably dropping or a divide-by-zero event occurring in the motor controller 86. Step 626 represents the display controller 64 determining, based on the error code, if the occurred error was a fault error. If the error is a fault error, in a step 628, the occurrence of the error is logged. Also shown as part of step 628 is the deactivation of the handpiece associated with the error.

In a step 630, the display console presents on the display 42 data indicating that an error occurred and that for the handpiece to be restarted, it must be cycled off and then back on. Step 632 represents the waiting for the cycling of the switch used to regulation actuation to occur. Once the handpiece control switch is so actuated, the display controller 64 allows the handpiece to be reactuated, step 634.

If an error is neither a warning nor a fault, it is the most serious type of error, a lockdown error. An example of such an error is a disabled FET 242, 244 or a stuck relay 304, 306. If the tests of steps 622 and 626 are both false, then, by default, the error is a lockdown error. In this case, in a step 638 the display controller 64 logs the error. As further represented by step 638, display controller 64 prohibits energization of any of the handpiece attached to it. Display controller 64 also presents an appropriate image on display 42 informing the surgical personnel of the error. The surgical personnel are invited to clear the error by cycling the console by power down and then powering the console back up. Step 642 represents the console 32 waiting for this event to occur. Step 644 represents the subsequent reinitialization of the console 32. (Most likely though, lockdown-type error is due to a hardware problem that cannot be remedied by off and on cycling of the console.)

Console 32 is thus further designed so that, the action taken in response to the occurrence of an error is a function of the severity of the error. Minor errors do not result in the interruption of the actuation of the handpiece that may have been the source of the error. The console gives surgical personnel the opportunity to determine if a mid-level error can be corrected by the momentary cycling off and on of the handpiece. Only if a major error occurs does the console require a complete power down and powering back up of the console.

Moreover, the console logs when the error occurred, the type of error and the handpiece with which the error is associated. This provides maintenance personnel with the ability to identify the sources of certain errors.

When a handpiece is operated in a oscillate mode, control console 32 of this invention regulates the period in which the motor 36 is to be run in any given direction as both a function of motor rotation and time. By way of background it should be understood that some surgical handpieces such as shavers are operated in oscillate mode. In this mode the motor 36 and attached cutting accessory 35 are actuated in a first direction and then in the reverse direction. The cycle is then repeated. This movement is desirable so that the cutting accessory 35 can, over time, excise the section of the tissue against which the accessory is applied.

Figure 42:
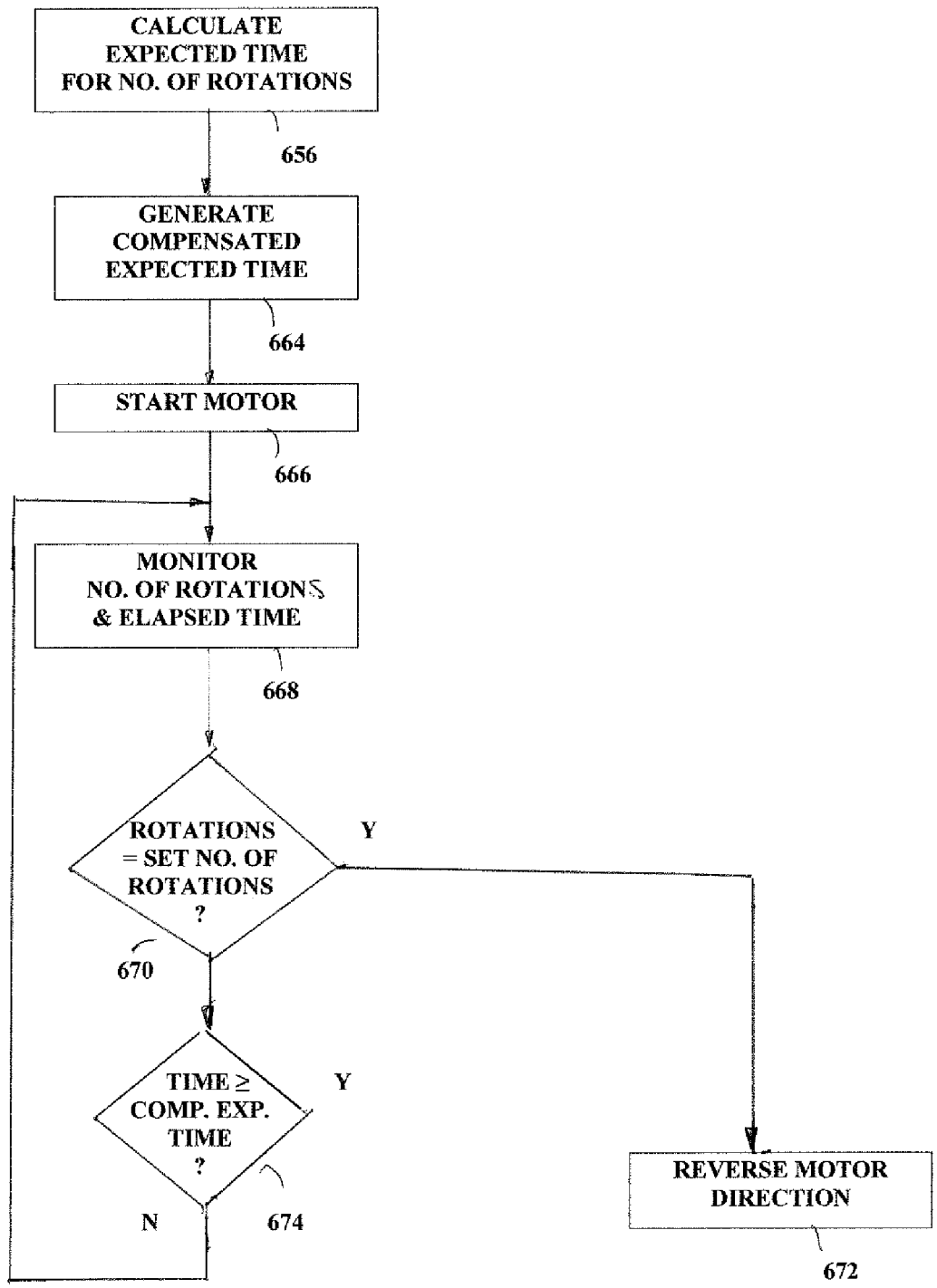
FIG. 42 is a flow chart of the process steps that are executed in order to control the period of time a handpiece motor is actuated to run in any given direction when the handpiece is run in the oscillate mode.

The process by which motor processor 224 regulates for how long the motor is actuated to run in a given direction, when the motor is run the oscillate mode is now described by reference to the flow chart of FIG. 42. In an initial step 656, motor processor 224 makes a basic determination of the period it should take the motor 36 to make the necessary number of shaft rotations. The input variables into this determination are: the number of rotations the motor shaft should turn in a given single direction cycle; the speed at which the motor shaft rotates; and motor acceleration rate. These inputs variables are based on the default settings for the handpiece based on any adjustments by the surgeon. These adjustments may include the speed setting set for the handpiece when it is to be driven in the oscillate mode.

Figure 43:
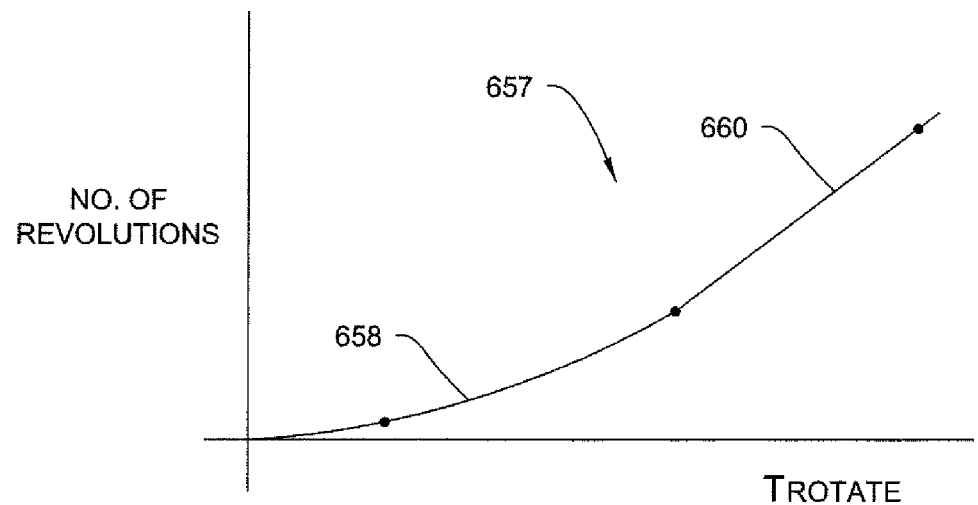
FIG. 43 is a graphical representation of number of rotation, over time, a motor undergoes in a single direction when driven in the oscillatory mode.

Plot 657 of FIG. 43 graphically illustrates how the above variables are used to determine expected actuation time. The initial portion of the plot, curved segment 658, represents that extent of rotation, the number of rotations of the motor rotor over time as it accelerates from a zero speed state to a set speed state. Linear segment 660 of plot 657 represents the number of rotations of the motor over time when in the set speed state. Thus, based on data describing these variables and the number of rotations the motor rotor should turn, motor processor 224 determines the total time the motor should be actuated in order to make the expected number of rotations, $T_{ROTATE}$.

Once $T_{ROTATE}$ is calculated, in a step 664, display controller multiples the time period by a compensation factor to determine a compensated rotation time $T_{COMP\_ROTATE}$. This compensation factor is greater than unity. In some versions of the invention, this factor is stored in a field 665 in the handpiece NOVRAM 72 (FIG. 27). This compensation occurs because the resistance of the tissue being cut can slow the time it takes the motor rotor to turn.

In a step 666 the motor is actuated. In a step 668, the display controller 64 monitors both the number of rotations the motor rotor undergoes. It is understood the rotation count is monitored by counting the number of commutations through which the windings 234 are cycled. Also in step 668, display controller 64 monitors the time the motor is actuated. In a step 670, the display controller 64 determines if, based on the monitoring of step 668, the motor rotor has undergone the set number of rotations. If the evaluation of step 670 tests true, in a step 672 display controller stops the motor and reverses the direction of motor rotor rotation. The sequence is then repeated.

If the evaluation of step 670 tests false, in a step 674, display controller tests to determine if the time the motor is actuated is equal to or greater than the compensated rotation time. If this tests negative, steps 668, 670 and 674 are reexecuted.

However, if in step 674, display controller 64 determines that the motor has run for more than the compensated expected time in a single direction step 672 is executed.

Thus, in the event an oscillating cutting accessory, such as shaver, abuts a section of tissue that is difficult to excise, the accessory does not become stuck against the tissue. Instead, system 30 of this invention is constructed so that when the cutting accessory is subjected to this obstruction, the accessory changes directions. This increases the likelihood that the repetitive oscillation of the cutting accessory against the opposed sides of the obstructive tissue is, over time, able to excise the tissue.

System 30 of this invention is further constructed so that during the initial period at which an energization signal is applied to a handpiece motor 36 in order to actuate the handpiece, the handpiece is able to develop torque above its normal limits.

Normally, as described in the incorporated by reference U.S. Pat. No. 6,017,354, the amount of torque a handpiece is allowed to draw at any instant is a function of motor speed. Generally, there is an inverse relationship between the instantaneous speed of the handpiece motor and instantaneous amount of torque the handpiece is allowed to develop. At start up, owing to the presence of body fluids and small bits of tissue, the components of a cutting accessory may be subject to an appreciable amount of static friction. Also, at start up, tissue immediately adjacent the cutting accessory may place a significant amount of resistance on the movement of the cutting accessory. The presence of either of both of these conditions mean it is necessary for the handpiece motor to, at start up, deliver an appreciable amount of torque in order to be able to move the cutting accessory from its at-rest position. However, if the control console limits the amount of torque the handpiece motor 36 is allowed to develop, the console may not provide the handpiece motor with the power required to initially displace the cutting accessory.

System 30 of this invention overcomes this potential inhibiting of handpiece actuating by, for a limited time after the start of the application of the energization signal, allowing the motor to 36 produce more torque, draw more current, than the motor is otherwise allowed to draw. The amount of additional torque the motor is allowed to draw is obtained from a start up torque field 678 (FIG. 27) in the handpiece NOVRAM 72 memory. The time period in which the motor is allowed to produce this excess torque is obtained from a start up torque time out field 680, $T_{TRQ\_TIME\_OUT}$. Typically the period in which the motor is allowed to develop a higher initial torque is between 10 milliseconds and 1 second after start up. In some methods of this invention, this start up period may last up to 3 seconds.

Figure 44:
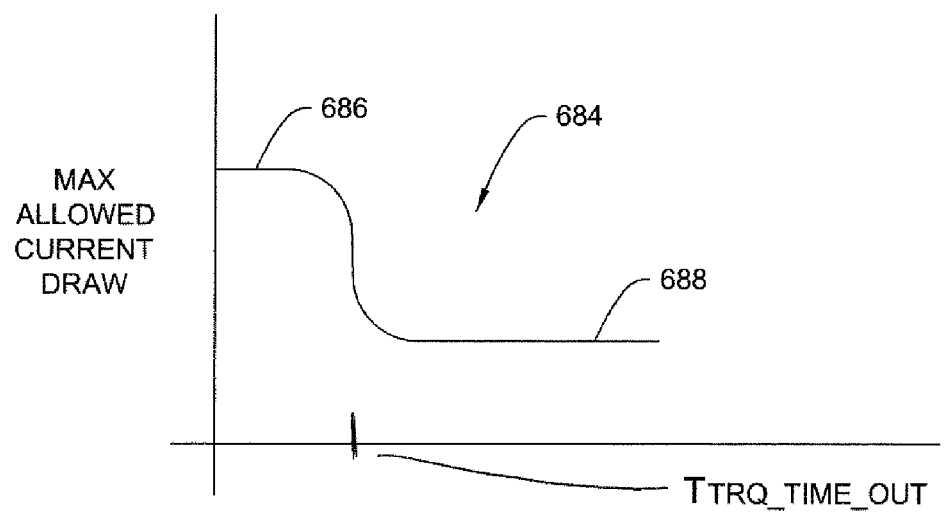
FIG. 44 is a graphical representation of how, immediately after zero speed start up, a handpiece motor energized by the console of this invention is allowed to produce a relatively high amount of torque, draw a relatively large amount of current.

Plot 684 of FIG. 44 graphically represents this relationship. Line segment 686 graphically represents the maximum amount of current the handpiece motor is allowed to draw, the torque the motor is allowed to develop, immediately after the energization signal is first applied. After time $T_{TRQ\_TIME\_OUT}$, the amount of torque the handpiece is allowed to develop drops to a lower level, represented by line segment 688. This permitted boost of power output occurs because, before time limiting occurs as a result of the display controller, after time $T_{TRQ\_TIME\_OUT}$, in the initialization packet and subsequent speed set-point packets, the display controller sends the motor processor 224 data indicating that the handpiece can draw the higher current. After time, $T_{TRQ\_TIME\_OUT}$, the display controller forwards speed-set point packets with current limits that are a function of motor speed.

Figure 45:
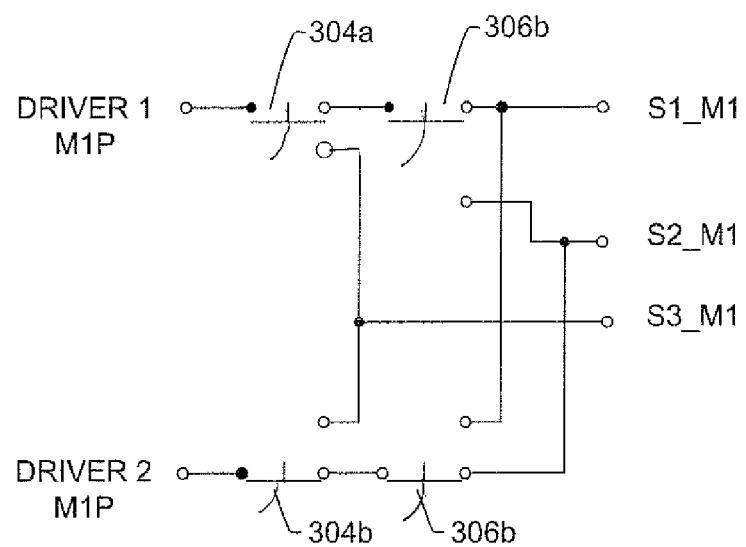
FIG. 45 is a diagrammatic illustration of the connections established by the multiplexer relays'

Control console 32 is further configured to preposition the relays 304 and 306 internal to the multiplexer 222. The configuration of the relays is seen in the diagrammatic view of one set of relays presented in FIG. 45. Here, relays 304a and 306a are shown as the relays that establish the connection from the Driver 1 M1P terminal to the M1 connections of the sockets S1, S2 and S3. Relays 304*b* and 306*b* are shown as the relays that establish the connection from the Driver 2 M1P to the same socket M1 connections. Here it can be seen that the states of relays 306*a* and 306*b* are reversed. When relay 306*a* is in the static state, it establishes a connection to the M1 connector of the S1 socket. When relay 306*b* is in the static state, it establishes a connection to the M1 connector of the S2 socket. This ensures that, at boot up, the drivers are not connected to each other.

Figure 46:
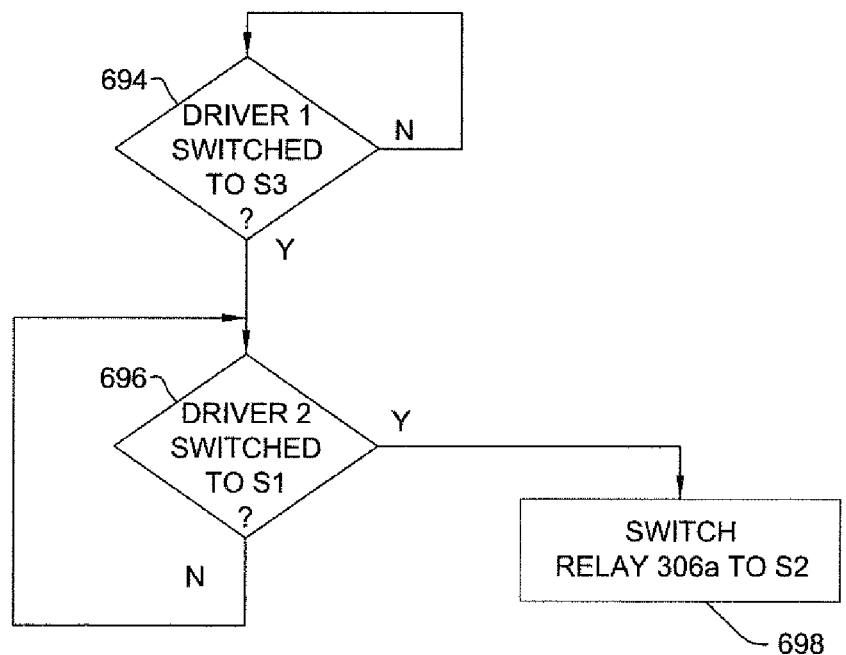
FIG. 46 is a flow chart of the sequence in which the multiplexer relays are switched.

FIG. 46 is flow chart of the relay sequencing of console 32. In a step 694, the motor processor 224 determines whether or not the relay 304*a* associated with Driver 1 has been switched to established a connection to socket S3. Motor processor 224 continues to monitor the Driver 2 to determine which of the remaining two sockets, S1 or S2, to which it is connected. More particularly, the motor processor monitors Driver 2 to determine if it is connected to or becomes connected to socket S1, step 696. If Driver 2 is o becomes connected to socket S1, in a step 698, motor processor causes the FPGA that is part of Driver 1 to automatically actuates relay 306*a* so the rely is tied to socket S2.

If relay 306*a* was not so prepositioned, the following events would happen if Driver 1 was next immediately used to actuate the surgical handpiece 34 attached to socket S2. Relays 304*a* and 306*a* would switch to establish this connection. If relay 304*a* establishes resets before relay 306*b* resets, then, momentarily, both Driver 1 and Driver 2 are connected to socket S1. This could result in the energization signal output by Driver 2 being applied to Driver 1. Clearly, such signal flow could potentially damage the control console 32.

However, the above switching process of the control console 32 of this invention avoids the possibility of this event. Because of the execution of step 698, relay 306*b* is already connected to socket S2. Thus, when the Driver 1 receives a command to switch from energizing the handpiece attached to socket S3 to the handpiece attached to socket S1, the resetting of relay 304*a* immediately establishes the appropriate new connection. There is no possibility the multiplexer connection will establish a momentarily and potentially damaging connection between Driver 1 and socket S1.

It should be understood motor processor 224 practices variations of the process of the flow chart of FIG. 46 for the remaining MxP to Mx connections. Thus, if Driver 2 is switched to socket S3, the motor processor 224 monitors whether or not Driver 1 is connected to socket S2. If this evaluation is positive, relay 306*b* is connected to socket S1. Thus, in the event the Driver 2 is to next apply an energization signals through socket S1, only relay 304*b* needs to be switched. The possibility that the cycling of relays 304*b* and 306*b* will cause Driver 2 to momentarily be connected to socket S2, (while Driver 1 is connected to the same socket,) is eliminated.

Control console 32 of this invention is further configured to, when a handpiece motor 36 is decelerated between a first speed and a second, lower speed, apply braking signals to the motor. Specifically, in this version of the invention, the algorithm employed by the SC PID module 406 outputs signals, based on actual speed and the speed set point, that vary from 100% (full acceleration) to −100% (full braking).

Figure 47A:
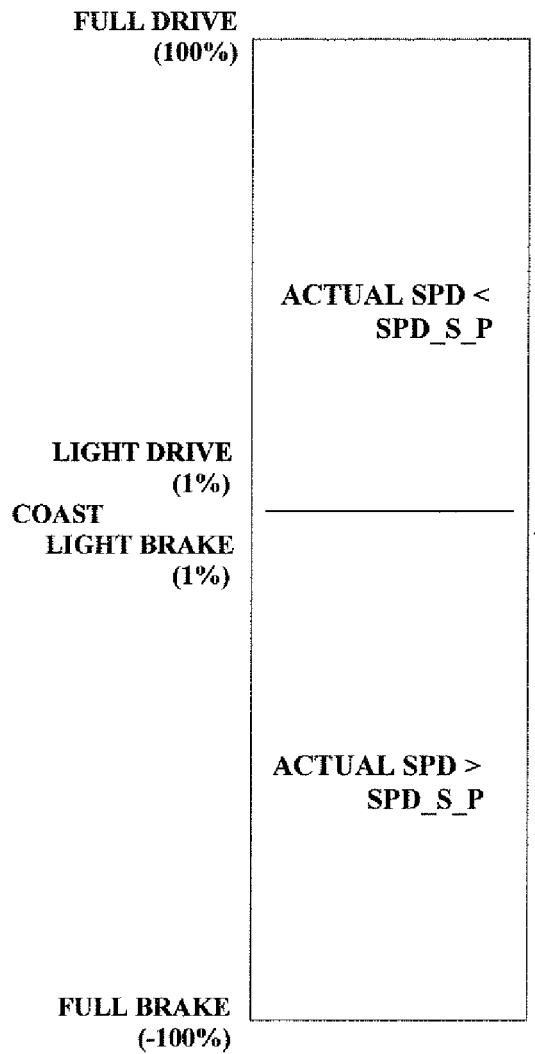
FIGS. 47A and 47B generally represent the different speed states analyzed by the speed control PID module and the potential output commands the module generates as a function of the speed state.

FIG. 47A illustrates one method of outputting braking signals according to this invention. Specifically, in states when the actual speed of the handpiece motor 36 is less than the speed set point, the speed control PID module 406 outputs drive signals to cause the acceleration of the motor. The exact type of drive signals, light, full or in between, are a function of the difference between the actual speed and the speed set point. When the actual speed of the motor 36 is greater than the set point speed, the speed control PID module 406 outputs signals to cause anywhere from light to full braking of the motor. Again, it should be understood that when there is only a small difference in the two speeds; command signals that cause the light braking of the motor are generated. As the difference between the actual speed and set point speed increases, speed control PID module 406 outputs command signals to cause the fuller braking of the motor 36.

In this version of the invention, only when actual motor speed matches the set point speed does the speed control PID module output coast signals. These are signals that cause neither energization signal nor braking signal connections to be made to the motor winding. Instead, as is implied, the motor is allowed to coast.

Figure 47B:
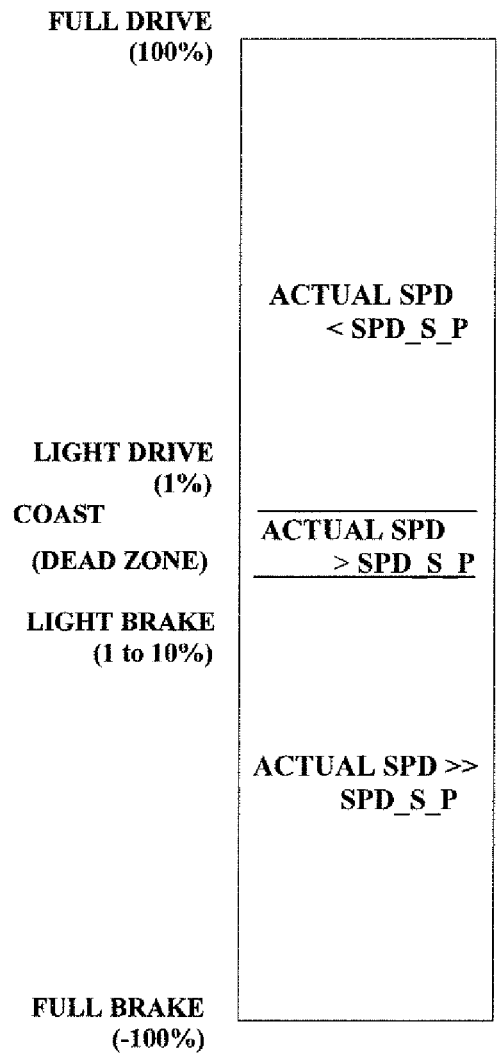

FIG. 47B illustrates a second process for determining when braking command signals are asserted. In this process, when the handpiece motor is in a state wherein the motor speed is slightly less the set point speed, the motor is allowed to coast. Thus, in the event the surgeon only slightly reduces the motor speed, the speed control PID module 406 generates signals that allow the motor to coast to the new, lower speed. This allows for an even deceleration of the motor that it may be difficult to accomplish if the motor rotor is braked.

In situations however, where there the motor speed is appreciably greater than rotor speed, speed control PID module asserts the command signals to cause braking as before.

It should also be understood that in both processes the braking command signals module 406 when light braking signals may very. In some versions of the invention, illustrated by FIG. 47A, the initial light braking command signals cause the smallest amount of braking the console can apply. As illustrated by FIG. 47B, the speed control PID module when generating light braking signals may generate command signals that cause more than the smallest amount of braking. This is especially desirable when, as in the process of FIG. 47B, there is appreciable difference between motor actual speed and the speed set point.

Data read from the handpiece NOVRAM, (data not illustrated), can contain instructions for determining: which process the speed control PID uses to generate drive and braking signals; the extent of any speed dead zones in which neither drive or braking command signals are to be produced; and the type of command signal, light/intermediate/full, that is to be generated as a function of the difference between actual motor speed and the set point speed. It should further be understood that the amount of braking applied is gradual, not a stepped amount.

It is also appreciated that the fact the motor actual speed is above the speed set point does not, in all cases cause the speed control PID module to output signals that cause the motor to either coast or be subjected to braking. For example, in the event the surgeon sets the handpiece speed to operate at a speed set point slightly lower than actual speed, the speed control PID module may respond by reducing the output signal from 30% to 20%. In this event there is neither coasting nor braking. In situations where the motor actual speed is appreciably above the speed set point, the speed control PID module will generate signals to cause coasting the 0% signal, or braking signals <0%. The extent of compensation the speed control PID module performs is a function of the tuning constants loaded into the module for the handpiece and the system dynamics.

During the time period the handpiece motor 36 is being braked, motor speed is monitored. This monitoring is performed to determine if the actual motor speed has dropped to sufficient level that the level of braking can be first, reduced and then, totally stopped. Motor speed during braking is performed by sequentially monitoring the current flow through the windings 234. Specifically, each MxIP/MxIN-based ISENSE signal functions as a measure of the current flow through the associated winding 234 when the motor is being braked and the motor rotor is rotating.

Figure 48:
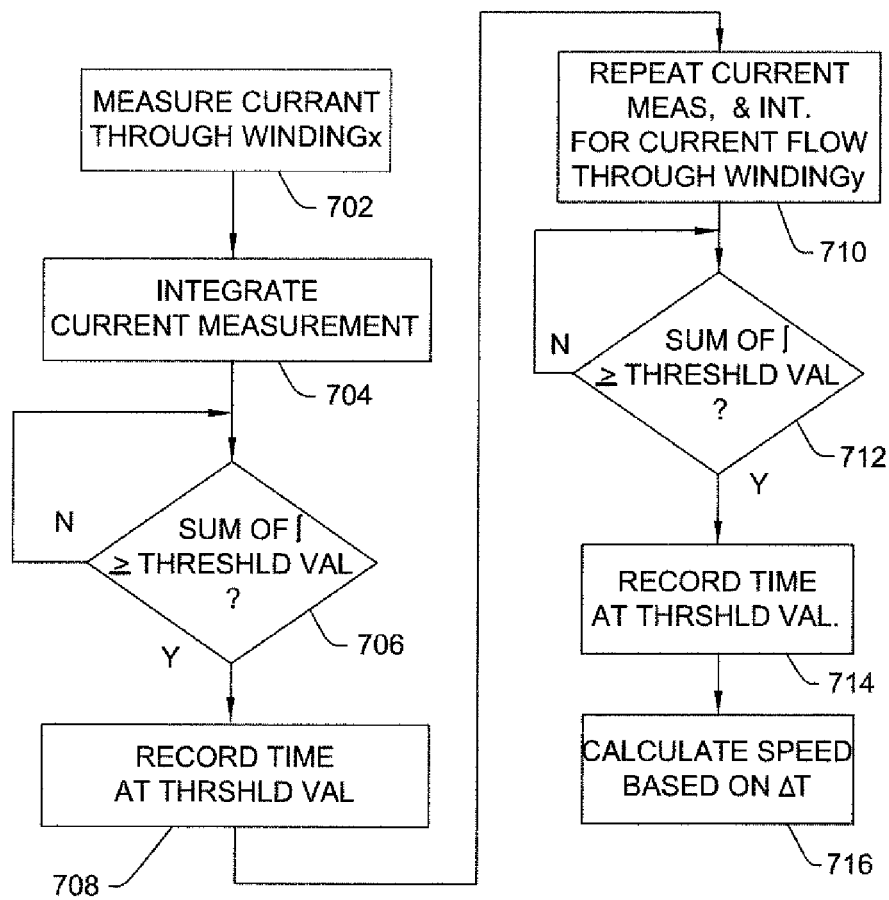
FIG. 48 is a flow chart of how, during the braking of handpiece motor, rotor speed is dynamically determined.

FIG. 48 thus illustrates the process by which the MxIP/MxIN-based ISENSE signals are measured to determine rotor speed during the braking process. In a step 702, the BEMF monitor module 394 or a functionally similar module starts measuring one of the MxIP/MxIN-based ISENSE signals; arbitrarily for this example the M2IP/M2IN ISENSE signal. In a step 704 the BEMF monitor 394 starts integrating the ISENSE signal at a time after the signal is started to be monitored. As with the BEMF monitoring itself, this delay is to minimize false integration results due to the presence of flyback currents. The output of this integration is thus essentially identical to the waveform of FIG. 34B.

Eventually, the sum of the integration reaches a threshold value, point 458 of the waveform of FIG. 34B, step 706 of flow chart of FIG. 48. In a step 708 the time this threshold value is recorded. In a step 710, the processes of steps 702 and 704 are repeated for a second winding, arbitrarily the M3IP/M3IN ISENSE signal. In a step 712 the sum of the second integration reaches the threshold value, point 460. In a step 714, the time the threshold value. Then based on the difference in times in which the threshold values are reached, motor speed is calculated.

Control console 32 of this invention thus provides a means, other than coasted deceleration, for the motor to be slowed from a first speed to a second speed.

Figure 49A:
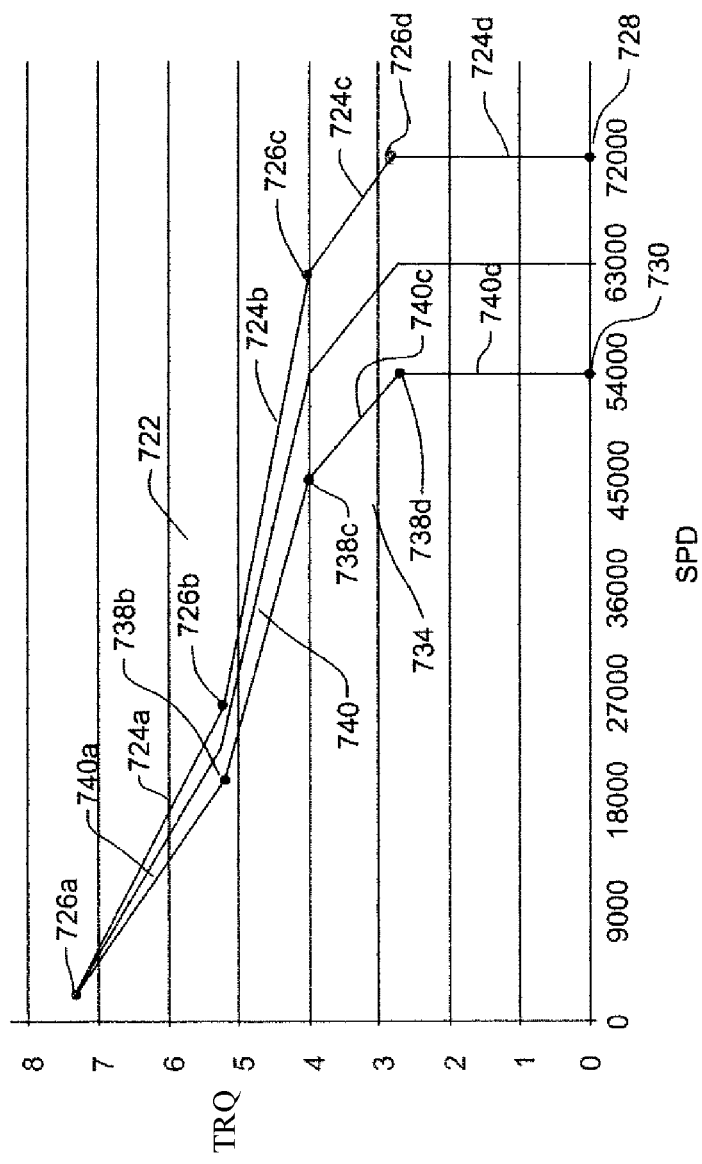
Figure 51:
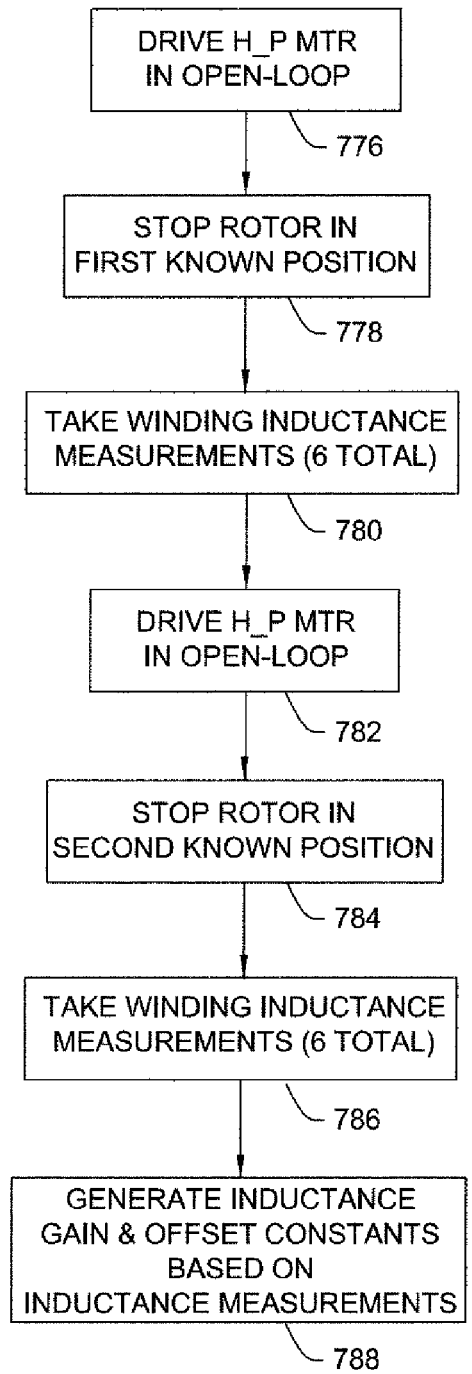
FIG. 51 is a flow chart of the process steps executed by the control console to perform inductance sensing self adjustment.

Control console 32 also scales the torque set point profile of the handpiece motor 36 as a function of any surgeon selected scaling of handpiece speed. This process is understood by initial reference to FIG. 49A. Here plot 722 represents the maximum torque the motor is allowed to develop at any given speed for the maximum allowable motor speed. The actual line segments 724a, 724b, 724c and 724d forming plot 722 are based on four torque/speed set point values retrieved from the handpiece NOVRAM 72 (data fields not illustrated) and the maximum speed of the handpiece. In FIG. 49A, points 726a, 726b, 726c and 726d represent the torque/speed point values. In FIG. 49A, point 728 on the X-axis represents the maximum operating speed of the handpiece motor There are times when the surgeon decides to set the maximum operating speed to a set speed, for the handpiece motor 36 to a speed less than the maximum operating speed. Point 730 on the X-axis represents the resetting of the motor set speed to a speed lower than the maximum operating speed.

When the motor set speed is so reset, display controller 64 generates a torque set point profile. For a given actual motor speed, ACT_SPD, this process starts with the calculation of motor speed percent:

SPEED_PCT=ACT_SPD/MAX_SPD

Here MAX_SPD is the actual speed at which the motor can run. A set speed percent, SET_SPD_PCT is then found using the formula

SET_SPD_PCT=SET_SPEED/MAX_SPD

Here SET_SPEED is the user set maximum speed. A constant α is then calculated according to the formula:

$$\alpha = \frac{SET\_SPD\_PCT - MAX\_FXD\_PCT}{100 - MAX\_FXD\_PCT}$$

Here, MAX_FXD_PCT is the last fixed point of the torque speed plot of the handpiece. For the plots of FIG. 49A, this is point 726a. This value comes from the torque speed plot data read from the handpiece NOVRAM 72.

A MAP_SPD_PCT value is then calculated according to the following formula:

MAP_SPD_PCT=MAX_FXD_PCT+α·(X−MAX_FXD_PCT)

Variable X is a percent from the root plot 722 of FIG. 49A of the speed that is being down adjusted. Thus, to calculate the speed for point 738b variable X is calculated according to the formula:

X_PNT738b=SPD_PNT726b/SPD_PNT728

Here it is understood SPD_PNT_728 is the MAX_SPD. Once the MAP_SPD_PCT is calculated, the speed at the point is calculated by multiplying this later percentage by the speed from the corresponding plot point. Thus, the speed at point 738b, SPD_PNT_738b is calculated according to the following formula:

SPD_PNT738b=MAP_SPD_PCT·SPD_PNT726b

The speeds of the subsequent points 738c and 738d are similarly mapped from the speeds at points 726c and 726d, respectively.

Based on these new mapped speed points line segments 740a, 740b, 740c and 740d are generated to develop plot 734, the new torque set point profile for the set point speed of point 730.

In this invention, when a surgeon runs a motor at a reduced maximum speed the motor reaches its torque limit sooner than it would without the torque mapping of this invention. As a result, the motor speed starts to slow sooner than this action would otherwise occur. This feature of the invention provides the surgeon with feedback, that appreciable torque is being applied to the surgical site, sooner than the feedback would otherwise be received. This enables the surgeon to, while operating the handpiece 34 at lower than the highest speeds, adjust motor speed to ensure that the handpiece, without stalling places output the maximum amount of force it can in order to perform the desired surgical procedure.

FIG. 49B is an alternative scaled torque map that can be produced by this invention. Plot 750 is identical to plot 722 of FIG. 49A. Plot 752 is the torque speed plot for the initial reduced maximum speed setting. Here, both points 726a and 726b are the fixed points of the scaled torque maps. Thus in order to map the additional reduced speed torque speed set points the speed at point 726b is used as the MAX_FXD_PCT.

Thus, line segment 724a forms part of plot 750, plot 752 and the torque/speed plots of the other reduced speed settings. Plot 752 is completed by calculating the value for adjusted speed set points 754a and 754b using the above algorithms. Line segment 756b of plot 752 is plotted between point 726b and point 754a. Line segment 756c is plotted between points 754a and 754b. Line segment 756d is equivalent to line segment 740d of plot 734.

It should be appreciated that in the plural fixed point torque map scaling represented by FIG. 49B, at very low maximum speeds. When the motor is run at the maximum speed, the handpiece may be able to generate appreciable amounts of torque until close to the stall speed. Plot 760, which comprises line segments 724a and 762 represent this type of torque/speed relationships.

The number of fixed points in the scaled torque maps are based is based from data read from the handpiece NOVRAM 72. Alternatively, the surgeon is allowed to custom set this factor.

Figure 50:
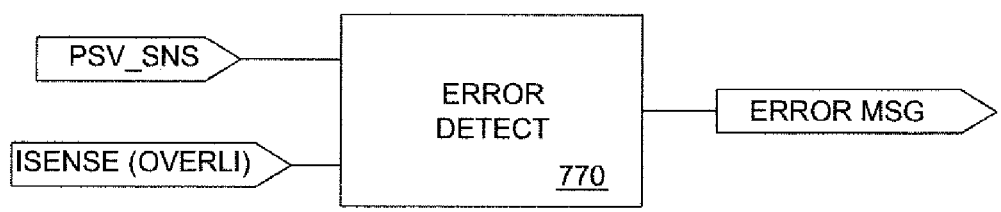
FIG. 50 is a block diagram of the inputs and output of the error detect module internal to a field programmable gate array internal to one of the motor drivers of the control console.

Control console 32 of this invention is further constructed to monitor handpiece voltage drops and current draws to ensure the system 30 is properly functioning. An error detect module 770, shown as a separate element in FIG. 50 though understood to be part of the FPGA 228, monitors both the PSV_SNS signal and the OVERLIP/OVERLIN-based ISENSE signal. While the handpiece is actuated, error detect module 770 continually monitors the PSV_SNS signal to evaluate if the signal drops, from the to power supply voltage to below a cutoff voltage level. In the version of the invention wherein the power supply voltage is 40 VDC, the cutoff voltage level is 30 VDC. If the power supply voltage drops below the cutoff voltage level, error detect module 770 asserts a fault-type error message.

During the periods when a handpiece 34 is not actuated, error detect module 770 modules the OVERLIP/OVERLIN-based ISENSE signal. Specifically, this signal is compared against a threshold signal to determine if the handpiece is drawing current above a threshold level. In some versions this threshold level is 50 mA. In the event error detect module 770 determines the current draw of the unactuated handpiece is above the threshold level, the module asserts a lockdown-type error message. This is because such true draw could indicate a fault in H-bridge settings.

An inductance sensing calibration module internal to the motor processor 224 (module not illustrated) provides inductance sensing gain and offset values. One process by which this module generates these values is described by reference to the flow chart of FIG. 52. Initially, in step 776, the handpiece motor 36 is driven for a short time. At this time, it is necessary to use an open loop process to start the motor from the zero speed position. In a step 778 the rotor is stopped in a known position. This is accomplished by momentarily established designed power and ground connections to the windings 234. For example windings M1 and M2 may be attached to the power supply rail; winding M3 is tied to ground. Immediately after step 778 is executed, current flow is measured through each of the windings 234, step 780. Current flow is measured in both directions through the windings 234 so there are a total of six measurements.

After the initial set of current flow measurements are made, in a step 782, the motor 36 is again actuated in the open-loop mode. The motor is stopped in second known position, step 784. This is, for example, accomplished by tying the M1 and M3 windings to the power supply rail and the M2 winding to ground. In a step 786 the six current flow measurements are again made.

Then, in a step 788, based on the two sets of current flow measurements the six (6) gain and six (6) offset values needed to generate the normalized current flow measurements are generated. These measurement may then be stored in a flash memory integral with the motor processor 224. Alternatively, these data may be written to the handpiece EEPROM or NOVRAM This method of this invention can be used at start up to facilitate the generation of the normalized current measurements needed for inductance sensed determination of rotor position. Post start-up, this method can be used to provide adjusted gain and offset values to compensate for any thermal or wear induced changes in measurement of winding current flow. This method can also be used as alternative to providing the inductance sensed gain and offset data in the handpiece NOVRAM.

The above-described calibration process is executed in situations when the handpiece is calibrated during the course of the surgeon's use of the handpiece. In such process, it should be understood that, after the open loop process is used to initially actuate the motor, the BEMF sensing is used to regulate higher speed commutation. Thus between steps 776 and 778 and between steps 782 and 784, the handpiece can be used in a conventional manner.

Alternatively, the console could, upon the coupling of the handpiece 34 to the console 32 subjects the handpiece to the calibration process. In this process, the console essentially first performs step 778 to move the motor rotor to a first known position. The measurements of step 780 are then taken. Then, bypassing step 782, step 784 to position the motor rotor in the second known position.

Figure 52:
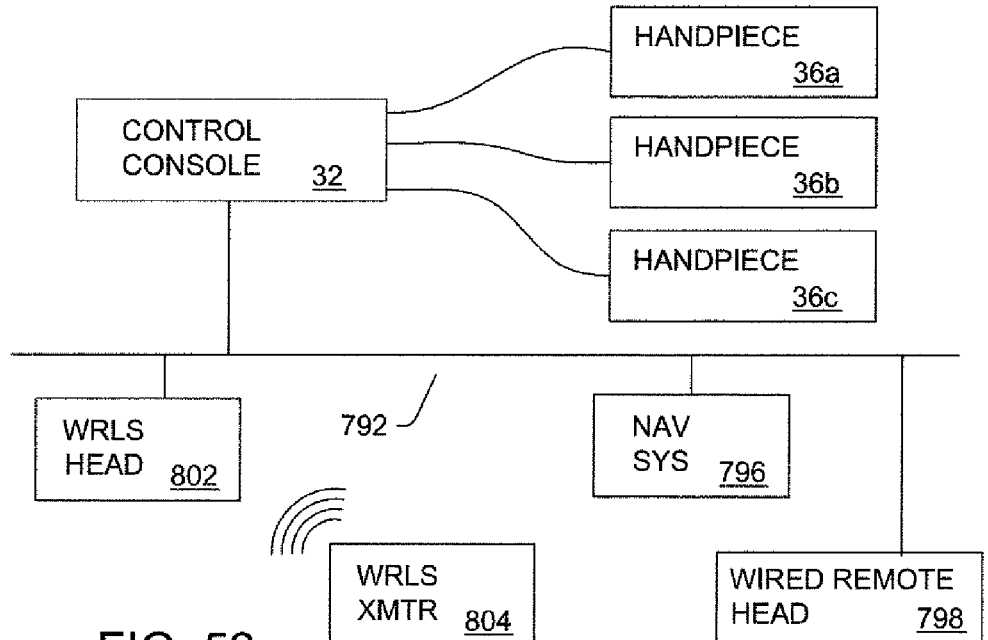
FIG. 52 is a block diagram of how the system of this invention may be connected to other devices in an operating room.

As discussed above, control console 32 has an interface to facilitate remote control of the handpieces 34 regulated by the system 30 of this invention. In FIG. 2A, the interface is shown as a 1394 Firewire interface 68. As seen in FIG. 52, the interface 68 facilitates the connection of the control console 32 to a bus 792.

Other devices connected to bus 792 are a navigation system 796 and a wired remote head 798. The navigation system, as is known in the art, is used to track the position and orientation of the handpiece 36 relative to the surgical site at which the procedure is being performed. Wired remote head 798 allows the surgeon to enter verbal commands to the other components connected to the bus 792. One such device is sold by the Applicants' Assignee under the trademark SIDNEE.

Another device connected to bus 792 is a wireless head 802. Wireless head 802 is a received capable of receiving signals emitted from a wireless device. One such device for example is a wireless footswitch. Integral with the wireless device is a wireless transmitter 804. A wireless footswitch has the same peddles and performs the same functions as a conventional footswitch 44 (FIG. 1). However, instead of the command signals being forward over a cable to the console, the wireless transmitter 804 transmits them to the wireless head 802. One suitable protocol for forwarding wireless signals between transmitter 804 and head 802 is wireless USB.

The wireless head 802 continuously forwards packets containing the commands to the control console 32. Once the packet transmission instructions are stripped from the packets by the interface 68, the packet contents are forwarded to the display controller 64. If a packet contains a command to start actuation a handpiece 36, the display controller 64 generates the appropriate initialization packet to the motor processor 224. After the handpiece is initialized, based on the signals from the wireless device, display controller 224 transmits speed set point packets to the motor processor 224 in the conventional manner.

Figure 53:
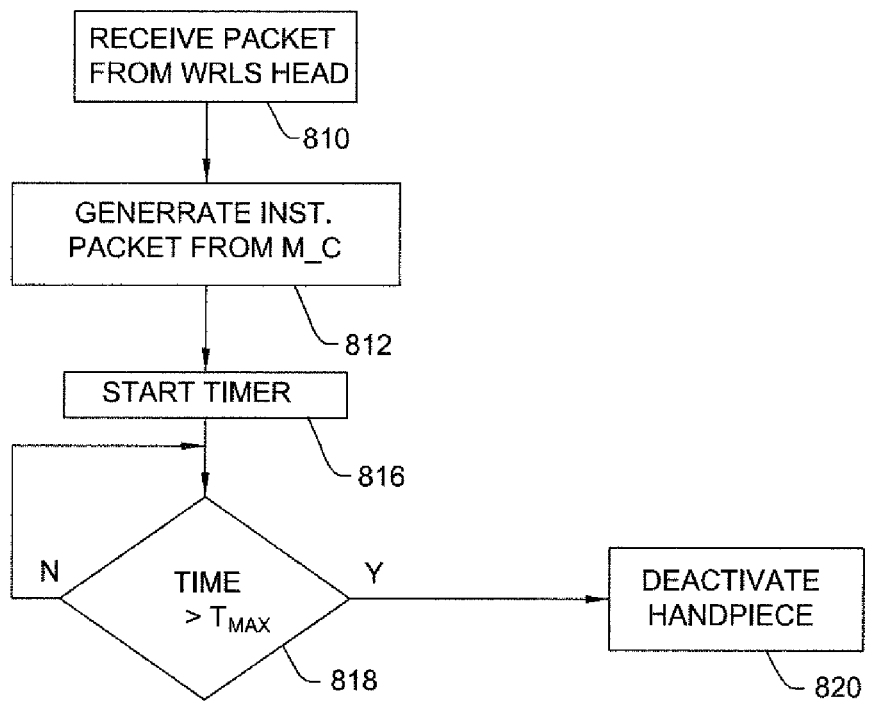
FIG. 53 is a flow chart of the process steps executed by the control console to maintain control integrity when a wireless device is employed to actuate a surgical handpiece.

Display controller 64 also executes a failsafe sequence when instructions are being received from the wireless head 802 to regulate the actuation of a handpiece 36. This sequence, as represented by the flow chart of FIG. 53, starts, in step 810, with the receipt of an instruction packet from the wireless head. Step 812 represents the generation of either an initialization or speed set point packet by the display controller 64 for execution by the motor processor 224. This latter packet, it is understood, is based on the contents of the packet from the wireless head 802.

In a step 816, the display controller starts a timer from when the packet is received from the wireless head 810. In a step 818 the elapsed time is compared to a maximum time, $T_{MAX}$. In some versions of this invention $T_{MAX}$ is between 100 and 500 msec. If, before the end of this time period, a new packet is received wireless head 802, the display controller 64 clears the timer and steps 810-818 are reexecuted (steps not shown.)

However, there may be instances when, the time count maintained becomes greater than $T_{MAX}$. If, in step 818, it is determined that this event has occurred, display controller, in a step 820 generates the signals to the motor processor 24 to cause the deactivation of the handpiece.

Thus, in the event the signal is lost from the wireless control device, console 32 does not continue to energize the active handpiece based on the last received wireless instructions. Instead, console 32 deactivates the handpiece 34. This ensures that because of a break in the stream of wireless instructions the handpiece is actuated in a manner contrary to the intent of the surgeon.

Control console 32 is also capable of receiving asynchronous commands generated by devices such as the navigation system 796 and remote head 798. Remote head 798 is used to generate specific stepped commands with regard to the on/off actuation of the handpiece and pump and operating settings of these devices. In the event the navigation system 796 determines the cutting accessory 35 is approaching a position at the surgical site at which the accessory should not be applied, the navigation system may slow or deactivate the associated handpiece.

Figure 55:
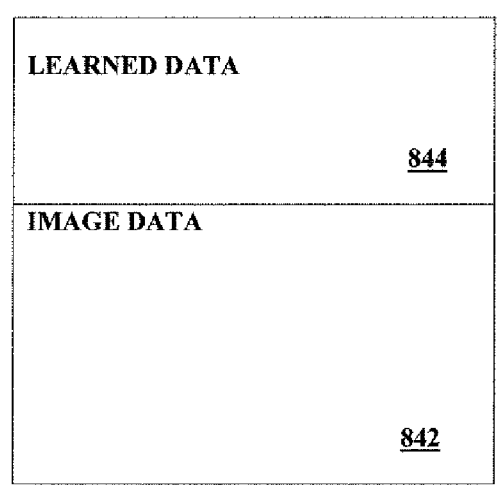
FIG. 55 is diagrammatic illustration of two handpiece data files maintained by the memory integral with the control console.

As represented by FIG. 55, either internal to the display controller 64 or a memory associated with it, there is an image data file 842. The image data file 842 contains, for each type of handpiece 34 that can be used with the system the basic operating parameter data for that type of handpiece. These data include the minimum and maximum speeds of the handpiece, if the motor can be oscillated, if the handpiece is used with a pump, and the pump fluid flow rates. Other data include information regarding the sequence in which energization signals are to be applied to the handpiece motor windings 234.

The storing of this information in the image data file reduces the amount of time required to load data into the display controller when a handpiece 34 is connected to a console 32.

Still another advantage of maintaining the image data file, is that it is possible to then retrieve information regarding the operating characteristics of a particular type of handpiece even though the handpiece is not attached to the console 32. These data are presented on the display 42. This thus makes it possible to load the preferred settings for a particular surgeon when he/she wants to use the handpiece without requiring that the handpiece 34 be physically attached t the console 32.

Figure 54:
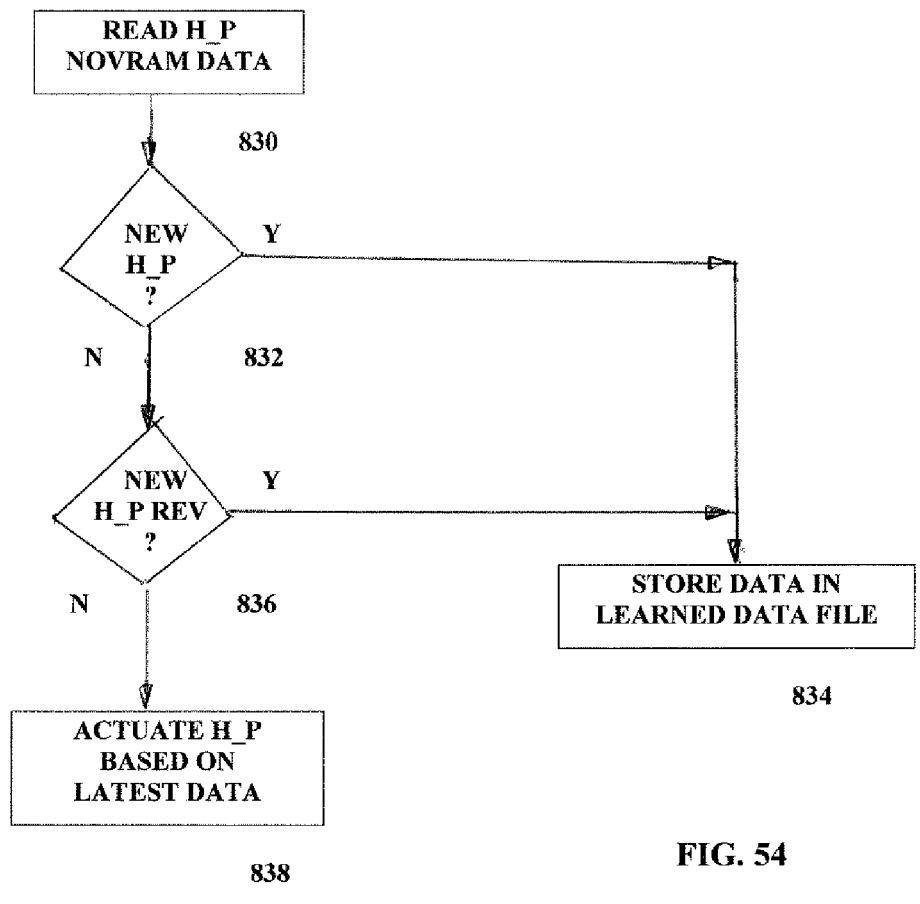
FIG. 54 is a flow chart of the process steps executed by the control console to ensure the data it stores about the complementary handpieces are current.

The process by which the data in the memory internal integral with the display controller 64 is provided with current handpiece data is now explained with reference to the flow chart of FIG. 54. Step 830 is the reading of the data in the handpiece NOVRAM 72. Based on the basic identification fields in the retrieved data, display controller 64, in a step 832, immediately determines if this is a new type of handpiece. More particularly, in step 832, display controller 64 makes this determination based on whether or not data in the image data file 842 or a complementary learned data file 844 contains data for the same type of handpiece 34.

If in step 832, it is determined that this is a new type of handpiece for which the console does not have any data, display controller executes a step 834. In step 834, the basic configuration data for this handpiece are written to the learned data file 844.

In a step 836, executed after step 832, display controller 64 also determines if the version of the handpiece type data it stores is the most current version. This process is performed by determining if the revision identification data from the handpiece NOVRAM 72 is newer than the revision identification for the handpiece in either the image data or learned data files 842 and 844, respectively. If this revision data in the handpiece NOVRAM 72 is newer, in step 834, these data are written into the learned data file 844.

Then, in a step 838, display controller 64 causes the handpiece 34 to be actuated based on the most current data for actuating it.

Figure 56:
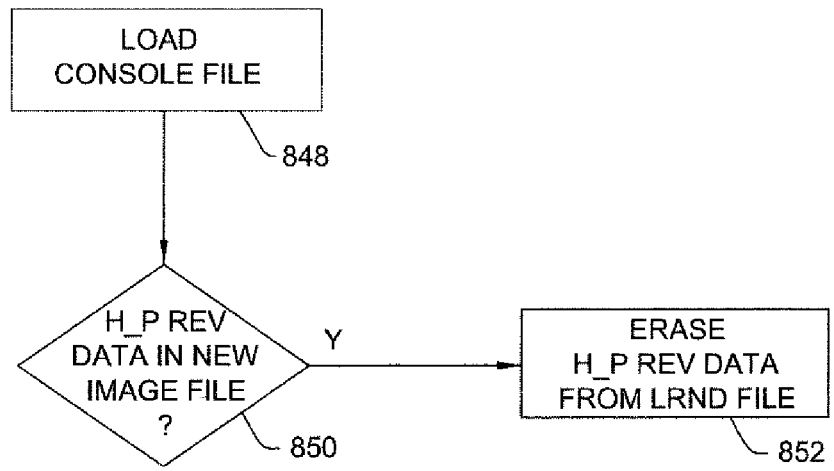
FIG. 56 is a flow chart of the process steps executed by the control console to avoid the storage of redundant handpiece data.

As depicted by the flow chart of FIG. 56, control console 32 is further configured to minimize the storage of redundant data in the learned data file 544. Specifically, as represented by step 848, new operating software is periodically loaded in the control console. This software includes may include a new image data file 842. In the event such a file exists, in a step 850, for each handpiece data file, display controller determines whether or not the revision version of the handpiece data file in the new image data file is the same or new than the version in the learned data file.

If, in step 848, the determination tests affirmative, in a step 852 the handpiece data file in the learned data file is erased.

Thus, as soon as a handpiece with new data is attached to control console 32, the new handpiece type data are loaded into the console memory. This eliminates the need to have to constantly load this data into the console each time this type of handpiece is attached. Whenever the console receives a new master file of current handpiece type data, the original and now redundant copy of this data are erased from its memory. This serves to ensure that console memory does not become filed with unneeded data.

As discussed in the above-mentioned and incorporated-by reference U.S. Pat. No. 6,017,354 and U.S. patent application Ser. No. 10/214,937, when a surgical handpiece with a NOVRAM 72 or a cutting accessory with an RFID is attached to a tool system, it is useful to occasional make a brief integration to determine if the tool or handpiece is still attached.

Figure 57:
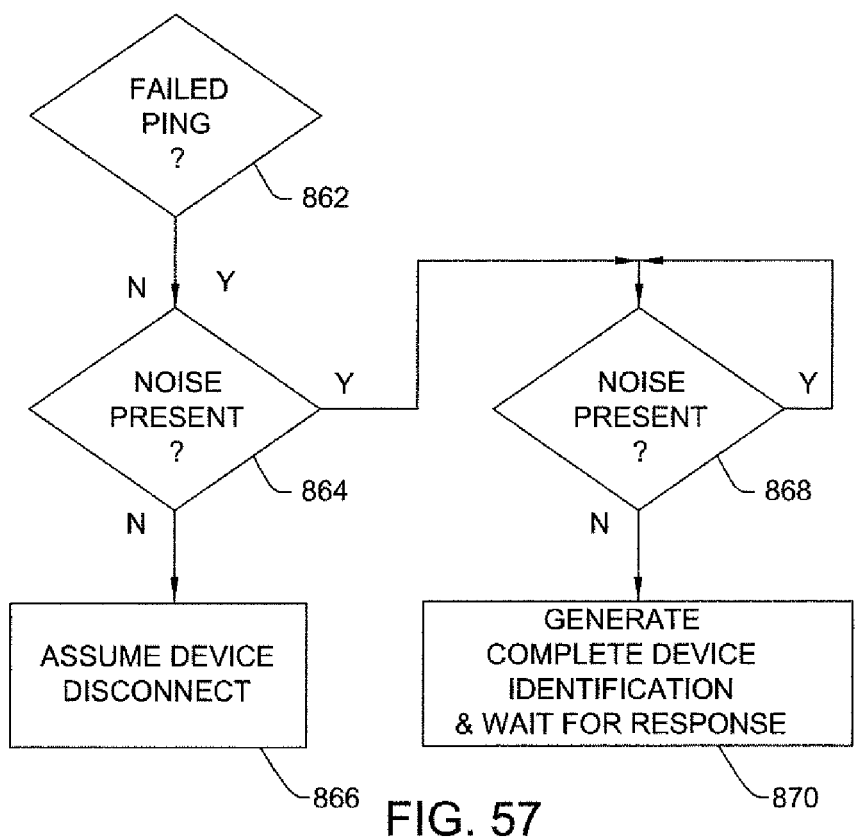
FIG. 57 is a flow chart of the process steps executed by the control console to provide immunity from false determinations of handpiece disconnections due to excessive ambient RF noise.

As described now with reference to the flow chart of FIG. 57, console 32 of this invention is constructed to provide immunity against the false determination of handpiece/accessory disconnect in the presence of significant RF noise. It should be understood that such noise may be present because some surgical devices, including those that are part of the system, when actuated, emit appreciable amounts of RF energy. This energy induces noise on the lines over which the signals from NOVRAMs and RFIDs are returned to the control console 32.

The process starts, after a step 862, when the display controller determines the control console 32 has not received a distinct response to a ping. A ping is the basic device present/absent inquiry that sent to an RFID or a NOVRAM. The response to a ping is a short acknowledgement of device presence. The ping response does not include any data identifying the device. If, however, there is significant noise, the sub assembly internal to the control console that receives the response, the handpiece interface 70, the footswitch interface 74 or the RFID interface 82, may not receive the discernable response.

Thus if in step 862, there is failure to receive a ping response, a step 864 is executed to determine if the failure is due to the presence of significant noise. The method by which this determination is made is a function of the type of device the presence of which is being detected.

If the device is one in which is one in which a signal is expected back from an RFID, in step 864 the RFID interface 82 evaluates if, in response to the ping, there was a measurable change in signal strength along the return line above ambient noise. If there change the signal level, the RFID interface 82 recognizes the environment as being one in which noise prevented the interface from receive an explicit ping response. The RFID interface 82 reports this determination to the display controller 64.

Alternatively, the noise determination may be made on a more inferential basis. Thus, if the attached device is a handpiece or a corded footswitch, step 864 may be performed by evaluating whether or not a component internal to that is supposed to draw current is actually drawing current. Such a component is an analog Hall sensor that is present in some handpieces as part of an assembly for regulating handpiece actuation. For such a device the handpiece interface controller 470 (FIG. 35A) monitors the current drawn through the HP_PWR connection. If the current drawn is above a nominal level, interface controller 470 assumes the current drawing component, and therefore the handpiece, remain attached. Interface controller 470 reports this determination to the display controller 64.

It should be understood the above method of noise evaluation works best when the component for which the current is being evaluated draws an appreciable amount of current. Some components internal to handpiece or a footswitch, such as temperature sensor or a digital Hall sensor, may not draw appreciable current.

Other devices attached to the console 32 may not have internal components that continually draw appreciable amounts of current. A corded footswitch 44 is such a device. For this type of device, the evaluation of step 864 consists of monitoring the voltage level of output signal from a device component that is often in the nominal state. Specifically, the interface again, by example, is performed by the handpiece interface controller 470. Specifically, the interface controller 470, monitors the analog out HP_EV signal received from the component internal to the attached device. A thermistor or some Hall sensors may output this type of signal. The interface 470 digitizes this signal and forwards the digitized signal to the display controller 64.

Figure 58A:
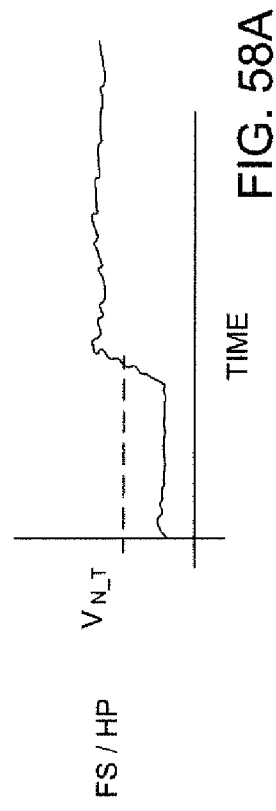
FIGS. 58A and 58B illustrate two of the signals monitored by the control console in separate processes to determine whether or not there is excessive ambient RF noise.

The display controller 64 compares this nominal signal to a noise threshold value, $V_{N\_T}$. Graphically, FIG. 58A represents such a signal that is initially below and then rises above this threshold. The rise of this signal level above the $V_{N\_T}$ level is interpreted by the display controller 64 as indication that ambient RF noise is preventing receipt of a complete ping response.'

Figure 58B:
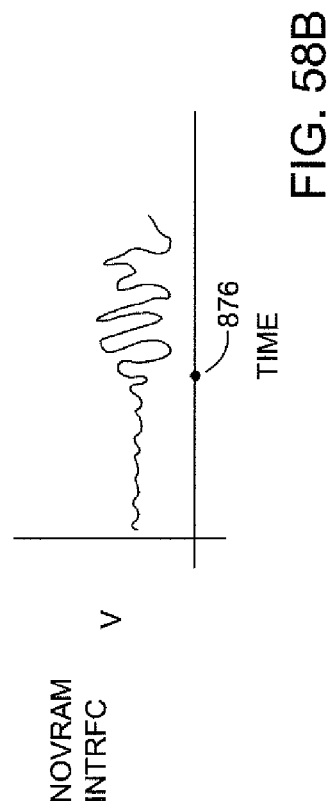

A fourth means for executing step 864 is executed if the device has no other signal generating components other than a NOVRAM. In this instance, the NOVRAM interface 78 monitors the signal returned from the NOVRAM. In the absence of a data/read write transaction, this signal is usually at a fixed level, often 5 VDC. In its execution of step 864, the NOVRAM interface 78, monitors the signal present on the communications line connected to the NOVRAM to determine if it fluctuates from the fixed level. Graphically, FIG. 58B represents such a signal. At times before point 876, the signal is generally at the fixed level. At times after point 876, there is significant fluctuation. The NOVRAM interface interprets this fluctuation in signal strength as indicating the presence of appreciable RF noise. This determination is reported to the display controller 64.

In many circumstances the test of 864 will be negative; it is determined there is no noise present. If this determination is made, the display controller 64 interprets the failure of the ping to indicate the device was disconnected from the system, step 866.

If RF noise is present, the test of step 864 is affirmative. In this event the noise determination test is continually reexecuted. In FIG. 57, this portion of the process is represented by the continually reexecution of step 868. The method of execution of step 868 is identical to that of the method of step 864.

Eventually, the RF noise generating device will be deactivated. Once this occurs, the test of step 868 will return a negative evaluation for presence of noise. In response to this step, display controller, in step 870, causes the NOVRAM interface 78 or RFID interface 82 to forward a complete device identification request to the associated NOVRAM or RFID. In response to this request, the NOVRAM or RFID output signal that identifies the device with specificity. This response is of greater length than the ping response. The display controller generates this type of request so it can determine if in fact the device attached to the system before the increase in ambient noise is the device present after the noise levels drop.

Thus, control console 32 is further configured so that, in situations where appreciable RF or EM induced noise is present, the noise does not result in a false indication that a device has been disconnected from the system 30. Further upon the noise level dropping, the control console 32 immediately verifies that the attached device was the one attached before the rise in noise levels.

It should likewise be appreciated that in other versions of the invention, the control console may be provided with more than three (3) sockets 40. This makes it possible to simultaneously connect more than three powered surgical tools or handpieces to the console. Thus, more than three handpieces can simultaneously be ready for use. Thus, generically, the console can be configured to receive M surgical handpieces (M>1) while simultaneously driving N handpieces, (N>1) wherein (M>N).

In still other versions of the invention, the console may be designed so that the number of handpieces the console can energize equals the number of handpieces that, at any one time, can be connected to the console (M=N).

It should therefore be appreciated that the above description is directed to one particular version of this invention. Other versions of the invention may have features different than what has been described. For example, each of the above features may not be incorporated into all versions of this invention.

Also, other versions of this invention may have different features. Other means than inductance sensing may be employed to provide the torque-down-to-stall control of the handpiece motor.

The process steps executed and the sequence in which the steps are executed are likewise only exemplary and not limiting.

It should likewise be realized that the features of this invention may be incorporated into cordless powered surgical handpieces. This type of handpiece, instead of being energized by a single from a control console, receives its energization signal from an attached battery. As is known from the Applicants' Assignee's U.S. Patent Application No. 60/694,592, POWERED SURGICAL TOOL WITH SEALED CONTROL MODULE, filed 38 Jun. 2005, the contents of which are incorporated herein by reference, it is known to provide this type of tool with an internal processor for regulating the application of energization signals to the tool power consuming unit. This process can perform the signal processing steps of this invention.

Other means may be employed to improve the way BEMF signals are used to determine rotor position for the purpose of regulating commutation.

What is claimed is:

1. A system for energizing powered surgical handpieces comprising:
    a control console comprising:
        a first footswitch socket and a second footswitch socket, each of said first footswitch socket and said second footswitch socket being configured to receive a footswitch cable attached to a different footswitch;
        a first handpiece socket and a second handpiece socket, each of said first handpiece socket and said second handpiece socket being configured to receive a handpiece cable attached to a handpiece; and
        at least one driver configured to supply an energization signal to a motor of a handpiece coupled to said first handpiece socket or said second handpiece socket;
    a first footswitch comprising a first footswitch cable received by said first footswitch socket and a first switch that is actuated to communicate a first control signal to said control console;
    a second footswitch comprising a second footswitch cable received by said second footswitch socket and a second switch that is actuated to communicate a second control signal to said control console;
    a first handpiece comprising a first handpiece cable for being received by said first handpiece socket and a first motor; and
    a second handpiece comprising a second handpiece cable being received by said second handpiece socket and a second motor,
    wherein said control console is further configured to:
        map said first footswitch to said first handpiece received by said control console and said second footswitch to said first handpiece received by said control console, such that, based on the first control signal communicated from said first footswitch, said control console controls a driver of said at least one driver to selectively supply an energization signal to said first motor of said first handpiece to control a speed of said first motor, and based on the second control signal communicated from said second footswitch, said control console controls the driver of said at least one driver to selectively supply an energization signal to said first motor of said first handpiece to control a speed of said first motor, wherein said control console controls the driver of said at least one driver based on one of the first control signal and the second control signal;
        map said first footswitch to said second handpiece received by said control console and said second footswitch to said second handpiece received by said control console, such that, based on the first control signal communicated from said first footswitch, said control console controls a driver of said at least one driver to selectively supply an energization signal to said second motor of said second handpiece to control a speed of said second motor, and based on the second control signal communicated from said second footswitch, said control console controls the driver of said at least one driver to selectively supply an energization signal to said second motor of said second handpiece to control a speed of said second motor, wherein said control console controls the driver of said at least one driver based on one of the first control signal and the second control signal;
        emit a light representing said first handpiece and of a first color and a light representing said second handpiece and of a second color different from the first color; and
        emit a light representing one of said first footswitch and said second footswitch, a color of the light corresponding to the color of the light representing the handpiece to which said one of said first footswitch and said second footswitch is mapped.

2. The system for energizing powered surgical handpieces of claim 1, wherein said control console is further configured to:
    emit a light representing said first footswitch of a color corresponding to the color of the light representing the handpiece to which said first footswitch is mapped; and
    emit a light representing said second footswitch of a color corresponding to the color of the light representing the handpiece to which said second footswitch is mapped.

3. The system for energizing powered surgical handpieces of claim 1, wherein said control console is further configured to:
    determine that more than one handpiece is received by said control console and more than one footswitch is received by said control console; and
    force a user to enter mapping instructions to indicate which footswitch of said more than one footswitches should be mapped to which handpiece of the more than one handpieces by said control console.

4. The system for energizing powered surgical handpieces of claim 1, wherein said first footswitch communicates the first control signal to said control console after said second footswitch communicates said second control signal to said control console, and wherein said control console is further configured to:
    control a driver of said at least one driver based on one of the first control signal and the second control signal when said first footswitch is mapped to said first handpiece and said second footswitch is mapped to said first handpiece by controlling the driver to supply an energization signal to said first motor of said first handpiece based on the first control signal after said second footswitch is no longer communicating said second control signal; and
    control a driver of said at least one driver based on one of the first control signal and the second control signal when said first footswitch is mapped to said second handpiece and said second footswitch is mapped to said second handpiece by controlling the driver to supply an energization signal to said second motor of said second handpiece based on the first control signal after said second footswitch is no longer communicating said second control signal.

5. The system for energizing powered surgical handpieces of claim 1, wherein said at least one driver comprises a first driver and a second driver, and wherein said control console is further configured to map said first footswitch to said first handpiece and said second footswitch to said second handpiece, such that, based on the first control signal communicated from said first footswitch, said control console controls said first driver to selectively supply an energization signal to said first motor of said first handpiece to control a speed of said first motor, and based on the second control signal communicated from said second footswitch, said control console controls said second driver to selectively supply an energization signal to said second motor of said second handpiece to control a speed of said second motor.

6. The system for energizing powered surgical handpieces of claim 1, wherein said control console is further configured to:
   read data from a memory integral with said first handpiece; and
   apply an energization signal to said first handpiece based on the data read from the memory of said first handpiece.

7. The system for energizing powered surgical handpieces of claim 5, wherein said control console is further configured to, in response to mapping said first footswitch to said first handpiece and said second footswitch to said second handpiece, emit a light representing said first footswitch of the first color and emit a light representing said second footswitch of the second color.

8. The system for energizing powered surgical handpieces of claim 5, wherein said control console, based on the first control signal communicated from said first footswitch, controls said first driver to supply an energization signal to said first motor of said first handpiece and, simultaneously therewith, based on the second control signal communicated from said second footswitch, controls said second driver to supply an energization signal to said second motor of said second handpiece.

9. The system for energizing powered surgical handpieces of claim 1, wherein said control console is further configured to:
   in response to mapping said first footswitch to said first handpiece and said second footswitch to said first handpiece, emit a light representing said first footswitch of the first color and emit a light representing said second footswitch of the first color; and
   in response to mapping said first footswitch to said second handpiece and said second footswitch to said second handpiece, emit a light representing said first footswitch of the second color and emit a light representing said second footswitch of the second color.

10. A system for energizing powered surgical handpieces comprising:
   a control console comprising:
      a first handpiece socket and a second handpiece socket, each of said first handpiece socket and said second handpiece socket being configured to receive a cable attached to a handpiece; and
      at least one driver configured to supply an energization signal to a motor of a handpiece received by said handpiece sockets;
   a first footswitch comprising a first switch that is actuated to communicate a first control signal to said control console;
   a second footswitch comprising a second switch that is actuated to communicate a second control signal to said control console;
   a first handpiece comprising a first handpiece cable received by said first handpiece socket and a first motor; and
   a second handpiece comprising a second handpiece cable received by said second handpiece socket and a second motor;
   wherein said control console is further configured to:
      map said first footswitch to said first handpiece received by said control console and said second footswitch to said first handpiece received by said control console, such that, based on the first control signal communicated from said first footswitch, said control console selectively supplies an energization signal to said first motor of said first handpiece to control a speed of said first motor, and based on the second control signal communicated from said second footswitch, said control console selectively supplies an energization signal to said first motor of said first handpiece to control a speed of said first motor;
      map said first footswitch to said second handpiece received by said control console and said second footswitch to said second handpiece received by said control console, such that, based on the first control signal communicated from said first footswitch, said control console selectively supplies an energization signal to said second motor of said second handpiece to control a speed of said second motor, and based on the second control signal communicated from said second footswitch, said control console selectively supplies an energization signal to said second motor of said second handpiece to control a speed of said second motor;
      emit a light representing said first handpiece and of a first color and a light representing said second handpiece and of a second color different from the first color; and
      emit a light representing one of said first footswitch and said second footswitch, a color of the light corresponding to the color of the light representing the handpiece to which said one of said first footswitch and said second footswitch is mapped.

11. The system for energizing powered surgical handpieces of claim 10, wherein said control console is further configured to:
   emit a light representing said first footswitch of a color corresponding to the color of the light representing the handpiece to which said first footswitch is mapped; and
   emit a light representing said second footswitch of a color corresponding to the color of the light representing the handpiece to which said second footswitch is mapped.

12. The system for energizing powered surgical handpieces of claim 10, wherein said control console is further configured to:
   in response to mapping said first footswitch to said first handpiece and said second footswitch to said first handpiece, emit a light representing said first footswitch of the first color and emit a light representing said second footswitch of the first color; and
   in response to mapping said first footswitch to said second handpiece and said second footswitch to said second handpiece, emit a light representing said first footswitch of the second color and emit a light representing said second footswitch of the second color.

13. The system for energizing powered surgical handpieces of claim 10, wherein said control console is further configured to:
   determine that more than one handpiece is received by said control console and more than one footswitch is received by said control console; and
   force a user to enter mapping instructions to indicate which footswitch of said more than one footswitches should be mapped to which handpiece of the more than one handpieces by said control console.

14. The system for energizing powered surgical handpieces of claim 10, wherein said control console is further configured to:
control a driver of said at least one driver based on one of the first control signal and the second control signal when said first footswitch is mapped to said first handpiece and said second footswitch is mapped to said first handpiece; and
control a driver of said at least one driver based on one of the first control signal and the second control signal when said first footswitch is mapped to said second handpiece and said second footswitch is mapped to said second handpiece.

15. The system for energizing powered surgical handpieces of claim 14, wherein said first footswitch communicates the first control signal to said control console after said second footswitch communicates said second control signal to said control console, and wherein said control console is further configured to:
control a driver of said at least one driver based on one of the first control signal and the second control signal when said first footswitch is mapped to said first handpiece and said second footswitch is mapped to said first handpiece by controlling the driver to supply an energization signal to said first motor of said first handpiece based on the first control signal after said second footswitch is no longer communicating said second control signal; and
control a driver of said at least one driver based on one of the first control signal and the second control signal when said first footswitch is mapped to said second handpiece and said second footswitch is mapped to said second handpiece by controlling the driver to supply an energization signal to said second motor of said second handpiece based on the first control signal after said second footswitch is no longer communicating said second control signal.

16. The system for energizing powered surgical handpieces of claim 10, wherein said at least one driver comprises a first driver and a second driver, and wherein said control console is further configured to map said first footswitch to said first handpiece and said second footswitch to said second handpiece, such that, based on the first control signal communicated from said first footswitch, said control console controls said first driver to selectively supply an energization signal to said first motor of said first handpiece to control a speed of said first motor, and based on the second control signal communicated from said second footswitch, said control console controls said second driver to selectively supply an energization signal to said second motor of said second handpiece to control a speed of said second motor.

17. The system for energizing powered surgical handpieces of claim 16, wherein said control console, based on the first control signal communicated from said first footswitch, controls said first driver to supply an energization signal to said first motor of said first handpiece and, simultaneously therewith, based on the second control signal communicated from said second footswitch, controls said second driver to supply an energization signal to said second motor of said second handpiece.

18. The system for energizing powered surgical handpieces of claim 16, wherein said control console is further configured to, in response to mapping said first footswitch to said first handpiece and said second footswitch to said second handpiece, emit a light representing said first footswitch of the first color and emit a light representing said second footswitch of the second color.

19. The system for energizing powered surgical handpieces of claim 10, wherein said control console further comprises a first footswitch socket and a second footswitch socket, each of said first footswitch socket and said second footswitch socket being configured to receive a footswitch cable attached to a different footswitch, wherein said first footswitch comprises a first footswitch cable received by said first footswitch socket, and wherein said second footswitch comprises a second footswitch cable received by said second footswitch socket.

20. The system for energizing powered surgical handpieces of claim 10, wherein said control console is further configured to:
read data from a memory integral with said first handpiece; and
apply an energization signal to said first handpiece based on the data read from the memory of said first handpiece.

* * * * *